US006992175B1

(12) United States Patent
Fox et al.

(10) Patent No.: US 6,992,175 B1
(45) Date of Patent: Jan. 31, 2006

(54) NUCLEIC ACIDS ENCODING EPH-LIKE RECEPTOR TYROSINE KINASES

(75) Inventors: Gary M. Fox, Newbury Park, CA (US); Andrew A. Welcher, Glendale, CA (US); Shuqian Jing, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/378,759

(22) Filed: Aug. 23, 1999

Related U.S. Application Data

(60) Division of application No. 08/702,367, filed on Aug. 21, 1996, now Pat. No. 5,981,246, which is a continuation of application No. 08/229,509, filed on Apr. 15, 1994, now abandoned.

(51) Int. Cl.
| | |
|---|---|
| C12P 21/08 | (2006.01) |
| C12P 21/02 | (2006.01) |
| C07H 21/04 | (2006.01) |
| C07K 1/00 | (2006.01) |
| G01N 33/567 | (2006.01) |

(52) U.S. Cl. ............... 530/388.22; 530/350; 435/69.5; 536/23.5; 514/2; 436/501

(58) Field of Classification Search ............... 530/350, 530/388.22; 435/6, 7.2, 7.21, 69.1, 252.3, 435/69.5; 536/23.5; 514/2; 436/501
See application file for complete search history.

(56) References Cited

U.S. PATENT DOCUMENTS 4,816,567 A * 3/1989 Cabilly et al.

FOREIGN PATENT DOCUMENTS

| CA | A-2 083 521 | 10/1993 |
| DE | A-42 33 782 | 4/1994 |
| WO | WO-A-93 00425 | 1/1993 |
| WO | WO 95/27061 A | 10/1995 |
| WO | WO 95/30326 A | 11/1995 |

OTHER PUBLICATIONS

Sequence alignment: 09378759-11 and Pasquale EB, Cell Regulation 2(7)523-534, 1991.*
Iwase et al., Biochem. Biophys. Res. Comm. 194(2)698-705, 1993.*
Kirby, J. Immunology, 1992, W.H. Freeman and Company, pp. 100-101.*
Bohme et al., Oncogene 8, 2857-2862 (1993).
Boyd et al., J. Biol. Chem. 267, 3262-3267 (1992).
Capon et al., Nature 337, 525-531, 1989.
Chan and Watt, Oncogene 6, 1057-1061 (1991).
Chomczynski and Sacchi, Anal. Biochem 162, 156-159 (1987).
Hanks and Quinn, Methods Enzymol. 200, 38-62 (1991).
Harlow and Lane, In Antibodies: A Laboratory Manual (1988), pp. iii-ix.
GenBank Accession No. D14717-Submitted Oct. 15, 1993.
Gilardi-Hebenstrelt et al., Oncogene 7, 2499-2506 (1992).
Hirai et al., Science 238, 1717-1720 (1987).
Holzman et al., Mol. Cell. Biol. 10, 5830-5838 (1990).
Iwase et al., Biochem. Biophys. Res. Commun., vol. 194 (2), p. 698 (1993).
Lai and Lemke, Neuron 6, 691-704 (1991).
Lax et al., Embo, vol. 8 (2), p. 421, 1989.
Lhoták et al., Mol. Cell. Biol. 11, 2496-2502 (1991).
Lindberg and Pasquale, Methods Enzymol. 200, 557-564 (1991).
Lindberg et al., Mol. Cell. Biol. 10,6316-6324 (1990),
Maisonpierre et al., Oncogene 8, 3277-3288 (1993).
Marcelle & Eichmann, Oncogene 7, 2479-2487 (1992).
Maru et al., Oncogene 5, 199-204 (1990).
Messing, Methods Enzymol. (1983).
Nieto et al., Development 116, 1137-1150 (1992).
Pacifici et al., 269, 1571-1574 (1994).
Pasquale et al., J. Neuroscience 12, 3956-3967 (1992).
Pasquale, Cell Regulation 2, 523-534 (1991).
Remington's Pharmaceutical Sciences 18th Ed., A.R. Gennaro, ed. (1990), pp. xv and xvi.
Sajjadi and Pasquale, Oncogene 8, 1807-1813 (1993).
Sajjadi et al., The New Biologist 3, 769-778 (1991).
Sambrook et al., Molecular Cloning: A Laboratory Manual, Cold Spring Harbor Laboratory Press, 2nd ed. (1989), pp. xi-xxxviii.
Sambrook et al., Molecular Cloning: A Laboratory Manual, vol. 3, Chapters 16, pp. 16.1-16.30 and 17, pp. 17.1-17.28, Cold Spring Harbor Laboratory Press, 2nd ed. (1989).
Smith et al., Science, vol. 238, p. 1704 (1987).
Tuzi et al., British Journal of Cancer 69, 417-421 (1994).
Ullrich et al., Cell 61, 203-212 (1990),
Van der Geer et al., Annu. Rev. Cell Bio. 10, 251-337 (1994).
Wicks et al., Proc. Natl. Acad. Sci. USA 89, 1611-1615 (1992).
Wilks, Proc. Natl. Acad. Sci., USA 86, 1603-1607 (1989).
Yanisch-Perron et al., Gene 33, 103-119 (1985).
Henkemeyer et al., "Immunolocalization of the Nuk receptor tyrosine kinase suggests roles in segmental patterning of the brain and axonogenesis" Oncogene, 9(4): 1001-1014 (1994).
Fox et al., "cDNA cloning and tissue distribution of five human eph-like receptor protein-tyrosine kinases" Oncogene, 10(5): 897-905 (1995).
European Search Report dated Sep. 16, 2004, for European Patent Application No. 04007136.7.

* cited by examiner

Primary Examiner—Elizabeth Kemmerer
Assistant Examiner—Michael Brannock
(74) Attorney, Agent, or Firm—Finnegan, Henderson, Farabow, Garrett & Dunner, LLP

(57) ABSTRACT

Four novel members of the EPH sub-family of receptor protein tyrosine kinases are disclosed. Nucleic acid sequences encoding receptor proteins, recombinant plasmids and host cells for expression, and methods of producing and using such receptors are also disclosed.

8 Claims, 33 Drawing Sheets

FIG. 1A

| | | | | | | | | | | | | | | | | |
|---|---|---|---|---|---|---|---|---|---|---|---|---|---|---|---|---|
| CTG | CTC | GCC | GCC | GTG | GAA | GAA | ACG | CTA | ATG | GAC | TCC | ACT | ACA | GCG | ACT | 48 |
| Leu | Leu | Ala | Ala | Val | Glu | Glu | Thr | Leu | Met | Asp | Ser | Thr | Thr | Ala | Thr | |
| 1 | | | | 5 | | | | | 10 | | | | | 15 | | |
| GCT | GAG | CTG | GGC | TGG | ATG | GTG | CAT | CCT | CCA | TCA | GGG | TGG | GAA | GAG | GTG | 96 |
| Ala | Glu | Leu | Gly | Trp | Met | Val | His | Pro | Pro | Ser | Gly | Trp | Glu | Glu | Val | |
| | | | 20 | | | | | 25 | | | | | 30 | | | |
| AGT | GGC | TAC | GAT | GAG | AAC | ATG | AAC | ACG | ATC | CGC | ACG | TAC | CAG | GTG | TGC | 144 |
| Ser | Gly | Tyr | Asp | Glu | Asn | Met | Asn | Thr | Ile | Arg | Thr | Tyr | Gln | Val | Cys | |
| | | | 35 | | | | | 40 | | | | | 45 | | | |
| AAC | GTG | TTT | GAG | TCA | AGC | CAG | AAC | AAC | TGG | CTA | CGG | ACC | AAG | TTT | ATC | 192 |
| Asn | Val | Phe | Glu | Ser | Ser | Gln | Asn | Asn | Trp | Leu | Arg | Thr | Lys | Phe | Ile | |
| | | 50 | | | | | 55 | | | | | 60 | | | | |
| CGG | CGC | CGT | GGG | GCC | CAC | CGC | ATC | CAC | GTG | GAG | ATG | AAG | TTT | TCG | GTG | 240 |
| Arg | Arg | Arg | Gly | Ala | His | Arg | Ile | His | Val | Glu | Met | Lys | Phe | Ser | Val | |
| 65 | | | | 70 | | | | | 75 | | | | | 80 | | |
| CGT | GAC | TGC | AGC | AGC | ATC | CCC | AGC | GTG | CCT | GGC | TCC | TGC | AAG | GAG | ACC | 288 |
| Arg | Asp | Cys | Ser | Ser | Ile | Pro | Ser | Val | Pro | Gly | Ser | Cys | Lys | Glu | Thr | |
| | | | | 85 | | | | | 90 | | | | | 95 | | |
| TTC | AAC | CTC | TAT | TAC | TAT | GAG | GCT | GAC | TTT | GAC | TCG | GCC | ACC | AAG | ACC | 336 |
| Phe | Asn | Leu | Tyr | Tyr | Tyr | Glu | Ala | Asp | Phe | Asp | Ser | Ala | Thr | Lys | Thr | |
| | | | | 100 | | | | | 105 | | | | | 110 | | |
| TTC | CCC | AAC | TGG | ATG | GAG | AAT | CCA | TGG | GTG | AAG | GTG | GAT | ACC | ATT | GCA | 384 |
| Phe | Pro | Asn | Trp | Met | Glu | Asn | Pro | Trp | Val | Lys | Val | Asp | Thr | Ile | Ala | |
| | | | 115 | | | | | 120 | | | | | 125 | | | |
| GCC | GAC | GAG | AGC | TTC | TCC | CAG | GTG | GAC | CTG | GGT | GGC | CGC | GTC | ATG | AAA | 432 |
| Ala | Asp | Glu | Ser | Phe | Ser | Gln | Val | Asp | Leu | Gly | Gly | Arg | Val | Met | Lys | |
| | | 130 | | | | | 135 | | | | | 140 | | | | |
| ATC | AAC | ACC | GAG | GTG | CGG | AGC | TTC | GGA | CCT | GTG | TCC | CGC | AGC | GGC | TTC | 480 |
| Ile | Asn | Thr | Glu | Val | Arg | Ser | Phe | Gly | Pro | Val | Ser | Arg | Ser | Gly | Phe | |
| 145 | | | | 150 | | | | | 155 | | | | | 160 | | |
| TAC | CTG | GCC | TTC | CAG | GAC | TAT | GGC | GGC | TGC | ATG | TCC | CTC | ATC | GCC | GTG | 528 |
| Tyr | Leu | Ala | Phe | Gln | Asp | Tyr | Gly | Gly | Cys | Met | Ser | Leu | Ile | Ala | Val | |
| | | | | 165 | | | | | 170 | | | | | 175 | | |
| CGT | GTC | TTC | TAC | CGC | AAG | TGC | CCC | CGC | ATC | ATC | CAG | AAT | GGC | GCC | ATC | 576 |
| Arg | Val | Phe | Tyr | Arg | Lys | Cys | Pro | Arg | Ile | Ile | Gln | Asn | Gly | Ala | Ile | |
| | | | | 180 | | | | | 185 | | | | | 190 | | |

FIG. IB

```
TTC CAG GAA ACC CTG TCG GGG GCT GAG AGC ACA TCG CTG GTG GCT GCC      624
Phe Gln Glu Thr Leu Ser Gly Ala Glu Ser Thr Ser Leu Val Ala Ala
        195             200             205

CGG GGC AGC TGC ATC GCC AAT GCG GAA GAG GTG GAT GTA CCC ATC AAG      672
Arg Gly Ser Cys Ile Ala Asn Ala Glu Glu Val Asp Val Pro Ile Lys
        210             215             220

CTC TAC TGT AAC GGG GAC GGC GAG TGG CTG GTG CCC ATC GGG CGC TGC      720
Leu Tyr Cys Asn Gly Asp Gly Glu Trp Leu Val Pro Ile Gly Arg Cys
225             230             235             240

ATG TGC AAA GCA GGC TTC GAG GCC GTT GAG AAT GGC ACC GTC TGC CGA      768
Met Cys Lys Ala Gly Phe Glu Ala Val Glu Asn Gly Thr Val Cys Arg
                245             250             255

GGT TGT CCA TCT GGG ACT TTC AAG GCC AAC CAA GGG GAT GAG GCC TGT      816
Gly Cys Pro Ser Gly Thr Phe Lys Ala Asn Gln Gly Asp Glu Ala Cys
                260             265             270

ACC CAC TGT CCC ATC AAC AGC CGG ACC ACT TCT GAA GGG GCC ACC AAC      864
Thr His Cys Pro Ile Asn Ser Arg Thr Thr Ser Glu Gly Ala Thr Asn
        275             280             285

TGT GTC TGC CGC AAT GGC TAC TAC AGA GCA GAC CTG GAC CCC CTG GAC      912
Cys Val Cys Arg Asn Gly Tyr Tyr Arg Ala Asp Leu Asp Pro Leu Asp
        290             295             300

ATG CCC TGC ACA ACC ATC CCC TCC GCG CCC CAG GCT GTG ATT TCC AGT      960
Met Pro Cys Thr Thr Ile Pro Ser Ala Pro Gln Ala Val Ile Ser Ser
305             310             315             320

GTC AAT GAG ACC TCC CTC ATG CTG GAG TGG ACC CCT CCC CGC GAC TCC     1008
Val Asn Glu Thr Ser Leu Met Leu Glu Trp Thr Pro Pro Arg Asp Ser
                325             330             335

GGA GGC CGA GAG GAC CTC GTC TAC AAC ATC ATC TGC AAG AGC TGT GGC     1056
Gly Gly Arg Glu Asp Leu Val Tyr Asn Ile Ile Cys Lys Ser Cys Gly
        340             345             350

TCG GGC CGG GGT GCC TGC ACC CGC TGC GGG GAC AAT GTA CAG TAC GCA     1104
Ser Gly Arg Gly Ala Cys Thr Arg Cys Gly Asp Asn Val Gln Tyr Ala
        355             360             365

CCA CGC CAG CTA GGC CTG ACC GAG CCA CGC ATT TAC ATC AGT GAC CTG     1152
Pro Arg Gln Leu Gly Leu Thr Glu Pro Arg Ile Tyr Ile Ser Asp Leu
        370             375             380

CTG GCC CAC ACC CAG TAC ACC TTC GAG ATC CAG GCT GTG AAC GGC GTT     1200
Leu Ala His Thr Gln Tyr Thr Phe Glu Ile Gln Ala Val Asn Gly Val
385             390             395             400
```

FIG. 1C

| | | |
|---|---|---|
| ACT GAC CAG AGC CCC TTC TCG CCT CAG TTC GCC TCT GTG AAC ATC ACC<br>Thr Asp Gln Ser Pro Phe Ser Pro Gln Phe Ala Ser Val Asn Ile Thr<br>                405                        410                        415 | 1248 |
| ACC AAC CAG GCA GCT CCA TCG GCA GTG TCC ATC ATG CAT CAG GTG AGC<br>Thr Asn Gln Ala Ala Pro Ser Ala Val Ser Ile Met His Gln Val Ser<br>                420                        425                        430 | 1296 |
| CGC ACC GTG GAC AGC ATT ACC CTG TCG TGG TCC CAG CCG GAC CAG CCC<br>Arg Thr Val Asp Ser Ile Thr Leu Ser Trp Ser Gln Pro Asp Gln Pro<br>                435                        440                        445 | 1344 |
| AAT GGC GTG ATC CTG GAC TAT GAG CTG CAG TAC TAT GAG AAG GAG CTC<br>Asn Gly Val Ile Leu Asp Tyr Glu Leu Gln Tyr Tyr Glu Lys Glu Leu<br>450                        455                        460 | 1392 |
| AGT GAG TAC AAC GCC ACA GCC ATA AAA AGC CCC ACC AAC ACG GTC ACG<br>Ser Glu Tyr Asn Ala Thr Ala Ile Lys Ser Pro Thr Asn Thr Val Thr<br>465                        470                        475                        480 | 1440 |
| GGC CTC AAA GCC GGC GCC ATC TAT GTC TTC CAG GTG CGG GCA CGC ACT<br>Gly Leu Lys Ala Gly Ala Ile Tyr Val Phe Gln Val Arg Ala Arg Thr<br>                485                        490                        495 | 1488 |
| GTG GCA GGC TAC GGG CGC TAC AGC GGC AAG ATG TAC TTC CAG ACC ATG<br>Val Ala Gly Tyr Gly Arg Tyr Ser Gly Lys Met Tyr Phe Gln Thr Met<br>            500                        505                        510 | 1536 |
| ACA GAA GCC GAG TAC CAG ACA AGC ATC CAG GAG AAG TTG CCA CTC ATC<br>Thr Glu Ala Glu Tyr Gln Thr Ser Ile Gln Glu Lys Leu Pro Leu Ile<br>                515                        520                        525 | 1584 |
| ATC GGC TCC TCG GCC GCT GGC CTG GTC TTC CTC ATT GCT GTG GTT GTC<br>Ile Gly Ser Ser Ala Ala Gly Leu Val Phe Leu Ile Ala Val Val Val<br>            530                        535                        540 | 1632 |
| ATC GCC ATC GTG TGT AAC AGA CGG GGG TTT GAG CGT GCT GAC TCG GAG<br>Ile Ala Ile Val Cys Asn Arg Arg Gly Phe Glu Arg Ala Asp Ser Glu<br>545                        550                        555                        560 | 1680 |
| TAC ACG GAC AAG CTG CAA CAC TAC ACC AGT GGC CAC ATA ACC CCA GGC<br>Tyr Thr Asp Lys Leu Gln His Tyr Thr Ser Gly His Ile Thr Pro Gly<br>                565                        570                        575 | 1728 |
| ATG AAG ATC TAC ATC GAT CCT TTC ACC TAC GAG GAC CCC AAC GAG GCA<br>Met Lys Ile Tyr Ile Asp Pro Phe Thr Tyr Glu Asp Pro Asn Glu Ala<br>                    580                        585                        590 | 1776 |
| GTG CGG GAG TTT GCC AAG GAA ATT GAC ATC TCC TGT GTC AAA ATT GAG<br>Val Arg Glu Phe Ala Lys Glu Ile Asp Ile Ser Cys Val Lys Ile Glu<br>            595                        600                        605 | 1824 |

FIG. 1D

```
CAG GTG ATC GGA GCA GGG GAG TTT GGC GAG GTC TGC AGT GGC CAC CTG      1872
Gln Val Ile Gly Ala Gly Glu Phe Gly Glu Val Cys Ser Gly His Leu
    610             615                 620

AAG CTG CCA GGC AAG AGA GAG ATC TTT GTG GCC ATC AAG ACG CTC AAG      1920
Lys Leu Pro Gly Lys Arg Glu Ile Phe Val Ala Ile Lys Thr Leu Lys
625             630                 635                 640

TCG GGC TAC ACG GAG AAG CAG CGC CGG GAC TTC CTG AGC GAA GCC TCC      1968
Ser Gly Tyr Thr Glu Lys Gln Arg Arg Asp Phe Leu Ser Glu Ala Ser
                645                 650                 655

ATC ATG GGC CAG TTC GAC CAT CCC AAC GTC ATC CAC CTG GAG GGT GTC      2016
Ile Met Gly Gln Phe Asp His Pro Asn Val Ile His Leu Glu Gly Val
            660                 665                 670

GTG ACC AAG AGC ACA CCT GTG ATG ATC ATC ACC GAG TTC ATG GAG AAT      2064
Val Thr Lys Ser Thr Pro Val Met Ile Ile Thr Glu Phe Met Glu Asn
        675                 680                 685

GGC TCC CTG GAC TCC TTT CTC CGG CAA AAC GAT GGG CAG TTC ACA GTC      2112
Gly Ser Leu Asp Ser Phe Leu Arg Gln Asn Asp Gly Gln Phe Thr Val
690             695                 700

ATC CAG CTG GTG GGC ATG CTT CGG GGC ATC GCA GCT GGC ATG AAG TAC      2160
Ile Gln Leu Val Gly Met Leu Arg Gly Ile Ala Ala Gly Met Lys Tyr
705             710                 715                 720

CTG GCA GAC ATG AAC TAT GTT CAC CGT GAC CTG GCT GCC CGC AAC ATC      2208
Leu Ala Asp Met Asn Tyr Val His Arg Asp Leu Ala Ala Arg Asn Ile
                725                 730                 735

CTC GTC AAC AGC AAC CTG GTC TGC AAG GTG TCG GAC TTT GGG CTC TCA      2256
Leu Val Asn Ser Asn Leu Val Cys Lys Val Ser Asp Phe Gly Leu Ser
            740                 745                 750

CGC TTT CTA GAG GAC GAT ACC TCA GAC CCC ACC TAC ACC AGT GCC CTG      2304
Arg Phe Leu Glu Asp Asp Thr Ser Asp Pro Thr Tyr Thr Ser Ala Leu
        755                 760                 765

GGC GGA AAG TTC CCC ATC CGC TGG ACA GCC CCG GAA GCC ATC CAG TAC      2352
Gly Gly Lys Phe Pro Ile Arg Trp Thr Ala Pro Glu Ala Ile Gln Tyr
770             775                 780

CGG AAG TTC ACC TCG GCC AGT GAT GTG TGG AGC TAC GGC ATT GTC ATG      2400
Arg Lys Phe Thr Ser Ala Ser Asp Val Trp Ser Tyr Gly Ile Val Met
785             790                 795                 800

TGG GAG GTG ATG TCC TAT GGG GAG CGG CCC TAC TGG GAC ATG ACC AAC      2448
Trp Glu Val Met Ser Tyr Gly Glu Arg Pro Tyr Trp Asp Met Thr Asn
                805                 810                 815
```

FIG. IE

```
CAG GAT GTA ATC AAT GCC ATT GAG CAG GAC TAT CGG CTG CCA CCG CCC              2496
Gln Asp Val Ile Asn Ala Ile Glu Gln Asp Tyr Arg Leu Pro Pro Pro
            820             825                 830

ATG GAC TGC CCG AGC GCC CTG CAC CAA CTC ATG CTG GAC TGT TGG CAG              2544
Met Asp Cys Pro Ser Ala Leu His Gln Leu Met Leu Asp Cys Trp Gln
        835                 840                 845

AAG GAC CGC AAC CAC CGG CCC AAG TTC GGC CAA ATT GTC AAC ACG CTA              2592
Lys Asp Arg Asn His Arg Pro Lys Phe Gly Gln Ile Val Asn Thr Leu
        850                 855                 860

GAC AAG ATG ATC CGC AAT CCC AAC AGC CTC AAA GCC ATG GCG CCC CTC              2640
Asp Lys Met Ile Arg Asn Pro Asn Ser Leu Lys Ala Met Ala Pro Leu
865                 870                 875                 880

TCC TCT GGC ATC AAC CTG CCG CTG CTG GAC CGC ACG ATC CCC GAC TAC              2688
Ser Ser Gly Ile Asn Leu Pro Leu Leu Asp Arg Thr Ile Pro Asp Tyr
                885                 890                 895

ACC AGC TTT AAC ACG GTG GAC GAG TGG CTG GAG GCC ATC AAG ATG GGG              2736
Thr Ser Phe Asn Thr Val Asp Glu Trp Leu Glu Ala Ile Lys Met Gly
                900                 905                 910

CAG TAC AAG GAG AGC TTC GCC AAT GCC GGC TTC ACC TCC TTT GAC GTC              2784
Gln Tyr Lys Glu Ser Phe Ala Asn Ala Gly Phe Thr Ser Phe Asp Val
        915                 920                 925

GTG TCT CAG ATG ATG ATG GAG GAC ATT CTC CGG GTT GGG GTC ACT TTG              2832
Val Ser Gln Met Met Met Glu Asp Ile Leu Arg Val Gly Val Thr Leu
        930                 935                 940

GCT GGC CAC CAG AAA AAA ATC CTG AAC AGT ATC CAG GTG ATG CGG GCG              2880
Ala Gly His Gln Lys Lys Ile Leu Asn Ser Ile Gln Val Met Arg Ala
945                 950                 955                 960

CAG ATG AAC CAG ATT CAG TCT GTG GAG GTT TGACATTCAC CTGCCTCGGC                2930
Gln Met Asn Gln Ile Gln Ser Val Glu Val
                965                 970

TCACCTCTTC CTCCAAGCCC CGCCCCCTCT GC                                          2962
```

FIG. 2A

| | | | | | | | | | | | | | | | |
|---|---|---|---|---|---|---|---|---|---|---|---|---|---|---|---|
| CCA | GCG | TCC | CTG | GCC | GGC | TGC | TAC | TCT | GCA | CCT | CGA | CGG | GCT | CCC | CTC | 48 |
| Pro | Ala | Ser | Leu | Ala | Gly | Cys | Tyr | Ser | Ala | Pro | Arg | Arg | Ala | Pro | Leu | |
| 1 | | | | 5 | | | | | 10 | | | | | 15 | | |
| TGG | ACG | TGC | CTT | CTC | CTG | TGC | GCC | GCA | CTC | CGG | ACC | CTC | CTG | GCC | AGC | 96 |
| Trp | Thr | Cys | Leu | Leu | Leu | Cys | Ala | Ala | Leu | Arg | Thr | Leu | Leu | Ala | Ser | |
| | | | 20 | | | | | 25 | | | | | 30 | | | |
| CCC | AGC | AAC | GAA | GTG | AAT | TTA | TTG | GAT | TCA | CGC | ACT | GTC | ATG | GGG | GAC | 144 |
| Pro | Ser | Asn | Glu | Val | Asn | Leu | Leu | Asp | Ser | Arg | Thr | Val | Met | Gly | Asp | |
| | | 35 | | | | | 40 | | | | | 45 | | | | |
| CTG | GGA | TGG | ATT | GCT | TTT | CCA | AAA | AAT | GGG | TGG | GAA | GAG | ATT | GGT | GAA | 192 |
| Leu | Gly | Trp | Ile | Ala | Phe | Pro | Lys | Asn | Gly | Trp | Glu | Glu | Ile | Gly | Glu | |
| | 50 | | | | | 55 | | | | | 60 | | | | | |
| GTG | GAT | GAA | AAT | TAT | GCC | CCT | ATC | CAC | ACA | TAC | CAA | GTA | TGC | AAA | GTG | 240 |
| Val | Asp | Glu | Asn | Tyr | Ala | Pro | Ile | His | Thr | Tyr | Gln | Val | Cys | Lys | Val | |
| 65 | | | | | 70 | | | | | 75 | | | | | 80 | |
| ATG | GAA | CAG | AAT | CAG | AAT | AAC | TGG | CTT | TTG | ACC | AGT | TGG | ATC | TCC | AAT | 288 |
| Met | Glu | Gln | Asn | Gln | Asn | Asn | Trp | Leu | Leu | Thr | Ser | Trp | Ile | Ser | Asn | |
| | | | 85 | | | | | 90 | | | | | 95 | | | |
| GAA | GGT | GCT | TCC | AGA | ATC | TTC | ATA | GAA | CTC | AAA | TTT | ACC | CTG | CGG | GAC | 336 |
| Glu | Gly | Ala | Ser | Arg | Ile | Phe | Ile | Glu | Leu | Lys | Phe | Thr | Leu | Arg | Asp | |
| | | | 100 | | | | | 105 | | | | | 110 | | | |
| TGC | AAC | AGC | CTT | CCT | GGA | GGA | CTG | GGG | ACC | TGT | AAG | GAA | ACC | TTT | AAT | 384 |
| Cys | Asn | Ser | Leu | Pro | Gly | Gly | Leu | Gly | Thr | Cys | Lys | Glu | Thr | Phe | Asn | |
| | | 115 | | | | | 120 | | | | | 125 | | | | |
| ATG | TAT | TAC | TTT | GAG | TCA | GAT | GAT | CAG | AAT | GGG | AGA | AAC | ATC | AAG | GAA | 432 |
| Met | Tyr | Tyr | Phe | Glu | Ser | Asp | Asp | Gln | Asn | Gly | Arg | Asn | Ile | Lys | Glu | |
| | 130 | | | | | 135 | | | | | 140 | | | | | |
| AAC | CAA | TAC | ATC | AAA | ATT | GAT | ACC | ATT | GCT | GCC | GAT | GAA | AGC | TTT | ACA | 480 |
| Asn | Gln | Tyr | Ile | Lys | Ile | Asp | Thr | Ile | Ala | Ala | Asp | Glu | Ser | Phe | Thr | |
| 145 | | | | 150 | | | | | 155 | | | | | 160 | | |
| GAA | CTT | GAT | CTT | GGT | GAC | CGT | GTT | ATG | AAA | CTG | AAT | ACA | GAG | GTC | AGA | 528 |
| Glu | Leu | Asp | Leu | Gly | Asp | Arg | Val | Met | Lys | Leu | Asn | Thr | Glu | Val | Arg | |
| | | | 165 | | | | | 170 | | | | | 175 | | | |
| GAT | GTA | GGA | CCT | CTA | AGC | AAA | AAG | GGA | TTT | TAT | CTT | GCT | TTT | CAA | GAT | 576 |
| Asp | Val | Gly | Pro | Leu | Ser | Lys | Lys | Gly | Phe | Tyr | Leu | Ala | Phe | Gln | Asp | |
| | | | 180 | | | | | 185 | | | | | 190 | | | |
| GTT | GGT | GCT | TGC | ATT | GCT | CTG | GTT | TCT | GTG | CGT | GTA | TAC | TAT | AAA | AAA | 624 |
| Val | Gly | Ala | Cys | Ile | Ala | Leu | Val | Ser | Val | Arg | Val | Tyr | Tyr | Lys | Lys | |
| | | 195 | | | | | 200 | | | | | 205 | | | | |

FIG. 2B

| | | | | | | | | | | | | | | |
|---|---|---|---|---|---|---|---|---|---|---|---|---|---|---|
| TGC | CCT | TCT | GTG | GTA | CGA | CAC | TTG | GCT | GTC | TTC | CCT | GAC | ACC | ATC | ACT | 672 |
| Cys | Pro | Ser | Val | Val | Arg | His | Leu | Ala | Val | Phe | Pro | Asp | Thr | Ile | Thr |
| | 210 | | | | 215 | | | | | 220 | | | | |

GGA GCT GAT TCT TCC CAA TTG CTC GAA GTG TCG GGC TCC TGT GTC AAC    720
Gly Ala Asp Ser Ser Gln Leu Leu Glu Val Ser Gly Ser Cys Val Asn
225              230                  235                  240

CAT TCT GTG ACC GAT GAA CCT CCC AAA ATG CAC TGC AGC GCC GAA GGG    768
His Ser Val Thr Asp Glu Pro Pro Lys Met His Cys Ser Ala Glu Gly
                245              250                  255

GAG TGG CTG GTG CCC ATC GGG AAA TGC ATG TGC AAG GCA GGA TAT GAA    816
Glu Trp Leu Val Pro Ile Gly Lys Cys Met Cys Lys Ala Gly Tyr Glu
            260                  265                  270

GAG AAA AAT GGC ACC TGT CAA GTG TGC AGA CCT GGG TTC TTC AAA GCC    864
Glu Lys Asn Gly Thr Cys Gln Val Cys Arg Pro Gly Phe Phe Lys Ala
        275                  280                  285

TCA CCT CAC ATC CAG AGC TGC GGC AAA TGT CCA CCT CAC AGT TAT ACC    912
Ser Pro His Ile Gln Ser Cys Gly Lys Cys Pro Pro His Ser Tyr Thr
    290                  295                  300

CAT GAG GAA GCT TCA ACC TCT TGT GTC TGT GAA AAG GAT TAT TTC AGG    960
His Glu Glu Ala Ser Thr Ser Cys Val Cys Glu Lys Asp Tyr Phe Arg
305              310                  315                  320

AGA GAG TCT GAT CCA CCC ACA ATG GCA TGC ACA AGA CCC CCC TCT GCT    1008
Arg Glu Ser Asp Pro Pro Thr Met Ala Cys Thr Arg Pro Pro Ser Ala
            325                  330                  335

CCT CGG AAT GCC ATC TCA AAT GTT AAT GAA ACT AGT GTC TTT CTG GAA    1056
Pro Arg Asn Ala Ile Ser Asn Val Asn Glu Thr Ser Val Phe Leu Glu
        340                  345                  350

TGG ATT CCG CCT GCT GAC ACT GGT GGA AGG AAA GAC GTG TCA TAT TAT    1104
Trp Ile Pro Pro Ala Asp Thr Gly Gly Arg Lys Asp Val Ser Tyr Tyr
    355                  360                  365

ATT GCA TGC AAG AAG TGC AAC TCC CAT GCA GGT GTG TGT GAG GAG TGT    1152
Ile Ala Cys Lys Lys Cys Asn Ser His Ala Gly Val Cys Glu Glu Cys
370                  375                  380

GGC GGT CAT GTC AGG TAC CTT CCC CGG CAA AGC GGC CTG AAA AAC ACC    1200
Gly Gly His Val Arg Tyr Leu Pro Arg Gln Ser Gly Leu Lys Asn Thr
385              390                  395                  400

TCT GTC ATG ATG GTG GAT CTA CTC GCT CAC ACA AAC TAT ACC TTT GAG    1248
Ser Val Met Met Val Asp Leu Leu Ala His Thr Asn Tyr Thr Phe Glu
            405                  410                  415

FIG. 2C

```
ATT GAG GCA GTG AAT GGA GTG TCC GAC TTG AGC CCA GGA GCC CGG CAG    1296
Ile Glu Ala Val Asn Gly Val Ser Asp Leu Ser Pro Gly Ala Arg Gln
            420                 425                 430

TAT GTG TCT GTA AAT GTA ACC ACA AAT CAA GCA GCT CCA TCT CCA GTC    1344
Tyr Val Ser Val Asn Val Thr Thr Asn Gln Ala Ala Pro Ser Pro Val
            435                 440                 445

ACC AAT GTG AAA AAA GGG AAA ATT GCA AAA AAC AGC ATC TCT TTG TCT    1392
Thr Asn Val Lys Lys Gly Lys Ile Ala Lys Asn Ser Ile Ser Leu Ser
            450                 455                 460

TGG CAA GAA CCA GAT CGT CCC AAT GGA ATC ATC CTA GAG TAT GAA ATC    1440
Trp Gln Glu Pro Asp Arg Pro Asn Gly Ile Ile Leu Glu Tyr Glu Ile
465                 470                 475                 480

AAG CAT TTT GAA AAG GAC CAA GAG ACC AGC TAC ACG ATT ATC AAA TCT    1488
Lys His Phe Glu Lys Asp Gln Glu Thr Ser Tyr Thr Ile Ile Lys Ser
                    485                 490                 495

AAA GAG ACA ACT ATT ACT GCA GAG GGC TTG AAA CCA GCT TCA GTT TAT    1536
Lys Glu Thr Thr Ile Thr Ala Glu Gly Leu Lys Pro Ala Ser Val Tyr
                500                 505                 510

GTC TTC CAA ATT CGA GCA CGT ACA GCA GCA GGC TAT GGT GTC TTC AGT    1584
Val Phe Gln Ile Arg Ala Arg Thr Ala Ala Gly Tyr Gly Val Phe Ser
            515                 520                 525

CGA AGA TTT GAG TTT GAA ACC ACC CCA GTG TTT GCA GCA TCC AGC GAT    1632
Arg Arg Phe Glu Phe Glu Thr Thr Pro Val Phe Ala Ala Ser Ser Asp
            530                 535                 540

CAA AGC CAG ATT CCT GTA ATT GCT GTG TCT GTG ACA GTA GGA GTC ATT    1680
Gln Ser Gln Ile Pro Val Ile Ala Val Ser Val Thr Val Gly Val Ile
545                 550                 555                 560

TTG TTG GCA GTG GTT ATC GGC GTC CTC CTC AGT GGA AGG CGG TGT GGC    1728
Leu Leu Ala Val Val Ile Gly Val Leu Leu Ser Gly Arg Arg Cys Gly
                565                 570                 575

TAC AGC AAA GCA AAA CAA GAT CCA GAA GAG GAA AAG ATG CAT TTT CAT    1776
Tyr Ser Lys Ala Lys Gln Asp Pro Glu Glu Glu Lys Met His Phe His
            580                 585                 590

AAT GGG CAC ATT AAA CTG CCA GGA GTA AGA ACT TAC ATT GAT CCA CAT    1824
Asn Gly His Ile Lys Leu Pro Gly Val Arg Thr Tyr Ile Asp Pro His
            595                 600                 605

ACC TAT GAG GAT CCC AAT CAA GCT GTC CAC GAA TTT GCC AAG GAG ATA    1872
Thr Tyr Glu Asp Pro Asn Gln Ala Val His Glu Phe Ala Lys Glu Ile
610                 615                 620
```

FIG. 2D

```
GAA GCA TCA TGT ATC ACC ATT GAG AGA GTT ATT GGA GCA GGT GAA TTT       1920
Glu Ala Ser Cys Ile Thr Ile Glu Arg Val Ile Gly Ala Gly Glu Phe
625             630             635             640

GGT GAA GTT TGT AGT GGA CGT TTG AAA CTA CCA GGA AAA AGA GAA TTA       1968
Gly Glu Val Cys Ser Gly Arg Leu Lys Leu Pro Gly Lys Arg Glu Leu
            645             650             655

CCT GTG GCT ATC AAA ACC CTT AAA GTA GGC TAT ACT GAA AAG CAA CGC       2016
Pro Val Ala Ile Lys Thr Leu Lys Val Gly Tyr Thr Glu Lys Gln Arg
                660             665             670

AGA GAT TTC CTA GGT GAA GCA AGT ATC ATG GGA CAG TTT GAT CAT CCT       2064
Arg Asp Phe Leu Gly Glu Ala Ser Ile Met Gly Gln Phe Asp His Pro
            675             680             685

AAC ATC ATC CAT TTA GAA GGT GTG GTG ACC AAA AGT AAA CCA GTG ATG       2112
Asn Ile Ile His Leu Glu Gly Val Val Thr Lys Ser Lys Pro Val Met
690             695             700

ATC GTG ACA GAG TAT ATG GAG AAT GGC TCT TTA GAT ACA TTT TTG AAG       2160
Ile Val Thr Glu Tyr Met Glu Asn Gly Ser Leu Asp Thr Phe Leu Lys
705             710             715             720

AAA AAC GAT GGG CAG TTC ACT GTG ATT CAG CTT GTT GGC ATG CTG AGA       2208
Lys Asn Asp Gly Gln Phe Thr Val Ile Gln Leu Val Gly Met Leu Arg
                725             730             735

GGT ATC TCT GCA GGA ATG AAG TAC CTT TCT GAC ATG GGC TAT GTG CAT       2256
Gly Ile Ser Ala Gly Met Lys Tyr Leu Ser Asp Met Gly Tyr Val His
            740             745             750

AGA GAT CTT GCT GCC AGA AAC ATC TTA ATC AAC AGT AAC CTT GTG TGC       2304
Arg Asp Leu Ala Ala Arg Asn Ile Leu Ile Asn Ser Asn Leu Val Cys
        755             760             765

AAA GTG TCT GAC TTT GGA CTT TCC CGG GTA CTG GAA GAT GAT CCC GAG       2352
Lys Val Ser Asp Phe Gly Leu Ser Arg Val Leu Glu Asp Asp Pro Glu
770             775             780

GCA GCC TAC ACC ACA AGG GGA GGA AAA ATT CCA ATC AGA TGG ACT GCC       2400
Ala Ala Tyr Thr Thr Arg Gly Gly Lys Ile Pro Ile Arg Trp Thr Ala
785             790             795             800

CCA GAA GCA ATA GCT TTC CGA AAG TTT ACT TCT GCC AGT GAT GTC TGG       2448
Pro Glu Ala Ile Ala Phe Arg Lys Phe Thr Ser Ala Ser Asp Val Trp
                805             810             815

AGT TAT GGA ATA GTA ATG TGG GAA GTT GTG TCT TAT GGA GAG AGA CCC       2496
Ser Tyr Gly Ile Val Met Trp Glu Val Val Ser Tyr Gly Glu Arg Pro
            820             825             830
```

FIG. 2E

| | |
|---|---|
| TAC TGG GAG ATG ACC AAT CAA GAT GTG ATT AAA GCG GTA GAG GAA GGC<br>Tyr Trp Glu Met Thr Asn Gln Asp Val Ile Lys Ala Val Glu Glu Gly<br>835 840 845 | 2544 |
| TAT CGT CTG CCA AGC CCC ATG GAT TGT CCT GCT GCT CTC TAT CAG TTA<br>Tyr Arg Leu Pro Ser Pro Met Asp Cys Pro Ala Ala Leu Tyr Gln Leu<br>850 855 860 | 2592 |
| ATG CTG GAT TGC TGG CAG AAA GAG CGA AAT AGC AGG CCC AAG TTT GAT<br>Met Leu Asp Cys Trp Gln Lys Glu Arg Asn Ser Arg Pro Lys Phe Asp<br>865 870 875 880 | 2640 |
| GAA ATA GTC AAC ATG TTG GAC AAG CTG ATA CGT AAC CCA AGT AGT CTG<br>Glu Ile Val Asn Met Leu Asp Lys Leu Ile Arg Asn Pro Ser Ser Leu<br>885 890 895 | 2688 |
| AAG ACG CTG GTT AAT GCA TCC TGC AGA GTA TCT AAT TTA TTG GCA GAA<br>Lys Thr Leu Val Asn Ala Ser Cys Arg Val Ser Asn Leu Leu Ala Glu<br>900 905 910 | 2736 |
| CAT AGC CCA CTA GGA TCT GGG GCC TAC AGA TCA GTA GGT GAA TGG CTA<br>His Ser Pro Leu Gly Ser Gly Ala Tyr Arg Ser Val Gly Glu Trp Leu<br>915 920 925 | 2784 |
| GAG GCA ATC AAG ATG GGC CGG TAT ACA GAG ATT TTC ATG GAA AAT GGA<br>Glu Ala Ile Lys Met Gly Arg Tyr Thr Glu Ile Phe Met Glu Asn Gly<br>930 935 940 | 2832 |
| TAC AGT TCA ATG GAC GCT GTG GCT CAG GTG ACC TTG GAG GAT TTG AGA<br>Tyr Ser Ser Met Asp Ala Val Ala Gln Val Thr Leu Glu Asp Leu Arg<br>945 950 955 960 | 2880 |
| CGG CTT GGA GTG ACT CTT GTC GGT CAC CAG AAG AAG ATC ATG AAC AGC<br>Arg Leu Gly Val Thr Leu Val Gly His Gln Lys Lys Ile Met Asn Ser<br>965 970 975 | 2928 |
| CTT CAA GAA ATG AAG GTG CAG CTG GTA AAC GGA ATG GTG CCA TTG TAACTTCATG<br>Leu Gln Glu Met Lys Val Gln Leu Val Asn Gly Met Val Pro Leu<br>980 985 990 | 2983 |
| TAAATGTCGC TTCTTCAAGT GAATGATTCT GCACTTTGTA AACAGCACTG AGATTTATTT | 3043 |
| TAACAAAAAA AGGGGGAAAA GGGAAAACAG TGATTTCTAA ACCTTAGAAA ACATTTGCCT | 3103 |
| CAGCCACAGA ATTTGTAATC ATGGTTTTAC TGAAGTATCC AGTTCTTAGT CCTTAGTCT | 3162 |

FIG. 3A

| | | |
|---|---|---|
| AAGCGGCAGG AGCAGCGTTG GCACCGGCGA ACC ATG GCT GGG ATT TTC TAT TTC<br>Met Ala Gly Ile Phe Tyr Phe<br>1 5 | 54 |

GCC CTA TTT TCG TGT CTC TTC GGG ATT TGC GAC GCT GTC ACA GGT TCC     102
Ala Leu Phe Ser Cys Leu Phe Gly Ile Cys Asp Ala Val Thr Gly Ser
        10              15                  20

AGG GTA TAC CCC GCG AAT GAA GTT ACC TTA TTG GAT TCC AGA TCT GTT     150
Arg Val Tyr Pro Ala Asn Glu Val Thr Leu Leu Asp Ser Arg Ser Val
    25                  30                  35

CAG GGA GAA CTT GGG TGG ATA GCA AGC CCT CTG GAA GGA GGG TGG GAG     198
Gln Gly Glu Leu Gly Trp Ile Ala Ser Pro Leu Glu Gly Gly Trp Glu
40                  45                  50                  55

GAA GTG AGT ATC ATG GAT GAA AAA AAT ACA CCA ATC CGA ACC TAC CAA     246
Glu Val Ser Ile Met Asp Glu Lys Asn Thr Pro Ile Arg Thr Tyr Gln
            60                  65                  70

GTG TGC AAT GTG ATG GAA CCC AGC CAG AAT AAC TGG CTA CGA ACT GAT     294
Val Cys Asn Val Met Glu Pro Ser Gln Asn Asn Trp Leu Arg Thr Asp
                75                  80                  85

TGG ATC ACC CGA GAA GGG GCT CAG AGG GTG TAT ATT GAG ATT AAA TTC     342
Trp Ile Thr Arg Glu Gly Ala Gln Arg Val Tyr Ile Glu Ile Lys Phe
            90                  95                  100

ACC TTG AGG GAC TGC AAT AGT CTT CCG GGC GTC ATG GGG ACT TGC AAG     390
Thr Leu Arg Asp Cys Asn Ser Leu Pro Gly Val Met Gly Thr Cys Lys
    105                 110                 115

GAG ACG TTT AAC CTG TAC TAC TAT GAA TCA GAC AAC GAC AAA GAG CGT     438
Glu Thr Phe Asn Leu Tyr Tyr Tyr Glu Ser Asp Asn Asp Lys Glu Arg
120                 125                 130                 135

TTC ATC AGA GAG AAC CAG TTT GTC AAA ATT GAC ACC ATT GCT GCT GAT     486
Phe Ile Arg Glu Asn Gln Phe Val Lys Ile Asp Thr Ile Ala Ala Asp
                140                 145                 150

GAG AGC TTC ACC CAA GTG GAC ATT GGT GAC AGA ATC ATG AAG CTG AAC     534
Glu Ser Phe Thr Gln Val Asp Ile Gly Asp Arg Ile Met Lys Leu Asn
            155                 160                 165

ACC GAG ATC CGG GAT GTA GGG CCA TTA AGC AAA AAG GGG TTT TAC CTG     582
Thr Glu Ile Arg Asp Val Gly Pro Leu Ser Lys Lys Gly Phe Tyr Leu
        170                 175                 180

FIG. 3B

```
GCT TTT CAG GAT GTG GGG GCC TGC ATC GCC CTG GTA TCA GTC CGT GTG        630
Ala Phe Gln Asp Val Gly Ala Cys Ile Ala Leu Val Ser Val Arg Val
    185             190                 195

TTC TAT AAA AAG TGT CCA CTC ACA GTC CGC AAT CTG GCC CAG TTT CCT        678
Phe Tyr Lys Lys Cys Pro Leu Thr Val Arg Asn Leu Ala Gln Phe Pro
200             205                 210                 215

GAC ACC ATC ACA GGG GCT GAT ACG TCT TCC CTG GTG GAA GTT CGA GGC        726
Asp Thr Ile Thr Gly Ala Asp Thr Ser Ser Leu Val Glu Val Arg Gly
                220                 225                 230

TCC TGT GTC AAC AAC TCA GAA GAG AAA GAT GTG CCA AAA ATG TAC TGT        774
Ser Cys Val Asn Asn Ser Glu Glu Lys Asp Val Pro Lys Met Tyr Cys
            235                 240                 245

GGG GCA GAT GGT GAA TGG CTG GTA CCC ATT GGC AAC TGC CTA TGC AAC        822
Gly Ala Asp Gly Glu Trp Leu Val Pro Ile Gly Asn Cys Leu Cys Asn
        250                 255                 260

GCT GGG CAT GAG GAG CGG AGC GGA GAA TGC CAA GCT TGC AAA ATT GGA        870
Ala Gly His Glu Glu Arg Ser Gly Glu Cys Gln Ala Cys Lys Ile Gly
    265                 270                 275

TAT TAC AAG GCT CTC TCC ACG GAT GCC ACC TGT GCC AAG TGC CCA CCC        918
Tyr Tyr Lys Ala Leu Ser Thr Asp Ala Thr Cys Ala Lys Cys Pro Pro
280             285                 290                 295

CAC AGC TAC TCT GTC TGG GAA GGA GCC ACC TCG TGC ACC TGT GAC CGA        966
His Ser Tyr Ser Val Trp Glu Gly Ala Thr Ser Cys Thr Cys Asp Arg
                300                 305                 310

GGC TTT TTC AGA GCT GAC AAC GAT GCT GCC TCT ATG CCC TGC ACC CGT       1014
Gly Phe Phe Arg Ala Asp Asn Asp Ala Ala Ser Met Pro Cys Thr Arg
            315                 320                 325

CCA CCA TCT GCT CCC CTG AAC TTG ATT TCA AAT GTC AAC GAG ACA TCT       1062
Pro Pro Ser Ala Pro Leu Asn Leu Ile Ser Asn Val Asn Glu Thr Ser
        330                 335                 340

GTG AAC TTG GAA TGG AGT AGC CCT CAG AAT ACA GGT GGC CGC CAG GAC       1110
Val Asn Leu Glu Trp Ser Ser Pro Gln Asn Thr Gly Gly Arg Gln Asp
    345                 350                 355

ATT TCC TAT AAT GTG GTA TGC AAG AAA TGT GGA GCT GGT GAC CCC AGC       1158
Ile Ser Tyr Asn Val Val Cys Lys Lys Cys Gly Ala Gly Asp Pro Ser
360             365                 370                 375

AAG TGC CGA CCC TGT GGA AGT GGG GTC CAC TAC ACC CCA CAG CAG AAT       1206
Lys Cys Arg Pro Cys Gly Ser Gly Val His Tyr Thr Pro Gln Gln Asn
                380                 385                 390
```

FIG. 3C

```
GGC TTG AAG ACC ACC AAA GTC TCC ATC ACT GAC CTC CTA GCT CAT ACC         1254
Gly Leu Lys Thr Thr Lys Val Ser Ile Thr Asp Leu Leu Ala His Thr
            395             400             405

AAT TAC ACC TTT GAA ATC TGG GCT GTG AAT GGA GTG TCC AAA TAT AAC         1302
Asn Tyr Thr Phe Glu Ile Trp Ala Val Asn Gly Val Ser Lys Tyr Asn
            410             415             420

CCT AAC CCA GAC CAA TCA GTT TCT GTC ACT GTG ACC ACC AAC CAA GCA         1350
Pro Asn Pro Asp Gln Ser Val Ser Val Thr Val Thr Thr Asn Gln Ala
            425             430             435

GCA CCA TCA TCC ATT GCT TTG GTC CAG GCT AAA GAA GTC ACA AGA TAC         1398
Ala Pro Ser Ser Ile Ala Leu Val Gln Ala Lys Glu Val Thr Arg Tyr
440             445             450             455

AGT GTG GCA CTG GCT TGG CTG GAA CCA GAT CGG CCC AAT GGG GTA ATC         1446
Ser Val Ala Leu Ala Trp Leu Glu Pro Asp Arg Pro Asn Gly Val Ile
            460             465             470

CTG GAA TAT GAA GTC AAG TAT TAT GAG AAG GAT CAG AAT GAG CGA AGC         1494
Leu Glu Tyr Glu Val Lys Tyr Tyr Glu Lys Asp Gln Asn Glu Arg Ser
            475             480             485

TAT CGT ATA GTT CGG ACA GCT GCC AGG AAC ACA GAT ATC AAA GGC CTG         1542
Tyr Arg Ile Val Arg Thr Ala Ala Arg Asn Thr Asp Ile Lys Gly Leu
            490             495             500

AAC CCT CTC ACT TCC TAT GTT TTC CAC GTG CGA GCC AGG ACA GCA GCT         1590
Asn Pro Leu Thr Ser Tyr Val Phe His Val Arg Ala Arg Thr Ala Ala
505             510             515

GGC TAT GGA GAC TTC AGT GAG CCC TTG GAG GTT ACA ACC AAC ACA GTG         1638
Gly Tyr Gly Asp Phe Ser Glu Pro Leu Glu Val Thr Thr Asn Thr Val
520             525             530             535

CCT TCC CGG ATC ATT GGA GAT GGG GCT AAC TCC ACA GTC CTT CTG GTC         1686
Pro Ser Arg Ile Ile Gly Asp Gly Ala Asn Ser Thr Val Leu Leu Val
            540             545             550

TCT GTC TCG GGC AGT GTG GTG CTG GTG GTA ATT CTC ATT GCA GCT TTT         1734
Ser Val Ser Gly Ser Val Val Leu Val Val Ile Leu Ile Ala Ala Phe
            555             560             565

GTC ATC AGC CGG AGA CGG AGT AAA TAC AGT AAA GCC AAA CAA GAA GCG         1782
Val Ile Ser Arg Arg Arg Ser Lys Tyr Ser Lys Ala Lys Gln Glu Ala
            570             575             580

GAT GAA GAG AAA CAT TTG AAT CAA GGT GTA AGA ACA TAT GTG GAC CCC         1830
Asp Glu Glu Lys His Leu Asn Gln Gly Val Arg Thr Tyr Val Asp Pro
585             590             595
```

FIG. 3D

```
TTT ACG TAC GAA GAT CCC AAC CAA GCA GTG CGA GAG TTT GCC AAA GAA        1878
Phe Thr Tyr Glu Asp Pro Asn Gln Ala Val Arg Glu Phe Ala Lys Glu
600             605             610             615

ATT GAC GCA TCC TGC ATT AAG ATT GAA AAA GTT ATA GGA GTT GGT GAA        1926
Ile Asp Ala Ser Cys Ile Lys Ile Glu Lys Val Ile Gly Val Gly Glu
                620             625             630

TTT GGT GAG GTA TGC AGT GGG CGT CTC AAA GTG CCT GGC AAG AGA GAG        1974
Phe Gly Glu Val Cys Ser Gly Arg Leu Lys Val Pro Gly Lys Arg Glu
            635             640             645

ATC TGT GTG GCT ATC AAG ACT CTG AAA GCT GGT TAT ACA GAC AAA CAG        2022
Ile Cys Val Ala Ile Lys Thr Leu Lys Ala Gly Tyr Thr Asp Lys Gln
        650             655             660

AGG AGA GAC TTC CTG AGT GAG GCC AGC ATC ATG GGA CAG TTT GAC CAT        2070
Arg Arg Asp Phe Leu Ser Glu Ala Ser Ile Met Gly Gln Phe Asp His
665             670             675

CCG AAC ATC ATT CAC TTG GAA GGC GTG GTC ACT AAA TGT AAA CCA GTA        2118
Pro Asn Ile Ile His Leu Glu Gly Val Val Thr Lys Cys Lys Pro Val
680             685             690             695

ATG ATC ATA ACA GAG TAC ATG GAG AAT GGC TCC TTG GAT GCA TTC CTC        2166
Met Ile Ile Thr Glu Tyr Met Glu Asn Gly Ser Leu Asp Ala Phe Leu
            700             705             710

AGG AAA AAT GAT GGC AGA TTT ACA GTC ATT CAG CTG GTG GGC ATG CTT        2214
Arg Lys Asn Asp Gly Arg Phe Thr Val Ile Gln Leu Val Gly Met Leu
        715             720             725

CGT GGC ATT GGG TCT GGG ATG AAG TAT TTA TCT GAT ATG AGC TAT GTG        2262
Arg Gly Ile Gly Ser Gly Met Lys Tyr Leu Ser Asp Met Ser Tyr Val
        730             735             740

CAT CGT GAT CTG GCC GCA CGG AAC ATC CTG GTG AAC AGC AAC TTG GTC        2310
His Arg Asp Leu Ala Ala Arg Asn Ile Leu Val Asn Ser Asn Leu Val
    745             750             755

TGC AAA GTG TCT GAT TTT GGC ATG TCC CGA GTG CTT GAG GAT GAT CCG        2358
Cys Lys Val Ser Asp Phe Gly Met Ser Arg Val Leu Glu Asp Asp Pro
760             765             770             775

GAA GCA GCT TAC ACC ACC AGG GGT GGC AAG ATT CCT ATC CGG TGG ACT        2406
Glu Ala Ala Tyr Thr Thr Arg Gly Gly Lys Ile Pro Ile Arg Trp Thr
                780             785             790

GCG CCA GAA GCA ATT GCC TAT CGT AAA TTC ACA TCA GCA AGT GAT GTA        2454
Ala Pro Glu Ala Ile Ala Tyr Arg Lys Phe Thr Ser Ala Ser Asp Val
            795             800             805
```

FIG. 3E

```
TGG AGC TAT GGA ATC GTT ATG TGG GAA GTG ATG TCG TAC GGG GAG AGG       2502
Trp Ser Tyr Gly Ile Val Met Trp Glu Val Met Ser Tyr Gly Glu Arg
        810                 815                 820

CCC TAT TGG GAT ATG TCC AAT CAA GAT GTG ATT AAA GCC ATT GAG GAA       2550
Pro Tyr Trp Asp Met Ser Asn Gln Asp Val Ile Lys Ala Ile Glu Glu
        825                 830                 835

GGC TAT CGG TTA CCC CCT CCA ATG GAC TGC CCC ATT GCG CTC CAC CAG       2598
Gly Tyr Arg Leu Pro Pro Pro Met Asp Cys Pro Ile Ala Leu His Gln
840                 845                 850                 855

CTG ATG CTA GAC TGC TGG CAG AAG GAG AGG AGC GAC AGG CCT AAA TTT       2646
Leu Met Leu Asp Cys Trp Gln Lys Glu Arg Ser Asp Arg Pro Lys Phe
                860                 865                 870

GGG CAG ATT GTC AAC ATG TTG GAC AAA CTC ATC CGC AAC CCC AAC AGC       2694
Gly Gln Ile Val Asn Met Leu Asp Lys Leu Ile Arg Asn Pro Asn Ser
                875                 880                 885

TTG AAG AGG ACA GGG ACG GAG AGC TCC AGA CCT AAC ACT GCC TTG TTG       2742
Leu Lys Arg Thr Gly Thr Glu Ser Ser Arg Pro Asn Thr Ala Leu Leu
        890                 895                 900

GAT CCA AGC TCC CCT GAA TTC TCT GCT GTG GTA TCA GTG GGC GAT TGG       2790
Asp Pro Ser Ser Pro Glu Phe Ser Ala Val Val Ser Val Gly Asp Trp
        905                 910                 915

CTC CAG GCC ATT AAA ATG GAC CGG TAT AAG GAT AAC TTC ACA GCT GCT       2838
Leu Gln Ala Ile Lys Met Asp Arg Tyr Lys Asp Asn Phe Thr Ala Ala
920                 925                 930                 935

GGT TAT ACC ACA CTA GAG GCT GTG GTC CAC GTG AAC CAG GAG GAC CTG       2886
Gly Tyr Thr Thr Leu Glu Ala Val Val His Val Asn Gln Glu Asp Leu
                940                 945                 950

GCA AGA ATT GGT ATC ACA GCC ATC ACG CAC CAG AAT AAG ATT TTG AGC       2934
Ala Arg Ile Gly Ile Thr Ala Ile Thr His Gln Asn Lys Ile Leu Ser
                955                 960                 965

AGT GTC CAG GCA ATG CGA ACC CAA ATG CAG CAG ATG CAC GGC AGA ATG       2982
Ser Val Gln Ala Met Arg Thr Gln Met Gln Gln Met His Gly Arg Met
        970                 975                 980

GTT CCC GTC TGAGCCAGTA CTGAATAAAC TCAAAACTCT TGAAATTAGT               3031
Val Pro Val
        985

TTACCTCATC CATGCACTTT AATTGAAGAA CTGCACTTTT TTTACTTCGT CTTCGCCCTC     3091

TGAAATTAAA GAAATGAAAA AAAAA                                           3116
```

FIG. 4A

```
CGGTGCGAGC GAACAGGAGT GGGGGGGAAA TTAAAAAAAG CTAAACGTGG AGCAGCCGAT      60

CGGGGACCGA GAAGGGGAAT CGATGCAAGG AGCACACTAA AACAAAAGCT ACTTCGGAAC     120

AAACAGCATT TAAAAATCCA CGACTCAAGA TAACTGAAAC CTAAAATAAA ACCTGCTCAT     180

GCACC ATG GTT TTT CAA ACT CGG TAC CCT TCA TGG ATT ATT TTA TGC        227
      Met Val Phe Gln Thr Arg Tyr Pro Ser Trp Ile Ile Leu Cys
       1               5                  10

TAC ATC TGG CTG CTC CGC TTT GCA CAC ACA GGG GAG GCG CAG GCT GCG      275
Tyr Ile Trp Leu Leu Arg Phe Ala His Thr Gly Glu Ala Gln Ala Ala
 15                  20                  25                  30

AAG GAA GTA CTA CTG CTG GAT TCT AAA GCA CAA CAA ACA GAG TTG GAG      323
Lys Glu Val Leu Leu Leu Asp Ser Lys Ala Gln Gln Thr Glu Leu Glu
                 35                  40                  45

TGG ATT TCC TCT CCA CCC AAT GGG TGG GAA GAA ATT AGT GGT TTG GAT      371
Trp Ile Ser Ser Pro Pro Asn Gly Trp Glu Glu Ile Ser Gly Leu Asp
             50                  55                  60

GAG AAC TAT ACC CCG ATA CGA ACA TAC CAG GTG TGC CAA GTC ATG GAG      419
Glu Asn Tyr Thr Pro Ile Arg Thr Tyr Gln Val Cys Gln Val Met Glu
         65                  70                  75

CCC AAC CAA AAC AAC TGG CTG CGG ACT AAC TGG ATT TCC AAA GGC AAT      467
Pro Asn Gln Asn Asn Trp Leu Arg Thr Asn Trp Ile Ser Lys Gly Asn
     80                  85                  90

GCA CAA AGG ATT TTT GTA GAA TTG AAA TTC ACC CTG AGG GAT TGT AAC      515
Ala Gln Arg Ile Phe Val Glu Leu Lys Phe Thr Leu Arg Asp Cys Asn
 95                 100                 105                 110

AGT CTT CCT GGA GTA CTG GGA ACT TGC AAG GAA ACA TTT AAT TTG TAC      563
Ser Leu Pro Gly Val Leu Gly Thr Cys Lys Glu Thr Phe Asn Leu Tyr
                115                 120                 125

TAT TAT GAA ACA GAC TAT GAC ACT GGC AGG AAT ATA AGA GAA AAC CTC      611
Tyr Tyr Glu Thr Asp Tyr Asp Thr Gly Arg Asn Ile Arg Glu Asn Leu
            130                 135                 140

TAT GTA AAA ATA GAC ACC ATT GCT GCA GAT GAA AGT TTT ACC CAA GGT      659
Tyr Val Lys Ile Asp Thr Ile Ala Ala Asp Glu Ser Phe Thr Gln Gly
        145                 150                 155

GAC CTT GGT GAA AGA AAG ATG AAG CTT AAC ACT GAG GTG AGA GAG ATT      707
Asp Leu Gly Glu Arg Lys Met Lys Leu Asn Thr Glu Val Arg Glu Ile
    160                 165                 170
```

FIG. 4B

| | | | | | | | | | | | | | | |
|---|---|---|---|---|---|---|---|---|---|---|---|---|---|---|
| GGA | CCT | TTG | TCC | AAA | AAG | GGA | TTC | TAT | CTT | GCC | TTT | CAG | GAT | GTA | GGG | 755 |
| Gly | Pro | Leu | Ser | Lys | Lys | Gly | Phe | Tyr | Leu | Ala | Phe | Gln | Asp | Val | Gly |
| 175 | | | | 180 | | | | | 185 | | | | | | 190 |

| GCT | TGC | ATA | GCT | TTG | GTT | TCT | GTC | AAA | GTG | TAC | TAC | AAG | AAG | TGC | TGG | 803 |
| Ala | Cys | Ile | Ala | Leu | Val | Ser | Val | Lys | Val | Tyr | Tyr | Lys | Lys | Cys | Trp |
| | | | | 195 | | | | | 200 | | | | | 205 | |

| TCC | ATT | ATT | GAG | AAC | TTA | GCT | ATC | TTT | CCA | GAT | ACA | GTG | ACT | GGT | TCA | 851 |
| Ser | Ile | Ile | Glu | Asn | Leu | Ala | Ile | Phe | Pro | Asp | Thr | Val | Thr | Gly | Ser |
| | | | 210 | | | | | 215 | | | | 220 | | | |

| GAA | TTT | TCC | TCT | TTA | GTC | GAG | GTT | CGA | GGG | ACA | TGT | GTC | AGC | AGT | GCA | 899 |
| Glu | Phe | Ser | Ser | Leu | Val | Glu | Val | Arg | Gly | Thr | Cys | Val | Ser | Ser | Ala |
| | | 225 | | | | | 230 | | | | | 235 | | | |

| GAG | GAA | GAA | GCG | GAA | AAC | GCC | CCC | AGG | ATG | CAC | TGC | AGT | GCA | GAA | GGA | 947 |
| Glu | Glu | Glu | Ala | Glu | Asn | Ala | Pro | Arg | Met | His | Cys | Ser | Ala | Glu | Gly |
| | 240 | | | | | 245 | | | | | 250 | | | | |

| GAA | TGG | TTA | GTG | CCC | ATT | GGA | AAA | TGT | ATC | TGC | AAA | GCA | GGC | TAC | CAG | 995 |
| Glu | Trp | Leu | Val | Pro | Ile | Gly | Lys | Cys | Ile | Cys | Lys | Ala | Gly | Tyr | Gln |
| 255 | | | | | 260 | | | | 265 | | | | | | 270 |

| CAA | AAA | GGA | GAC | ACT | TGT | GAA | CCC | TGT | GGC | CGT | GGG | TTC | TAC | AAG | TCT | 1043 |
| Gln | Lys | Gly | Asp | Thr | Cys | Glu | Pro | Cys | Gly | Arg | Gly | Phe | Tyr | Lys | Ser |
| | | | | 275 | | | | | 280 | | | | | 285 | |

| TCC | TCT | CAA | GAT | CTT | CAG | TGC | TCT | CGT | TGT | CCA | ACT | CAC | AGT | TTT | TCT | 1091 |
| Ser | Ser | Gln | Asp | Leu | Gln | Cys | Ser | Arg | Cys | Pro | Thr | His | Ser | Phe | Ser |
| | | | 290 | | | | | 295 | | | | | 300 | | |

| GAT | AAA | GAA | GGC | TCC | TCC | AGA | TGT | GAA | TGT | GAA | GAT | GGG | TAT | TAC | AGG | 1139 |
| Asp | Lys | Glu | Gly | Ser | Ser | Arg | Cys | Glu | Cys | Glu | Asp | Gly | Tyr | Tyr | Arg |
| | | 305 | | | | | 310 | | | | | 315 | | | |

| GCT | CCA | TCT | GAC | CCA | CCA | TAC | GTT | GCA | TGC | ACA | AGG | CCT | CCA | TCT | GCA | 1187 |
| Ala | Pro | Ser | Asp | Pro | Pro | Tyr | Val | Ala | Cys | Thr | Arg | Pro | Pro | Ser | Ala |
| | 320 | | | | | 325 | | | | | 330 | | | | |

| CCA | CAG | AAC | CTC | ATT | TTC | AAC | ATC | AAC | CAA | ACC | ACA | GTA | AGT | TTG | GAA | 1235 |
| Pro | Gln | Asn | Leu | Ile | Phe | Asn | Ile | Asn | Gln | Thr | Thr | Val | Ser | Leu | Glu |
| 335 | | | | | 340 | | | | | 345 | | | | | 350 |

| TGG | AGT | CCT | CCT | GCA | GAC | AAT | GGG | GGA | AGA | AAC | GAT | GTG | ACC | TAC | AGA | 1283 |
| Trp | Ser | Pro | Pro | Ala | Asp | Asn | Gly | Gly | Arg | Asn | Asp | Val | Thr | Tyr | Arg |
| | | | | 355 | | | | | 360 | | | | | 365 | |

| ATA | TTG | TGT | AAG | CGG | TGC | AGT | TGG | GAG | CAG | GGC | GAA | TGT | GTT | CCC | TGT | 1331 |
| Ile | Leu | Cys | Lys | Arg | Cys | Ser | Trp | Glu | Gln | Gly | Glu | Cys | Val | Pro | Cys |
| | | | 370 | | | | | 375 | | | | | 380 | | |

FIG. 4C

```
GGG AGT AAC ATT GGA TAC ATG CCC CAG CAG ACT GGA TTA GAG GAT AAC        1379
Gly Ser Asn Ile Gly Tyr Met Pro Gln Gln Thr Gly Leu Glu Asp Asn
        385             390                 395

TAT GTC ACT GTC ATG GAC CTG CTA GCC CAC GCT AAT TAT ACT TTT GAA        1427
Tyr Val Thr Val Met Asp Leu Leu Ala His Ala Asn Tyr Thr Phe Glu
        400             405                 410

GTT GAA GCT GTA AAT GGA GTT TCT GAC TTA AGC CGA TCC CAG AGG CTC        1475
Val Glu Ala Val Asn Gly Val Ser Asp Leu Ser Arg Ser Gln Arg Leu
415             420             425             430

TTT GCT GCT GTC AGT ATC ACC ACT GGT CAA GCA GCT CCC TCG CAA GTG        1523
Phe Ala Ala Val Ser Ile Thr Thr Gly Gln Ala Ala Pro Ser Gln Val
                435             440             445

AGC GGA GTA ATG AAG GAG AGA GTA CTG CAG CGG AGT GTC GAG CTT TCC        1571
Ser Gly Val Met Lys Glu Arg Val Leu Gln Arg Ser Val Glu Leu Ser
            450             455             460

TGG CAG GAA CCA GAG CAT CCC AAT GGA GTC ATC ACA GAA TAT GAA ATC        1619
Trp Gln Glu Pro Glu His Pro Asn Gly Val Ile Thr Glu Tyr Glu Ile
        465             470             475

AAG TAT TAC GAG AAA GAT CAA AGG GAA CGG ACC TAC TCA ACA GTA AAA        1667
Lys Tyr Tyr Glu Lys Asp Gln Arg Glu Arg Thr Tyr Ser Thr Val Lys
        480             485             490

ACC AAG TCT ACT TCA GCC TCC ATT AAT AAT CTG AAA CCA GGA ACA GTG        1715
Thr Lys Ser Thr Ser Ala Ser Ile Asn Asn Leu Lys Pro Gly Thr Val
495             500             505             510

TAT GTT TTC CAG ATT CGG GCT TTT ACT GCT GCT GGT TAT GGA AAT TAC        1763
Tyr Val Phe Gln Ile Arg Ala Phe Thr Ala Ala Gly Tyr Gly Asn Tyr
                515             520             525

AGT CCC AGA CTT GAT GTT GCT ACA CTA GAG GAA GCT ACA GGT AAA ATG        1811
Ser Pro Arg Leu Asp Val Ala Thr Leu Glu Glu Ala Thr Gly Lys Met
            530             535             540

TTT GAA GCT ACA GCT GTC TCC AGT GAA CAG AAT CCT GTT ATT ATC ATT        1859
Phe Glu Ala Thr Ala Val Ser Ser Glu Gln Asn Pro Val Ile Ile Ile
            545             550             555

GCT GTG GTT GCT GTA GCT GGG ACC ATC ATT TTG GTG TTC ATG GTC TTT        1907
Ala Val Val Ala Val Ala Gly Thr Ile Ile Leu Val Phe Met Val Phe
        560             565             570

GGC TTC ATC ATT GGG AGA AGG CAC TGT GGT TAT AGC AAA GCT GAC CAA        1955
Gly Phe Ile Ile Gly Arg Arg His Cys Gly Tyr Ser Lys Ala Asp Gln
575             580             585             590
```

FIG. 4D

| | |
|---|---|
| GAA GGC GAT GAA GAG CTT TAC TTT CAT TTT AAA TTT CCA GGC ACC AAA<br>Glu Gly Asp Glu Glu Leu Tyr Phe His Phe Lys Phe Pro Gly Thr Lys<br>                595                        600                605 | 2003 |
| ACC TAC ATT GAC CCT GAA ACC TAT GAG GAC CCA AAT AGA GCT GTC CAT<br>Thr Tyr Ile Asp Pro Glu Thr Tyr Glu Asp Pro Asn Arg Ala Val His<br>                610                        615                620 | 2051 |
| CAA TTC GCC AAG GAG CTA GAT GCC TCC TGT ATT AAA ATT GAG CGT GTG<br>Gln Phe Ala Lys Glu Leu Asp Ala Ser Cys Ile Lys Ile Glu Arg Val<br>        625                        630                        635 | 2099 |
| ATT GGT GCA GGA GAA TTC GGT GAA GTC TGC AGT GGC CGT TTG AAA CTT<br>Ile Gly Ala Gly Glu Phe Gly Glu Val Cys Ser Gly Arg Leu Lys Leu<br>        640                        645                        650 | 2147 |
| CCA GGG AAA AGA GAT GTT GCA GTA GCC ATA AAA ACC CTG AAA GTT GGT<br>Pro Gly Lys Arg Asp Val Ala Val Ala Ile Lys Thr Leu Lys Val Gly<br>655                      660                        665                670 | 2195 |
| TAC ACA GAA AAA CAA AGG AGA GAC TTT TTG TGT GAA GCA AGC ATC ATG<br>Tyr Thr Glu Lys Gln Arg Arg Asp Phe Leu Cys Glu Ala Ser Ile Met<br>                675                        680                685 | 2243 |
| GGG CAG TTT GAC CAC CCA AAT GTT GTC CAT TTG GAA GGG GTT GTT ACA<br>Gly Gln Phe Asp His Pro Asn Val Val His Leu Glu Gly Val Val Thr<br>        690                        695                        700 | 2291 |
| AGA GGG AAA CCA GTC ATG ATA GTA ATA GAG TTC ATG GAA AAT GGA GCC<br>Arg Gly Lys Pro Val Met Ile Val Ile Glu Phe Met Glu Asn Gly Ala<br>            705                      710                    715 | 2339 |
| CTA GAT GCA TTT CTC AGG AAA CAT GAT GGG CAA TTT ACA GTC ATT CAG<br>Leu Asp Ala Phe Leu Arg Lys His Asp Gly Gln Phe Thr Val Ile Gln<br>        720                        725                        730 | 2387 |
| TTA GTA GGA ATG CTG AGA GGA ATT GCT GCT GGA ATG AGA TAT TTG GCT<br>Leu Val Gly Met Leu Arg Gly Ile Ala Ala Gly Met Arg Tyr Leu Ala<br>735                      740                        745                750 | 2435 |
| GAT ATG GGA TAT GTT CAC AGG GAC CTT GCA GCT CGC AAT ATT CTT GTC<br>Asp Met Gly Tyr Val His Arg Asp Leu Ala Ala Arg Asn Ile Leu Val<br>                755                        760                765 | 2483 |
| AAC AGC AAT CTC GTT TGT AAA GTG TCA GAT TTT GGC CTG TCC CGA GTT<br>Asn Ser Asn Leu Val Cys Lys Val Ser Asp Phe Gly Leu Ser Arg Val<br>            770                        775                    780 | 2531 |
| ATA GAG GAT GAT CCA GAA GCT GTC TAT ACA ACT ACT GGT GGA AAA ATT<br>Ile Glu Asp Asp Pro Glu Ala Val Tyr Thr Thr Thr Gly Gly Lys Ile<br>        785                        790                    795 | 2579 |

FIG. 4E

```
CCA GTA AGG TGG ACA GCA CCC GAA GCC ATC CAG TAC CGG AAA TTC ACA          2627
Pro Val Arg Trp Thr Ala Pro Glu Ala Ile Gln Tyr Arg Lys Phe Thr
    800             805                 810

TCA GCC AGT GAT GTA TGG AGC TAT GGA ATA GTC ATG TGG GAA GTT ATG          2675
Ser Ala Ser Asp Val Trp Ser Tyr Gly Ile Val Met Trp Glu Val Met
815                 820                 825                 830

TCT TAT GGA GAA AGA CCT TAT TGG GAC ATG TCA AAT CAA GAT GTT ATA          2723
Ser Tyr Gly Glu Arg Pro Tyr Trp Asp Met Ser Asn Gln Asp Val Ile
                835                 840                 845

AAA GCA ATA GAA GAA GGT TAT CGT TTA CCA GCA CCC ATG GAC TGC CCA          2771
Lys Ala Ile Glu Glu Gly Tyr Arg Leu Pro Ala Pro Met Asp Cys Pro
        850                 855                 860

GCT GGC CTT CAC CAG CTA ATG TTG GAT TGT TGG CAA AAG GAG CGT GCT          2819
Ala Gly Leu His Gln Leu Met Leu Asp Cys Trp Gln Lys Glu Arg Ala
            865                 870                 875

GAA AGG CCA AAA TTT GAA CAG ATA GTT GGA ATT CTA GAC AAA ATG ATT          2867
Glu Arg Pro Lys Phe Glu Gln Ile Val Gly Ile Leu Asp Lys Met Ile
        880                 885                 890

CGA AAC CCA AAT AGT CTG AAA ACT CCC CTG GGA ACT TGT AGT AGG CCA          2915
Arg Asn Pro Asn Ser Leu Lys Thr Pro Leu Gly Thr Cys Ser Arg Pro
895                 900                 905                 910

ATA AGC CCT CTT CTG GAT CAA AAC ACT CCT GAT TTC ACT ACC TTT TGT          2963
Ile Ser Pro Leu Leu Asp Gln Asn Thr Pro Asp Phe Thr Thr Phe Cys
                915                 920                 925

TCA GTT GGA GAA TGG CTA CAA GCT ATT AAG ATG GAA AGA TAT AAA GAT          3011
Ser Val Gly Glu Trp Leu Gln Ala Ile Lys Met Glu Arg Tyr Lys Asp
            930                 935                 940

AAT TTC ACG GCA GCT GGC TAC AAT TCC CTT GAA TCA GTA GCC AGG ATG          3059
Asn Phe Thr Ala Ala Gly Tyr Asn Ser Leu Glu Ser Val Ala Arg Met
        945                 950                 955

ACT ATT GAG GAT GTG ATG AGT TTA GGG ATC ACA CTG GTT GGT CAT CAA          3107
Thr Ile Glu Asp Val Met Ser Leu Gly Ile Thr Leu Val Gly His Gln
    960                 965                 970

AAG AAA ATC ATG AGC AGC ATT CAG ACT ATG AGA GCA CAA ATG CTA CAT          3155
Lys Lys Ile Met Ser Ser Ile Gln Thr Met Arg Ala Gln Met Leu His
975                 980                 985                 990

TTA CAT GGA ACT GGC ATT CAA GTG TGATATGCAT TTCTCCCTTT TAAGGGAGAT         3209
Leu His Gly Thr Gly Ile Gln Val
                995
```

FIG. 4F

| | | | | | | |
|---|---|---|---|---|---|---|
| TACAGACTGC | AAGAGAACAG | TACTGGCCTT | CAGTATATGC | ATAGAATGCT | GCTAGAAGAC | 3269 |
| AAGTGATGTC | CTGGGTCCTT | CCAACAGTGA | AGAGAAGATT | TAAGAAGCAC | CTATAGACTT | 3329 |
| GAACTCCTAA | GTGCCACCAG | AATATATAAA | AAGGGAATTT | AGGATCCACC | ATCGGTGGCC | 3389 |
| AGGAAAATAG | CAGTGACAAT | AAACAAAGTA | CTACCTGAAA | AACATCCAAA | CACCTTGAGC | 3449 |
| TCTCTAACCT | CCTTTTTGTC | TTATAGACTT | TTTAAAATGT | ACATAAAGAA | TTTAAGAAAG | 3509 |
| AATATATTTG | TCAAATAAAA | TCATGATCTT | ATTGTTAAAA | TTAATGAAAT | ATTTTCCTTA | 3569 |
| AATATGTGAT | TTCAGACTAT | TCCTTTTTAA | AATCATTTGT | GTTTATTCTT | CATAAGGACT | 3629 |
| TTGTTTTAGA | AAGCTGTTTA | TAGCTTTGGA | CCTTTTTAGT | GTTAAATCTG | TAACATTACT | 3689 |
| ACACTGGGTA | CCTTTGAAAG | AATCTCAAAT | TTCAAAAGAA | ATAGCATGAT | TGAAGATACA | 3749 |
| TCTCTGTTAG | AACATTGGTA | TCCTTTTTGT | GCCATTTTAT | TCTGTTTAAT | CAGTGCTGTT | 3809 |
| TTGATATTGT | TTGCTAATTG | GCAGGTAGTC | AAGAAAATGC | AAGTTGCCAA | GAGCTCTGAT | 3869 |
| ATTTTTTAAA | AAGAATTTTT | TTGTAAAGAT | CAGACAACAC | ACTATCTTTT | CAATGAAAAA | 3929 |
| AGCAATAATG | ATCCATACAT | ACTATAAGGC | ACTTTTAACA | GATTGTTTAT | AGAGTGATTT | 3989 |
| TACTAGAAAG | AATTTAATAA | ACTCGAAGTT | TAGGTTTATG | AGTATATAAA | CAAATGAGGC | 4049 |
| ACTTCATCTG | AAGAATGTTG | GTGAAGGCAA | GTCTCTGAAA | GCAGAACTAT | CCAGTGTTAT | 4109 |
| CTAAAAATTA | ATCTGAGCAC | ATCAAGATTT | TTTCATTCTC | GTGACATTAG | GAAATTTAGG | 4169 |
| ATAAATAGTT | GACATATATT | TTATATCCTC | TTCTGTTGAA | TGCAGTCCAA | ACATGAAAGG | 4229 |
| AAATAATTGT | TTTATATTAT | AACTCTGAAG | CATGATAAAG | GGGCAGTTCA | CAATTTTCAC | 4289 |
| CATTTAAACA | CAAATTTGCT | GCACAGAATA | TCACCATTGC | AGTTCAAAAC | AAAACAAAAC | 4349 |
| AAAAGTCTT | TTGTTTGTGA | ACACTGATGC | AAGAAACTTG | TTAAATGAAA | GGACTCTTTA | 4409 |
| CCCTAGAAGG | AAGAGGTGAA | GGATCTGGCT | TGTTTTTAAA | GCTTTATTTA | TTAAACCATA | 4469 |
| TTATTTGATT | ACTGTGTTAG | AATTTCATAA | GCAATAATTA | AATGTGTCTT | TATGGAATTC | 4529 |

FIG. 5A

```
CONS   MARARPP........s..ll..lllldal...aa.pa.EvtLlDskt.qgeLgWishPp..GNee.sg.den.tpirtYqvCnvme.sqmn.WLrtnwl:
EPH            MERRWPLGLGLVLLLCAPLPPGARAKEVTLMDTSKAQGELGWLLDPPRDGWSEQQQILNGT.PLYMYQDCPMQGRRDTDHWLRSNWIY
ECK            MELQAARACFALLMGCALAAAAAQGKEVVLLDFAAAGGELGWLTHPYGKGWDLMQNIMNDM.PIYMYSVCNVMSGDQDN.WLRTNWVY
HEK4           MDCQLSILLLLSCVLDSFGELIFQPSNEVNLLDSKTIQGELGWISYPSH.GWEEISGVDEHYTPIRTYQVCNVMDHSQNN.WLRTNWVP
HEK5                      LLAAVEETLMDSTTATAELGWMVHPPS.GWEEVSGYDENMNTIRTYQVCNVFESSQNN.WLRTKFIR
HEK7                  ALRTLLASPSNEVNLLDSRTVMGDLGWIAFPKN.GWEEIGEVDENYAPIHTYQVCKVMEQNQNN.WLLTSWIS
HEK8           MAGIFYFALFSCLFGICDAVTGSRVYPANEVTLLDSRSVQGELGWIASPLEGGWEEVSIMDEKNTPIRTYQVCNVMEPSQNN.WLRTDWIT
HEK2    MARARPPPPPSPPPGLLPLLPPLLLLPAGCRALEETLMDTKWVTSELAWTSHPES.GWEEVSGYDEAMNPIRTYQVCNVRESSQNN.WLRTGFIW
HEK11          MVFQTRYPSWIILCYIWLLRFAHTGEAQAAKEVLLLDSKAQQTELEWISSPPN.GWEEISGLDENYTPIRTYQVCQVMEEPNQNN.WLRTNWIS
                                                          *               *

CONS   rg.gaqriyvelkft.RDCnS.Pgvlgt..CKETFNlyYyEsddd....tgrniren.fvKidriaAdesftq.Dlgdr.mklntevrsvGplskkGfYL
EPH    RGEEASRVHVELQFTVRDCKSFPGGAGPLGCKETFNLLYMESDQD....VGIQLRRPLFQKVTTVAADQSFTIRDLASGSVKLNVERCSLGRLTRRGLYL
ECK    RG.EAERNNFELNFTVRDCNSFPGGASS..CKETFNLLYYAESDLD....YGTNFQKRLFTKIDTIAPDEITVSSDFEARHVKLNVEERSVGPLTRKGFYL
HEK4   RN.SAQKIYVELKFTLRDCNSIPLVLGT..CKETFNLYYMESDDD....HGVKFREHQFTKIDTIAADESFTQMDLGGRVMKINTEVRSFGPVNKKGFYL
HEK5   RR.GAHRIHVEMKFSVRDCSSIPSVPGS..CKETFNLYYYEADFDSATKTFPNMMENPWVKVDTIAADESFSQVDLGGRVMKINTEVRSFGPVSRSGFYL
HEK7   NE.GASRIFIELKFTLRDCNSLPGGLGT..CKETFNMYYFESDDQ....NGRNIKENQYIKIDTIAADESFTELDLGDRVMKLNTEVRDVGPLSKKGFYL
HEK8   RE.GAQRVYIEIKFTLRDCNSLPGVMGT..CKETFNLLYYYESDND....KERFIRENQFVKIDTIAADESFTQVDIGDRIMKLNTEIRDVGPLSKKGFYL
HEK2   RR.DVQRVYVELKFTVRDCNSIPNIPGS..CKETFNLFYYEADSDVASASSPFWMENPYVKVDTIAPDESFSRLDAGRV....NTKVRSFGPLSKAGFYL
HEK11  KG.NAQRIFVELKFTLRDCNSLPGVLGT..CKETFNLYYYETDYD....TGRNIRENLYVKIDTIAADESFTQGDLGERKMKLNTEVREIGPLSQKGFYL
```

FIG. 5B

```
CONS   AFqdvGaC..aLvsVrv.ykkCpstv.nlA.FpdT.tgadssLvevrG.Cvnna.....e...pp.m.CsadGEMlVPiGkC.CkaGyee...gtaCgaCp
EPH    AFHNPGACVALVSVRVFYQRCPETLNGLAQFPDTLPG.PA.GLVEVAGTCLPHARASPRPSGAPRMHCSPDGEMLVPVGRCHCEPGYEEGGSGEACVACP
ECK    AFQDIGACVALLSVRVYYKKCPELLQGLAHFPETIAGSDAPSLATVAGTCVDHA.VVPPGGEEPRMHCAVDGEMLVPIGQCLCQAGYEKVED..ACQACS
HEK4   AFQDVGACVALVSVRVYFKICPFTVKRLAMFPDTVP.MDSQSLVEVRGSCVNNS....KEEDPPRMYCSTEGEMLVPIGKCSCNAGYEER..GFMCQACR
HEK5   AFQDYGGCMSLIAVRVFYRKCPRIIQNGAIFQETLSGAESTSLVAARGSCIANA...EEVDVPIKLYCNGDGEMLVPIGRCMCKAGFEAVENGTVCRGCP
HEK7   AFQDVGACIALVSVRVYYTKCPSVVRHLAVFPDTITGADSSQLLEVSGSCVNHS....VTDEPPKMHCSAEGEMLVPIGKCMCKAGYEEK.NGT.CQVCR
HEK8   AFQDVGACIALVSVRVFYTKCPLTVRNLAQFPDTITGADTSSLVEVRGSCVNNS....EEKDVPKMYCGADGEMLVPIGNCLCNAGHEER..SGEGQACK
HEK2   AFQDQGACMSLISVRAFYKKCASTYAGFALFPETLTGAEPTSLVIAPGTCIPNA...VEVSVPLKLYCNGDGEWMVPVGACTCHATGHEEPAAKESQCRPCP
HEK11  AFQDVGACIALVSVRVYKVYYKKCWSIIENLAIFPDTVTGSEFSSLVEVRGTCVSSA..EEEAENAPRMHCSAEGEMLVPIGKCICKAGYQQK..GDTCEPCG CONS   pGfyka..gd.pClkCPphs..ttsegatsCtCengy.Radsdppsma Ctrpsapmlisnvnetsv.LeWsppadtGgR.Dv.yn.iCkkCg.ga...g
EPH    SGSYRMDMDTPHCLTCPQQSTAESEGATICTCESGHYRAPGEGPQVACTGPPSAPRNLSFSASGTQLSLRMEPPADTGGRQDVRYSVRCSQCQGTAQDGG
ECK    PGFFKFEASESPCLECPEHTLPSPEGATSCECEEGEGFTRAPQDPASMPCTRPPSAPHYLTAVGMGAKVELRWTPPQDSGGREDIVYSVTCEQCWPES...G
HEK4   PGFYKALDGNMKCAKCPPHSSTQEDGSMNCRCENNYFRADKDPPSMACTRPPSSPRNVISNINETSVILDWSWPLDTGGRKDVTFNIICKKCGWNI...K
HEK5   SGTFKANQGDEACTHCPINSRTTSEGATMCVCRNGYYRADILDLDMPCTTIPSAPQAVISSVNETSLMLEWTPPRDSGGREDLVNIICKSCGSGR...G
HEK7   PGFFKASPHIQSCGKCPPHSYTHEEASTSCVCEKDYFRRESDPPTMACTRPPSAPRNAISNVNETSVFLEWIPPADTGGRKDVSYYIACKKCNSHA...G
HEK8   IGYYKALSTDATCAKCPPHSYSVMEGATSCTCDRGFFRADNDAASMPCTRPPSAPIMLISNVNETSVNLEWSSPQNTGGRQDISYNVVCKKCGAGD..PS
HEK2   PGSYKAKQGEGPCLPCPPNSRTTSPAASICTCHNNFYRADSDSADSACTTVPSPPRGVISNVNETSLILEWSEPRDLGVRDDLLYNVICKKC.HGAGGAS
HEK11  RGFYKSSSQDLQCSRCPTHSFSDKEGSRCECEDGYYRAPSDPPYVACTRPPSARQNLIFNINQTTVSLEWSPPADNGGRNDVTYRILCKRCSWEQ...G
```

FIG. 5C

```
CONS   .CepCg.nvry.prqlgLt.t.vtvsdLlahtnYtFe.eAvNGVs.l....sp.q.asvsv.ittnqaaps.v.tvr....sr.s.slsW.qep.rpngv
EPH    PCQPCGVGVHFSPGARALTTPAVHVNGLEPYANYTFNVEAQNGVSGLGSSGHAS..TSVSISMGHAESLS..GLSLRLVKEPRQLELTWAGSRPRSPGA
ECK    ECGPCEASVRYSEPPHGLTRTSVTVSDLEPHMNYTFTVEARNGVSGLVTSRSFR.TASVS..I..NQ...TEPPKVRLEGRSTTSLSVSW.SIPPPQQSR
HEK4   QCEPCSPNVRFLPRQFGLTNTTVTVTDLLAHTNYTFEIDAVNGVSEL..SSPPRQFAAV..SITTNQAAPSPVLTIKKDRTSRNSISLSW.QEPEHPNGI
HEK5   ACTRCGDNVQYAPRQLGLTEPRIYISDLLAHTQYTFEIQAVNGVTD..QSPFSPQFASV..NITTNQAAPSAVSIMHQVSRTVDSITLSW.SQPDQPNGV
HEK7   VCEECGHVRYLPRQSGLKNTSVMMVDLLAHTNYTFEIEAVNGVSDL....SPGARQYVSVNVTTNQAAPSPVTNVKKGKIAKNSISLSW.QEPDRPNGI
HEK8   KCRPCGSGVHYTPQQNGLKTTKVSITDLLAHTNYTFEIWAVNGVSK....YNPNPDQSVSVTVTTNQAAPSSIALVQAKEVTRYSVALAW.LEPDRPNGV
HEK2   ACSRCDDNVEFVPRQLGLSEPRVHTSHLLAHTRYTFEVQAVNGVSGK....SPLPPRYAAVNITTNQAAPSEVPTLRLHSSSGSSLTLSW.APPERPNGV
HEK11  ECVPCGSNIGYMPQQTGLEDNYTVMDLLAHANYTFEVEAVNGVSDL....SRSQRLFAAVSITTGQAAPSQVSGVMKERVLQRSVELSW.QEPEHPNGV CONS   il.YEvkyyekdq.ersy.iv..k.tsvt.dgLkpdt.YvfqvrarTaaGyG..Sr..efeT.pea.sgsg...ivvviivs.aga..llvv..v.l..r
EPH    NLTYE....LHVLNQDEERYQMVLEPRVLLTELQPDTTYIVRVRMLTPLGPGPFSPDHEFRTSPPVSRGLTGGEIVAVIFGLLLGAALLGILVFRSRRA
ECK    VWKYEV.TYRKKGDSNSYNVRRTEGFSVTLDDLAPDTTYLVQQALTQEGQGAGSKVHEFQTLSPEGSGNLAVIGGVAVGVVLLLVLAGVGFFIHRRRKN
HEK4   ILDYEVKYYEKQEQETSYTILRARGTNVTISSLKPDTIYVLQIRARTAAGYGTNSRKFEFETSPDSFSISGESSQVVMIAISAAVAILLTVVIYVLIGR
HEK5   ILDYELQYYEKELSEYNATAIKSPTNTVTVQGLKAGAIYFQVGLKPASVYFQIRARTVAGYGRYSGKMYFQTMTEAEYQTSIQEKLPLIIGSSAAGLVFLIAVVLAVVIGVLLSGR
HEK7   ILEYEIKHFEKDQETSYTII.KSKETTITAEGLKPASVYFQIRARTAAGYGVFSRRFEFETPVFAASSDQSQIPVIAVSTVLLVSVSGSVVLVVLIAAFVIS
HEK8   ILEYEVKYYEKDQNERSYRIVRTAARNTDIKGLNPLTSYVFHVRARTAAGYGDFSEPLEVTTNTVPSRIIGDGANSTVLLVSVSGSVVLVVLIAAFVIS
HEK2   ILDYEMKYFEK..SEGIASTVTSQMNSVQLDGLRPDARYVVQVRARTVAGYGQYSRPAEFETTSERGSGAQQLQEQLPLIVGSATAGLVFVAVVVIAIV
HEK11  ITEYEIKYYEKDQRERTYSTVKTKSTSASINNLKPGTVYVFQIRAFTAAGYGNYSPRLDVATLEEATGKMFEATAVSSEEQNPVIIAVVXVAGTIILVFM
```

FIG. 5D

```
CONS    .r..qsr.dd.ey.keq..........klpg.ktyidP.TyedPnqav.efakEidascikiekViGaGeFGEVcsGrLklp.gkre..VAIKTLKvgy
EPH     QRQRQQRHVTAPPMWIERTSCAEALCGTSRHTRTLHREPWTL..PGGWSNFPSRELDPAWLMVDTVIGEGEFGEVYRGTLRLPS.QDCKTVAIKTLKDTS
ECK     QRARQSPEDVYFSKSEQ.........LKPLKTYVDPHTYEDPNQAVLKFTTEIHPSCVTRQKVIGAGEFGEVYKGMLKTSSGKKEVPVAIKTLKAGY
HEK4    FCGYKSKHGADEKRLHFGNG.....HLKLPLGLRTYVDPHTYEDPTQAVHEFAKELDATNISIDKVVGAGEFGEVCSGRLKLPS.KKEISVAIKTLKVGY
HEK5    NRRGFERADSEYTDKLQHYT.....SGHITPGMKIYIDPFTYEDPNEAVREFAKEIDISCVKIEQVIGAGEFGEVCSGHLKLP.GKREIFVAIKTLKSGY
HEK7    RCGYSKAKQDPEEEKMHFHN.....GHIKLPGVRTYIDPHTYEDPNQAVHEFAKEIEASCITIERVIGAGEFGEVCSGRLKLP.GKRELPVAIKTLKVGY
HEK8    RRRSKYSKAKQEADEEKHLN......QGVRTYVDPFTYEDPNQAVREFAKEIDASCIKIEKVIGVGEFGEVCSGRLKVP.GKREICVAIKTLKAGY
HEK2    CLRKQRHGSDSEYTEKLQQY......IAPGMKVYIDPFTYEDPNEAVREFAKEIDVSCVKIEEVIGAGEFGEVCRGRLKQP.GRREVFVAIKTLKVGY
HEK11   VFGFIIGRRHCGYTKADQEGDEELYFHFKFPGTKTYIDPETYEDPNRAVHQFAKELDASCIKIERVIGAGEFGEVCSGRLKLP.GKRDVAVAIKTLKVGY CONS    tekQrrdFL.EAsIMGQFdhpniihLEGvvtkskPvMIitE.MENg.Ld.FLrkndgqftviQLvGMLrGIaaGMkYLsdmnYVHRDLAARNILvNsNLv
EPH     PGGQWWNFLREATIMGQFSHPHILHLEGVTKRKPIMIITEFMENAALDAFLREREDQLVPGQLVAMLQGIASGMNYLSNHNYVHRDLAARNILVNQNLC
ECK     TEKQRVDFLGEAGIMGQFSHHNIIRLEGVISKYKPMIITEYMENGSLDKFLREKDGEFSVLQLVGMLRGIAAGMKYLSDMGYVHRDLAARNILAARNILVNSNLV
HEK4    TEKQRRDFLGEASIMGQFDHPNIIRLEGVVTKSKPVMIVTEYMENGSLDSFLRKDAQFTVIQLVGMLRGIASGMKYLSDMGYVHRDLAARNILAARNILVNSNLV
HEK5    TEKQRRDFLSEASIMGQFDHPNVIHLEGVVTKSKPVMIITEFMENGSLDSFLRQNDGQFTVIQLVGMLRGIAAGMKYLADMNYVHRDLAARNILINSNLV
HEK7    TEKQRRDFLGEASIMGQFDHPNIIHLEGVVTKSKPVMIVTEYMENGSLDTFLKKNDGQFTVIQLVGMLRGISAGMKYLSAGMKYLSDMGYVHRDLAARNILVNSNLV
HEK8    TDKQRRDFLGEASIMGQFDHPNIIRLEGVVTKCKPVMIVTCKPVMIITEYMENGSLDAFLRKNDGRFTVIQLVGMLRGIGSGMKYLSDMSYVHRDLAARNILVNSNLV
HEK2    TERQRRDFLSEASIMGQFDHPNIIRLEGVVTKSRPVMILTEFMENCALDSFLRLNDGQFTVIQLVGMLRGIAAGMKYLSEMNYVHRDLAARNILVNSNLV
HEK11   TEKQRRDFLCEASIMGQFDHPNVVHLEGVTRGKPVMIVIEFMENGALHAFLRKHDGQFTVIQLVGMLRGIAAGMRYLADMGYVHRDLAARNILVNSNLV
```

FIG. 5E

```
           *
CONS   CKVSDFGlsRvleDD.pea.yT.trGGkiPiRWTaPEAIayRkFTsASDVWSYGIVmWEVmsyGerPYw.msNqdVikaieegyRLpPmDCPaal.qLM
EPH    CKVSDFGLTRLL.DDFDGTYET..QGGKIPIRWTAPEAIAHRIFTTASDVWSFGIVMWEVLSFGDKPYGEMSNQEVMKSIEDGYRLPPPVDCPAPLYELM
ECK    CKVSDFGLSRVLEDD.PEATYT.TSGGKIPIRWTAPEAISYRKFTSASDVWSFGIVMWEVMTYGERPYWELSNHEVMKAINDGFRLPTPMDCPSAIYQLM
HEK4   CKVSDFGLSRVLEDD.PEAAYT.TRGGKIPIRWTSPEAIAYRKFTSASDVWSYGIVLMEVMSYGERPYWEMSNQDVIKAVDEGYRLPPPMDCPAALYQLM
HEK5   CKVSDFGLSRFLEDDTSDPTYTSALGGKFPIRWTAPEAIQYRKFTSASDVWSYGIVMWEVMSYGERPYWDMTNQDVINAIEQDYRLPPPMDCPSALHQLM
HEK7   CKVSDFGLSRVLEDD.PEAAYT.TRGGKIPIRWTAPEAIAFRKFTSASDVWSYGIVMWEVVSYGERPYWEMTNQDVIKAVEEGYRLPSPMDCPAALYQLM
HEK8   CKVSDFGMSRVLEDD.PEAAYT.TRGGKIPIRWTAPEAIAYRKFTSASDVWSYGIVMWEVMSYGERPYWDMSNQDVIKAIEEGYRLPPPMDCPIALHQLM
HEK2   CKVSDFGLSRFLEDDPSDPTYTSSLGGKIPIRWTAPEAIAYRKFTSASDVWSYGIVMWEVMSYGERPYWDMSNQDVINAVEQDYRLPPPMDCPTALHQLM
HEK11  CKVSDFGLSRVIEDD.PEAVYT.TTGGKIPVRWTAPEAIQYRKFTSASDVWSYGIVMWEVMSYGERPYWDMSNQDVIKAIEEGYRLPAPMDCPAGLHQLM
           *                                                8

CONS   ldCWqk.RnrRPkF.qivniLdklirnpnSLktia.assr.s.pLld.sgpd.ttfrtvgeWLeaikmgryke.Ftaagyts..avaqmtaeDl.riGvt
EPH    KNCWAYDRARRPHFQKLQAHLEQLLANPHSLRTIANFDPRVTLRLPSLSGSDGIPYRTVSEWLESIRMKRYILHFHSAGLDTMECVLELTAEDLTQMGIT
ECK    MQCWQQERARRPKFADIVSILDKLIRAPDSLKTLADFDPRVSIRLPSTSGSEGVPFRTVSEWLESIKMQQYTEHFMAAGYTAIEKVVQMTNDDIKRIGVR
HEK4   LDCWQKDRNNRPKFGEIVSILDKLIRNPGSLKIITSAAARPSNLLLDQSNVDISTFRTTGDWLNGVRTAHCKEIFTGVEYSSCDTIAKISTDDMKKVGVT
HEK5   LDCWQKDRNHRPKFGQIVNTLDKMIRNPNSLKAMAPLSSGINLPLLDRTIPDYTSFNTVDEMLEAIKMGQYKESFANAGFTSFDVVSQMMEDILRVGVT
HEK7   LDCWQKERNSRPKFDEIVNMLDKLIRNPSSLKTLVNASCRVSNLLAEHSPLGSGAYRSVGEMLEAIKMGRYTEIFMENGYSSMDAVAQVTLEDLRRLGVT
HEK8   LDCWQKERSDRPKFGQIVNMLDKLIRNPNSLKRTGTESSRPNTALLDPSSPEFSAVVSVGDWLQAIKMDRYKDNFTAAGYTTLEAVVHVNQEDLARIGIT
HEK2   LDCWVRDRNLRPKFSQIVNTLDKLIRNAASLKVIASAQSGMSQPLLDRTVPDYTTFTTVGDWLDAIKMGRYKESFVSAGFASFDLVAQMTAEDLLRIGVT
HEK11  LDCWQKERAERPKFEQIVGILDKMIRNPNSLKTPLGTCSRPISPLLDQNTPDFTTFCSVGEWLQAIKMERYKDNFTAAGYNSLESVARMTIEDVMSLGIT
```

FIG. 5F

| | |
|---|---|
| CONS | lvghQkkIlsSiq.mr.Qmnqgh.p.v.V |
| EPH | LPGHQKRILCSIQGFKD |
| ECK | LPGHQKRIAYSLLGLKDQVNTVGIPI |
| HEK4 | VVGPQKKIISSIKALETQSKNGPVPV |
| HEK5 | LAGHQKKILNSIQVMRAQMNQIQSVEV |
| HEK7 | LVGHQKKIMNSLQEMKVQLVNGMVPL |
| HEK8 | AITHQNKILSSVQAMRTQMQQMHGRMVPV |
| HEK2 | LAGHQKKILSSIQDMRLQMNQTLPVQV |
| HEK11 | LVGHQKKIMSSIQTMRAQMLHLHGTGIQV |

Human

Rat

Human

Rat

NUCLEIC ACIDS ENCODING EPH-LIKE RECEPTOR TYROSINE KINASES

This is a division of application Ser. No. 08/702,367, filed Aug. 21, 1996, now U.S. Pat. No. 5,981,246, which is a continuation of application Ser. No. 08/229,509, filed Apr. 15, 1994, now abandoned. The contents of U.S. application Ser. No. 08/702,367 are being relied upon and are incorporated herein by reference.

FIELD OF THE INVENTION

The invention relates generally to receptor protein tyrosine kinases (PTKs) and particularly to novel Eph-like receptor PTKS, to fragments and analogs thereof, and to nucleic acids encoding same. The present invention also relates to methods of producing and using such receptors.

BACKGROUND OF THE INVENTION

Receptor PTKs are a structurally related family of proteins that mediate the response of cells to extracellular signals (Ullrich et al. Cell 61, 203–212 (1990)). These receptors are characterized by three major functional domains: an intracellular region containing the sequences responsible for catalytic activity, a single hydrophobic membrane-spanning domain, and a glycosylated extracellular region whose structure determines ligand binding specificity. Signal transduction is initiated by the binding of growth or differentiation factors to the extracellular domain of their cognate receptors. Ligand binding facilitates dimerization of the receptor which can induce receptor autophosphorylation. Both soluble and membrane-associated protein ligands have been shown to function in this manner. This process is the initial step in a cascade of interactions involving the phosphorylation of a variety of cytoplasmic substrates and culminating in a biological response by the cell. The best characterized response to tyrosine kinase receptor activation is cell growth. However, analysis of the role of some growth factors in vivo suggests that differentiation or cell survival might also be mediated by tyrosine kinase receptor/ligand interactions.

Receptor PTKs have been grouped into fairly well-defined families on the basis of both sequence homology and shared structural motifs. The amino acid sequence of the portion of the intracellular domain responsible for the catalytic activity is well conserved among all tyrosine kinases and even more closely matched within a receptor sub-family. Comparisons of this portion of the amino acid sequence have been used to construct phylogenetic trees depicting the relatedness of family members to each other and to the tyrosine kinases as a whole (Hanks and Quinn, Methods Enzymol. 200, 38–62 (1991)). This sequence conservation has also been exploited in order to isolate new tyrosine kinases using the polymerase chain reaction (PCR)(Wilks, Proc. Natl. Acad. Sci. USA 86, 1603–1607 (1989)). Oligonucleotides based on the highly conserved catalytic domain of PTKs can be used as PCR primers to amplify related sequences present in the template. These fragments can then be used as probes for isolation of the corresponding full-length receptor clones from cDNA libraries. Anti-phosphotyrosine antibodies have also been used to identify PTK cDNA clones in phage expression libraries (Lindberg and Pasquale, Methods Enzymol. 200, 557–564 (1991)). These strategies have been used by a number of investigators to identify an ever-increasing number of protein tyrosine kinase receptors.

There are now 51 distinct PTK receptor genes that have been published and divided into 14 sub-families One such sub-family is the EPH-like receptors. The prototype member, EPH, was isolated by Hirai et.al. (Science 238, 1717–1720 (1987)) using low stringency hybridization to a probe derived from the viral oncogene v-fps. EPH-like receptors have been implicated in cell growth based in part on studies which show that overexpression of the gene in NIH3T3 cells causes focus formation in soft agar and tumors in nude mice (Maru et al. Oncogene 5, 199–204 (1990)). Other members of the EPH sub-family which have been identified include the following:

ECK (Lindberg et al. Mol. Cell. Biol. 10, 6316–6324 (1990))

Elk (Lhoták et al. Mol. Cell. Biol. 11, 2496–2502 (1991))

Ceks 4,5,6,7,8,9, and 10 (Pasquale, Cell Regulation 2, 523–534 (1991); Sajjadi et al. The New Biologist 3, 769–778 (1991); Sajjadi and Pasquale Oncogene 8, 1807–1813 (1993))

HEK2 (Bohme et al. Oncogene 8, 2857–2862 (1993))

Eek, Erk (Chan and Watt, Oncogene 6, 1057–1061 (1991))

Ehk1, Ehk2 (Maisonpierre et al. Oncogene 8, 3277–3288 (1993))

Homologs for some of these receptors have been identified in other species (Wicks et al. Proc. Natl. Acad. Sci. USA 89, 1611–1615 (1992)); Gilardi-Hebenstreit et al. Oncogene 7, 2499–2506 (1992)). The expression patterns and developmental profiles of several family members suggest that these receptors and their ligands are important for the proliferation, differentiation and maintenance of a variety of tissues (Nieto et al. Development 116, 1137–1150 (1992)). Structurally, EPH sub-family members are characterized by an Ig-like loop, a cysteine rich region, and two fibronectin-type repeats in their extracellular domains. The amino acid sequences of the catalytic domains are more closely related to the SRC sub-family of cytoplasmic PTKS than to any of the receptor PTKs. Among the catalytic domains of receptor PTKs, the EPH sub-family is most similar in amino acid sequence to the epidermal growth factor receptor sub-family.

It is an object of the invention to identify novel receptors belonging to the EPH sub-family. A directed PCR approach has been used to identify five human EPH-like receptors from a human fetal brain cDNA library. These receptors are designated HEK4, HEK5, HEK7, HEK8, and HEK11. The relationship of these receptors to previously identified EPH-like receptors is as follows:

HEK4 is the human homolog of Cek4 (chicken) and Mek4 (mouse) and is identical to HEK (Boyd et al. J. Biol. Chem. 267, 3262–3267 (1992); Wicks et al., 1992) which was previously isolated from a human lymphoid tumor cell line.

HEK5 is the human homolog of Cek5, a full-length eph-like receptor clone from chicken. A portion of the HEK5 sequence was previously disclosed as ERK, a human clone encoding about sixty amino acids (Chan and Watt, 1991)

HEK7 is the human homolog of Cek7 isolated from chicken.

HEK8 is the human homolog of Cek8 a full-length clone from chicken and Sek, a full-length clone from mouse. (Nieto et al., 1992; Sajjadi et al., 1991)

HEK11 does not have a known non-human homolog. With the addition of the new members HEK5, HEK7, HEK8 and HEK11 and the report of a PCR fragment encoding an eph-like receptor (Lai & Lemke Neuron 6, 691–704 (1991)), a total of twelve distinct sequences that represent EPH-like receptors have been published, making it the largest known sub-family of PTKs.

It is a further object of the invention to generate soluble EPH-like receptors and antibodies to EPH-like receptors. Soluble receptors and antibodies are useful for modulating EPH-like receptor activation.

SUMMARY OF THE INVENTION

The present invention provides novel EPH-like receptor protein tyrosine kinases. More particularly, the invention provides isolated nucleic acids encoding four novel members of the sub-family of EPH-like receptor PTKs which are referred to collectively as HEKs (human-eph like kinases). Also encompassed are nucleic acids which hybridize under stringent conditions to EPH-like receptor nucleic acids. Expression vectors and host cells for the production of receptor polypeptides and methods of producing receptors are also provided.

Isolated polypeptides having amino acid sequences of EPH-like receptors are also provided, as are fragments and analogs thereof. Antibodies specifically binding the polypeptides of the invention are included. Also comprehended by the invention are methods of modulating the endogenous activity of an EPH-like receptor and methods for identifying receptor ligands.

DESCRIPTION OF THE FIGURES

FIG. 1 shows the nucleotide and predicted amino acid sequence of the HEK5 receptor (SEQ. ID NO:10 and SEQ. ID NO:11).

FIG. 2 shows the nucleotide and predicted amino acid sequence of the HEK7 receptor (SEQ. ID NO12 and SEQ. ID NO:13).

FIG. 3 shows the nucleotide and predicted amino acid sequence of the HEK8 receptor (SEQ. ID NO14 and SEQ. ID NO:115).

FIG. 4 shows the nucleotide and predicted amino acid sequence of the HEK11 receptor (SEQ. ID NO:16 and SEQ. ID NO:17).

FIG. 5 shows the comparison of the amino acid sequences of the human EPH receptor sub-family. The multiple sequence alignment was done using the LineUp program included in the Genetics Computer Group sequence analysis software package (Genetics Computer Group, (1991), Program Manual for the GCG Package, Version 7, April 1991, Madison, Wis., USA 53711). Dots indicate spaces introduced in order to optimize alignment. The predicted transmembrane domains and signal sequences of each receptor are indicated by underlining and italics, respectively. Cysteine residues conserved throughout the sub-family are indicated with asterisks. Arrows indicate the tyrosine kinase catalytic domain. Amino acid sequences of EPH, ECK and HEK2 were taken from the appropriate literature references.

FIG. 7, HEK4; FIG. 8, HEK5; FIG. 9, HEK7; FIG. 10; HEK8; FIG. 11; HEK 11.

DETAILED DESCRIPTION OF THE INVENTION

Figure 6:
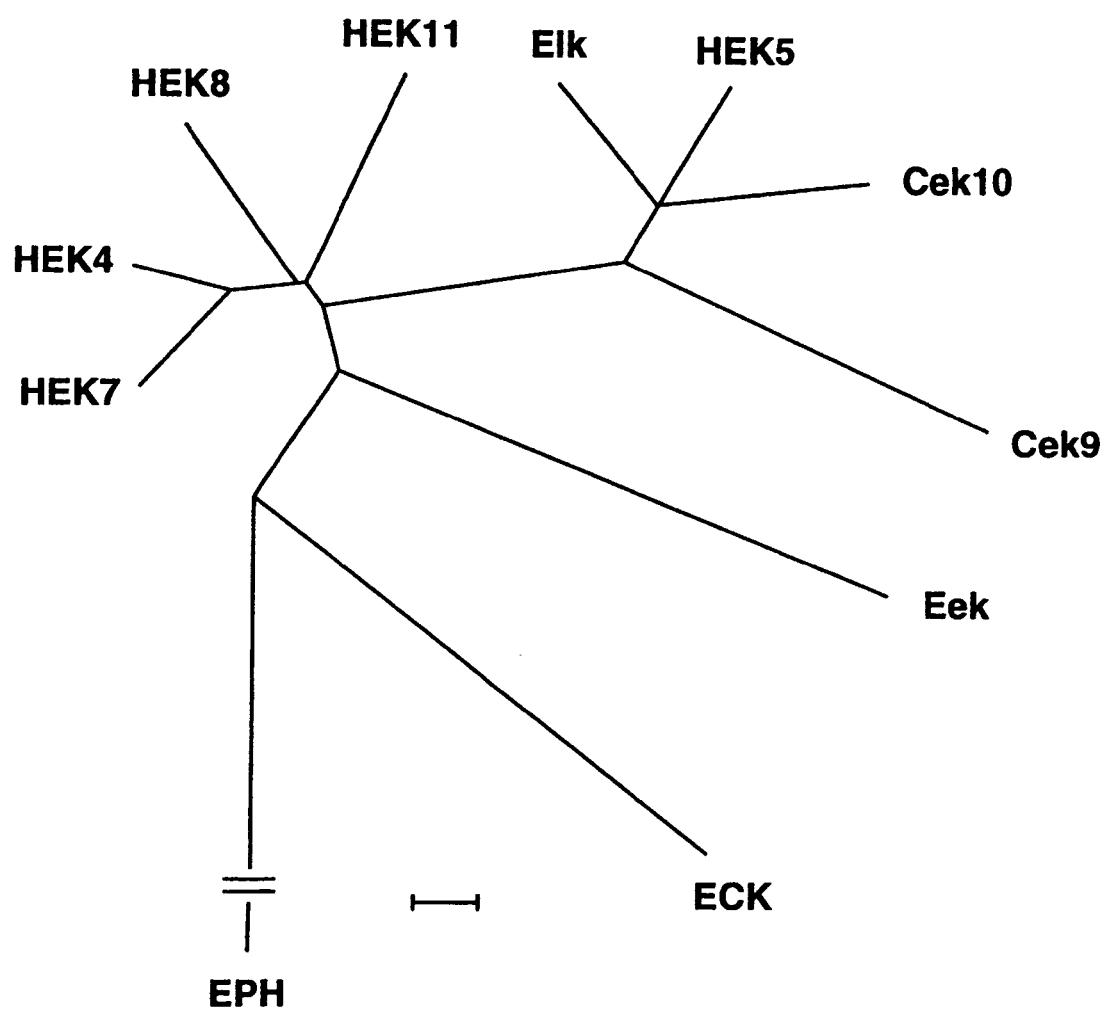
FIG. 6 shows the molecular phylogeny of the EPH sub-family of receptor protein tyrosine kinases. Catalytic domain sequences were analyzed as described by Hanks and Quinn, 1991. The scale bar represents an arbitrary evolutionary difference unit. The EPH branch, which has been shown with a discontinuity for the sake of compactness, is 23.5 units in length.

The present invention relates to novel EPH-like receptor protein tyrosine kinases. More particularly, the invention relates to isolated nucleic acids encoding four novel members of the sub-family of EPH-like receptor PTKs. These four members are designated herein as HEK (human eph-like kinases). Nucleic acids encoding HEK receptors were identified in a human fetal brain cDNA library using oligonucleotide probes to conserved regions of receptor PTKs and EPH-like receptor PTKs. The predicted amino acid sequences of three HEK receptors had extensive homology in the catalytic domain to previously identified EPH-like receptors Cek5, Cek7 and Cek8 isolated from chicken and, accordingly, are designated HEK5, HEK7 and HEK8. The predicted amino acid sequence of the fourth HEK receptor revealed that it was not a homolog of any previously identified EPH-like receptor. It is designated HEK11. It is understood that the term "HEKs" comprises HEK5, HEK7, HEK8 and HEK11 as well as analogs, variants, and mutants thereof which fall within the scope of the invention.

The invention encompasses isolated nucleic acids selected from the group consisting of:

(a) the nucleic acids set forth in any of SEQ ID NO: 10, SEQ ID NO: 12, SEQ ID NO: 14, or SEQ ID NO: 16 and their complementary strands;

(b) a nucleic acid hybridizing to the coding regions of the nucleic acids in any of SEQ ID NO: 10, SEQ ID NO: 12, SEQ ID NO: 14, or SEQ ID NO: 16 under stringent conditions; and (c) a nucleic acid of (b) which, but for the degeneracy of the genetic code, would hybridize to the coding regions of the nucleic acids in any of SEQ ID NO: 10, SEQ ID NO: 12, SEQ ID NO: 14, or SEQ ID NO: 16. The nucleic acids of the invention preferably hybridize to HEK5, HEK7, HEK8, or HEK11 coding regions under conditions allowing up to about 5% nucleotide mismatch based upon observed nucleic acid identities among known human or nonhuman EPH-like receptors. An example of such a condition is hybridization at 60° in 1M Na$^+$ followed by washing at 60° in 0.2×SSC. Other hybridization conditions may be ascertained by one skilled in the art which allow base pairing with similar levels of mismatch.

In a preferred embodiment, the isolated nucleic acids encode polypeptides having the amino acid sequences of HEK5, HEK7, HEK8 or HEK11. A nucleic acid includes cDNA, genomic DNA, synthetic DNA or RNA. Nucleic acids of this invention may encode full-length receptor polypeptides having an extracellular ligand-binding domain, a transmembrane domain, and a cytoplasmic domain, or may encode fragments such as extracellular domains which are produced in a soluble, secreted form. Nucleic acid constructs which produce soluble HEK receptors are described in Example 3. Polypeptides and fragments encoded by the nucleic acids have at least one of the biological activities of an EPH-like receptor protein tyrosine kinase, such as the ability to bind ligand.

The invention also encompasses nucleic acids encoding chimeric proteins wherein said proteins comprise part of the amino acid sequence of a HEK receptor linked to an amino acid sequence from a heterologous protein. One example of such a chimeric protein is an extracellular domain of a HEK receptor fused to a heterologous receptor cytoplasmic domain. Example 5 describes the construction and expression of a chimeric receptor comprising the HEK8 extracellular domain with the trkB cytoplasmic domain and a second chimeric receptor comprising the HEK11 extracellular domain with the trkB cytoplasmic domain. HEK receptors may also be fused to other functional protein domains, such as an Ig domain which acts as an antibody recognition site.

The nucleic acids of the present invention may be linked to heterologous nucleic acids which provide expression of receptor PTKS. Such heterologous nucleic acids include biologically functional plasmids or viral vectors which provide genetic elements for transcription, translation, amplification, secretion, etc. One example of an expression vector suitable for producing EPH-like receptors of the present invention is pDSRα which is described in Example 3. It is understood that other vectors are also suitable for expression of EPH-like receptors in mammalian, yeast, insect or bacterial cells. In addition, in vivo expression of nucleic acids encoding EPH-like receptor PTKs is also encompassed. For example, tissue-specific expression of EPH-like receptors in transgenic animals may be readily effected using vectors which are functional in selected tissues.

Host cells for the expression of EPH-like receptor PTKs will preferably be established mammalian cell lines, such as Chinese Hamster Ovary (CHO) cells or NIH 3T3 cells, although other cell lines suitable for expression of mammalian genes are readily available and may also be used. Such host cells are transformed or transfected with nucleic acid constructs suitable for expression of an EPH-like receptor. Transformed or transfected host cells may be used to produce suitable quantities of receptor for diagnostic or therapeutic uses and to effect targeted expression of EPH-like receptors in selected adult tissues, such as brain, kidney, and liver, or in embryonic or rapidly dividing tissues.

The present invention provides purified and isolated polypeptides having at least one of the biological properties of an EPH-like receptor (e.g. ligand binding, signal transduction). The isolated polypeptides will preferably have an amino acid sequence as shown in any of SEQ ID NO: 11, SEQ ID NO: 13, SEQ ID NO: 15 or SEQ ID NO: 17. Polypeptides of this invention may be full-length polypeptides having an extracellular domain, a transmembrane domain, and a cytoplasmic domain, or may be fragments thereof, e.g., those having only an extracellular domain or a portion thereof. It will be understood that the receptor polypeptides may also be analogs or naturally-occurring variants of the amino acid sequences shown in SEQ ID NO: 11, SEQ ID NO: 13, SEQ ID NO: 15 SEQ ID NO: 17. Such analogs are generated by amino acid substitutions, deletions and/or insertions using methods available in the art.

Polypeptides of the invention are preferably the product of expression of an exogenous DNA sequences, i.e., EPH-like receptors are preferably produced by recombinant means. Methods of producing EPH-like receptors comprising culturing host cells which have been transformed or transfected with vectors expressing an EPH-like receptor are also encompassed. EPH-like receptors, particularly fragments, may also be produced by chemical synthesis. The polypeptides so produced may be glycosylated or nonglycosylated depending upon the host cell employed, or may have a methionine residue at the amino terminal end. The polypeptides so produced are identified and recovered from cell cultures employing methods which are conventional in the art.

EPH-like receptors of the present invention are used for the production of antibodies to the receptors. Antibodies to HEK receptors have been described in Example 4. Antibodies which recognize the polypeptides of the invention may be polyclonal or monoclonal and may be binding fragments or chimeric antibodies. Such antibodies are useful in the detection of EPH-like receptors in diagnostic assays in the purification of receptor, and in the modulation of EPH-like receptor activation.

As described in co-pending and co-owned U.S. Ser. No. 08/145,616, the only known ligand for an EPH-like receptor is a protein which binds to and induces phosphorylation of the eck receptor. The ECK receptor ligand was previously identified as B61. (Holzman et al. Mol. Cell. Biol. 10, 5830–5838 (1990)). The availability of ECK receptor was important for the identification of a ligand since B61, although known, had not been previously implicated as an ECK receptor ligand. Therefore, EPH-like receptors having ligand binding domains are useful for the identification and purification of ligands. Polypeptides of the present invention may be used to identify and purify ligands for HEK5, HEK7, HEK8 and HEK11 receptors. Binding assays for the detection of potential ligands may be carried out in solution or by receptor immobilization on a solid support using methods such as those described in co-pending and co-owned U.S. Ser. No. 08/145,616. Such assays may employ an isolated ligand binding domain of a HEK receptor. Alternatively, a HEK ligand binding domain fused to an Ig domain may be used to detect the presence of HEK ligand on cell surfaces.

Soluble EPH-like receptors may be used to modulate (i.e., increase or decrease) the activation of the cell-associated receptors, typically by competing with the receptor for unbound ligand. Modulation of EPH-like receptor activation may in turn alter the proliferation and/or differentiation of receptor-bearing cells. For example, based upon the observed tissue distribution of the receptors of this invention (see Table 5), soluble HEK7 receptor is likely to primarily affect proliferation and/or differentiation of brain cells, while soluble HEK5 receptor may affect primarily brain and pancreatic cells, although effects of HEK5 receptor on other tissues may not be excluded.

Antibodies to EPH-like receptors are useful reagents for the detection of receptors in different cell types using immunoassays conventional to the art. Antibodies are also useful therapeutic agents for modulating receptor activation. Antibodies may bind to the receptor so as to directly or indirectly block ligand binding and thereby act as an antagonist of receptor activation. Alternatively, antibodies may act as an agonist by binding to receptor so as to faciliate ligand binding and bring about receptor activation at lower ligand concentrations. In addition, antibodies of the present invention may themselves act as a ligands by inducing receptor activation. It is also contemplated that antibodies to EPH-like receptors are useful for selection of cell populations enriched for EPH-like receptor bearing cells. Such populations may be useful in cellular therapy regimens where it is necessary to treat patients which are depleted for certain cell types.

The isolated nucleic acids of the present inventions may be used in hybridization assays for the detection and quantitation of DNA and/or RNA coding for HEK5, HEK7, HEK8, HEK11 and related receptors. Such assays are important in determining the potential of various cell types to express these receptors and in determining actual expression levels of HEK receptors. In addition, the nucleic acids are useful for detecting abnormalities in HEK receptor genes, such as translocations, rearrangements, duplications, etc.

Therapeutic regimens involving EPH-like receptors will typically involve use of the soluble form of the receptor contained in a pharmaceutical composition. Such pharmaecutical compositions may contain pharmaceutically acceptable carrier, diluents, fillers, salts, buffers, stabilizers and/or other materials well known in the art. Further examples of such constituents are described in Remington's Pharmaceutical Sciences 18th ed., A. R. Gennaro, ed. (1990). Administration of soluble EPH-like receptor compositions may be by a variety of routes depending upon the condition being treated, although typically administration will occur by intravenous or subcutaneous methods. Pharmaceutical compositions containing antibodies to EPH-like receptors will preferably include mouse-human chimeric antibodies or CDR-grafted antibodies in order to minimize the potential for an immune response by the patient to antibodies raised in mice. Other components of anti-EPH antibody compositions will be similar to those described for soluble receptor.

The amount of soluble Eph-like receptors or anti-Eph antibody in a pharmaceutical composition will depend upon the nature and severity of the condition being treated. Said amount may be determined for a given patient by one skilled in the art. It is contemplated that the pharmaceutical compositions of the present invention will contain about 0.01 μg to about 100 mg of soluble receptor or anti-Eph antibody per kg body weight.

A method for modulating the activation of an EPH-like receptor PTK is also provided by the invention. In practicing this method, a therapeutically effective amount of a soluble EPH-like receptor or an anti-EPH antibody is administered.

The term "therapeutically effective amount" is that amount which effects an increase or decrease in the activation of an EPH-like receptor and will range from about 0.01 μg to about 100 mg of soluble receptor or anti-EPH antibody per kg body weight. In general, therapy will be appropriate for a patient having a condition treatable by soluble receptor or anti-EPH antibody and it is contemplated that such a condition will in part be related to the state of proliferation and/or differentiation of receptor-bearing cells. Based upon the tissue distribution of HEK receptors shown in Table 4, treatment with the pharmaceutical compositions of the invention may be particularly indicated for disorders involving brain, heart, muscle, lung, or pancreas. However, some HEK receptors are displayed on a wide variety of tissues, so it is understood that the effects of modulating receptor activation may not be limited to those tissues described herein.

The following examples are offered to more fully illustrate the invention, but are not to be construed as limiting the scope thereof. Recombinant DNA methods used in the following examples are generally as described in Sambrook et al. *Molecular Cloning: A Laboratory Manual* Cold Spring Harbor Laboratory Press, 2nd ed. (1989)

EXAMPLE 1

Cloning and Sequencing of HEK Receptor cDNA

We have isolated clones for five members of the EPH sub-family of receptor PTKs from a human fetal brain cDNA library. Oligonucleotides were designed based on conserved amino acid sequences within the kinase domain. Primer I was based on the amino acid sequence Trp-Thr-Ala-Pro-Glu-Ala-Ile (SEQ ID NO: 1), which is well-conserved among PTKs of many families. Primer II was based on the sequence Val-Cys-Lys-Val-Ser-Asp-Phe-Gly (SEQ ID NO: 2), which is invariant among EPH sub-family members but, except for the sequence Asp-Phe-Gly, is rarely found in other PTKs. Fully degenerate oligonucleotides corresponding to reverse translations of these protein sequences were synthesized and utilized as primers in a polymerase chain reaction (PCR) with disrupted phage from a human fetal brain cDNA library as the template. The products of this PCR reaction were cloned into the plasmid vector pUC19 and the nucleotide sequence of the inserts was determined. Of the 35 PCR inserts-sequenced, 27 were recognizable as portions of PTK genes. Their correspondence to previously published sequences is summarized in Table 1.

TABLE 1

| Receptor | PCR Products | Number of Clones |
| --- | --- | --- |
| Elk | VCKVSDFGLSRYLQDDTSDPTYTSSLGGKIPVRWTAPEAI (SEQ ID NO: 3) | 2 |
| HEK4, HEK7 | VCKVSDFGLSRVLEDDPEAAYTT RGGKIPIRWTAPEAI (SEQ ID NO: 4) | 5* |
| HEK5 | VCKVSDFGLSRFLEDDTSDPTYTSALGGKIPIRWTAPEAI (SEQ ID NO: 5) | 8 |
| HEK8 | VCKVSDFGMSRVLEDDPEAAYTT RGGKIPIRWTAPEAI (SEQ ID NO: 6) | 4 |
| HEK11 | VCKVSDFGLSRVIEDDPEAVYTTT GGKIPVRWTAPEAI (SEQ ID NO: 7) | 1 |
| SRC | VCKVSDFGLAR LIEDNEYTARQ GAKFPIKWTAPEAI (SEQ ID NO: 8) | 6* |
| PDGF-β | VCKVSDFGLARDIMRDSNYISK GSTFLPLKWTAPEAI (SEQ ID NO: 9) | 1 |

An asterisk indicates that different nucleic acid sequences encoded the amino acid sequence shown.

Six PCR inserts predict amino acid sequences which are identical to a portion of SRC, although they comprise two distinct nucleotide sequences. One insert appears to code for the human platelet derived growth factor (PDGF)-β receptor. The remaining 18 PCR inserts consist of 6 distinct nucleotide sequences, all of which appear to be fragments of EPH sub-family members. One of the sequence predicts an amino acid sequence identical to the corresponding region of rat Elk (Lhotak et al., 1991)) and is likely to represent its human homolog. Two inserts predict amino acid sequences which match the translation of the PCR fragment tyro-4 (Lai and Lemke, 1991)) but are clearly distinct at the nucleotide level while two others correspond to tyro-1 and tyro-5. The sixth PCR insert has a previously unreported EPH-related sequence. Since five of the clones contained portions of potential EPH sub-family members for which full-length sequences had not been reported, each was radiolabeled and used as a probe to screen a human fetal brain cDNA library. Several clones corresponding to each of the five probes were isolated. For each of the five receptors, the nucleotide sequence of the clone containing the largest portion of the predicted coding region was determined.

A single cDNA clone containing the complete coding region was isolated only for HEK4. The portions of HEK5, HEK7, HEK10 and HEK11 coding for the amino terminus of these receptors were not found in any of the clones. In order to obtain the complete coding sequence, the Rapid Amplification of cDNA Ends (RACE) technique was employed. In some cases, more than one round of RACE was necessary to obtain the missing portion of the coding region. Using this strategy, complete coding sequences were obtained for all clones except HEK7 which lacked the complete leader sequence. The DNA sequences of HEK5, HEK7, HEK8 and HEK11 are shown in FIGS. 1–4, respectively, and in SEQ ID NO: 10 (HEK5), SEQ ID NO: 12 (HEK7), SEQ ID NO: 14 (HEK 8) and SEQ ID NO: 16 (HEK11). The amino acid sequences are shown in SEQ ID NO: 11 (HEK5), SEQ ID NO: 13 (HEK7), SEQ ID NO: 15 (HEK8) and SEQ ID NO: 17 (HEK 11).

EXAMPLE 2

Analysis of HEK Receptor Sequences

HEK5, HEK7, HEK8 and HEK11 represent novel human EPH sub-family members, although homologs for all except HEK11 have been isolated from other species. We refer to human EPH receptor sub-family members as HEKs (human EPH-like kinases) following the nomenclature of Wicks et al., 1992). We have chosen names and numbers for these receptors to correspond with previously discovered members of the family in chicken (Ceks) and in mouse (Mek) (Sajjadi et al. 1991; Sajjadi and Pasquale, 1993; Pasquale, 1991). Extending the convention of designating the species of origin by the first letter, we refer to the rat homologs of the HEK receptors as Reks (rat EPH-like kinases).

HEK4 is the human homolog of the chicken receptor Cek4 (91% amino acid identity in the catalytic domain) and the mouse receptor Mek4 (96% amino acid identity in the catalytic domain). The amino acid sequence of HEK5 is very closely related (96% amino acid identity in the catalytic domain) to the chicken receptor Cek5 (Pasquale et al. J. Neuroscience 12, 3956–3967 (1992); Pasquale, 1991). HEK7 is probably the human homolog of the recently reported Cek7 (Sajjadi and Pasquale, 1993). HEK8 is likewise very closely related to Sek (Gilardi-Hebenstreit et al., 1992)) and Cek8 (95% amino acid identity in the catalytic domain) (Sajjadi and Pasquale, 1993)). The human homologs for Cek6 and Cek9 have yet to be reported, while the human homolog of Cek10 has just recently been published. One of our human receptors has no close relatives in other species and apparently represents a novel member of the EPH sub-family. We have designated this receptor HEK11, assuming that human homologs for Cek 9 and 10 will be named HEK9 and HEK10, respectively. A summary of known EPH sub-family members is shown in Table 2.

TABLE 2

EPH receptor sub-family members

| Human | Non-human homologs |
|---|---|
| EPH | None identified |
| ECK | None identified |
| None identified[#] | Eek |
| HEK4* | Cek4, Mek4 |
| HEK5 | Cek5, Nuk, ERK |
| None identified[#] | Cek6, Elk |
| HEK7 | Cek7, Ehk1 |
| HEK8 | Cek8, Sek |
| None identified[#] | Cek9 |
| HEK2 | Cek10 |
| HEK11 | None identified |
| None identified | Ehk2 |

*published by Wicks et. al., 1992 as HEK
[#]Using the present nomenclature, the predicted human homolog of Eek is designated HEK3. For Cek6, the predicted human homolog is designated HEK6; For Cek9, the predicted human homolog is designated HEK9.

*published by Wicks et.al., 1992 as HEK #Using the present nomenclature, the predicted human homolog of Eek is designated HEK3. For Cek6, the predicted human homolog is designated HEK6; For Cek9, the predicted human homolog is designated HEK9.

The predicted amino acid sequences of the four novel receptor clones and the previously known EPH sub-family members ECK (SEQ ID NO: 18), EPH (SEQ ID NO: 19), HEK2 (SEQ ID NO: 20) and HEK4 (SEQ ID NO: 21) were aligned as shown in FIG. 5. The four clones are closely related to each other and to the known EPH sub-family members. The extracellular domain sequences of all four novel receptors contain the Ig-loop, fibronectin-type III repeats, and cysteine-rich region characteristic of EPH sub-family members. The positions of the 20 cysteine residues are conserved among all sub-family members. Also completely conserved is the portion of the catalytic domain used as the basis for the EPH sub-family specific primer (Val-Cys-Lys-Val-Ser-Asp-Phe-Gly, SEQ ID NO: 2, amino acids 757–764 in FIG. 5). Table 3 summarizes the percentage of sequence identity between pairs of human EPH sub-family members. The lower portion of the table shows percent amino acid identity in the catalytic domain while the upper half shows percent amino acid identity in the extracellular region. The amino acid sequences of the EPH-like receptors are extremely well-conserved (60–89% amino acid identity) in the catalytic region but not as highly conserved in the extracellular region (38–65% amino acid identity), as would be expected for members of the same receptor sub-family.

TABLE 3

Eph family amino acid sequence comparison

| | EPH | ECK | HEK4 | HEK5 | HEK7 | extracellular domains HEK8 | HEK2 | HEK11 |
|---|---|---|---|---|---|---|---|---|
| EPH | * | 47 | 42 | 38 | 40 | 43 | 40 | 42 |
| ECK | 62 | * | 47 | 41 | 45 | 46 | 41 | 46 |
| HEK4 | 62 | 76 | * | 53 | 65 | 61 | 51 | 59 |
| HEK5 | 60 | 74 | 81 | * | 52 | 53 | 63 | 51 |
| HEK7 | 61 | 76 | 89 | 83 | * | 62 | 48 | 61 |
| HEK8 | 62 | 76 | 86 | 85 | 88 | * | 52 | 57 |
| HEK2 | 61 | 74 | 81 | 89 | 82 | 83 | * | 48 |
| HEK11 | 60 | 74 | 83 | 83 | 85 | 85 | 80 | * |
| | | Catalytic domains | | | | | | |

Numbers shown are precent identity

3Numbers Shown are Precent Identity

Pairwise comparisons of amino acid sequences can be used to construct phylogenetic trees depicting the evolutionary relatedness of a family of molecules. FIG. 6 is such a tree, which summarizes the relationships among the EPH sub-family members. Only one family member is shown from each group of cross-species homologs and the human representative was used whenever possible (refer to Table 2 for a summary of cross-species homologs). The branch lengths represent the degree of divergence between members. It has been shown previously that the EPH sub-family lies on a branch evolutionarily closer to the cytoplasmic PTKs than to other receptor PTKs (Lindberg and Hunter, 1993). Interestingly, the further one moves up the tree, the more closely related the receptors become and expression becomes more localized to the brain.

EXAMPLE 3

Construction and Expression of HEK Receptor Extracellular Domains

Soluble extracellular forms of HEK receptor proteins were constructed by deletion of DNA sequences encoding transmembrane and cytoplasmic domains of the receptors and introduction of a translation stop codon at the 3' end of the extracellular domain. A construct of the HEK5 extracellular domain had a stop codon introduced after lysine at position 524 as shown in FIG. 1; the HEK7 extracellular domain was constructed with a stop codon after glutamine at position 547 as shown in FIG. 2; the HEK 8 extracellular domain was constructed with a stop codon after threonine at position 547 as shown in FIG. 3.

HEK extracellular domain was amplified from a human fetal brain cDNA library by PCR using primers 5' and 3' to the extracellular domain coding region.

For HEK5, the primers

5' CTGCTCGCCGCCGTGGAAGAAACG and; (SEQ ID NO: 22)

5' GCGTCTAGATTATCACTTCTCCTGGATGCTTGTCTGGTA (SEQ ID NO: 23)

were used to amplify the extracellular domain and to provide a restriction site for cloning into plasmid pDSRa. In addition, the following primers were used to provide a translational start site, the elk receptor signal peptide for expression; and a restriction site for cloning into pDSRα:

5' GCGGTCGACGCCGCCGCCATGGCCCTGGATTGCCTGCTGCTGTTCCTCCTG (SEQ ID NO: 24) and;

5' CGTTTCTTCCACGGCGGCGAGCAGAGATGCCAGGAGGAACAGCAGCAGGCAATC (SEQ ID NO: 25)

The resulting construct resulted in fusion of DNA encoding the elk signal sequence Met-Ala-Leu-Asp-Cys-Leu-Leu-Leu-Phe-Leu-Leu-Ala-Ser (SEQ ID NO: 26) to the first codon of the HEK5 receptor.

The resulting HEK5 extracellular domain was cloned into pDSRα after digestion with SalI and XbaI and transfected into CHO cells for expression.

HEK8 extracellular domain was amplified from a human fetal brain cDNA library by PCR using primers 5' and 3' to the extracellular domain coding region. For HEK8, the primers (SEQ ID NO: 31)

5' GAATTCGTCGACCCGGCGAACCATGGCTGGGAT and (SEQ ID NO: 32)

5' GAATTCTCTAGATTATCATGTGGAGTTAGCCCCATCTC were used to amplify the extracellular domain and to provide restriction sites for cloning into plasmid pDSRα.

The resulting HEK8 extracellular domain was cloned into pDSRa after digestion with SalI and XbaI and transferred CHO cells for expression.

HEK7 extracellular domain was amplified from a human fetal brain cDNA library by PCR using primers 5' and 3' to the extracellular domain coding region. For HEK7, the primers 5' TTCGCCCTATTTTCGTGTCTCTTCGGGATTTGCGACGCTCTCCGGACCCTCCTGGCCCAGC (SEQ ID NO: 33) and

5' GAATTCTCTAGATTATCACTGGCTTTGATCGCTGGAT (SEQ ID NO: 34)

were used to amplify the extracellular domain. In addition, the following primers were used to provide a translational start site, the HEK8 receptor signal peptide sequence, and restriction site for cloning into plasmid pDSRα.

5' GAATTCGTCGACCCGGCGAACCATGGCTGGGATTTTCTATTTCGCCCTACTTTCGTGTCT (SEQ ID NO: 35)

5' GAATTCTCTAGATTATCACTGGCTTTGATCGCTGGAT (SEQ ID NO: 36)

The resulting construct resulted in fusion of DNA incoding HEK8 signal sequence Met-Ala-Gly-Ile-Phe- Tyr-Phe-Ala-Leu-Phe-Ser-Cys-Leu-Phe-Gly-Ile-Cys-Asp SEQ ID NO: 37 to the first codon of the HEK7 receptor.

The resulting HEK7 extracellular domain was cloned into pDSRα after digestion with SalI and XbaI and transfected into CHO cells for expression.

EXAMPLE 4

Antibodies to HEK Receptors

Antibodies to HEK receptor proteins were generated which recognize the extracellular domain by using bacterial fusion proteins as the antigen. Antibodies were also generated which recognize the cytoplasmic domain by using synthetic peptides as the antigen.

The methodology employed has been previously described (Harlow and Lane, In *Antibodies: A Laboratory Manual.* 1988). For the extracellular domain antibodies, cDNAs were inserted into the pATH vector (see Table 4 for the regions of each receptor encoded by this construct). These constructs were expressed in bacteria and the resultant TrpE-fusion proteins were purified by SDS-polyacrylamide gel electrophoresis. For the cytoplasmic domain anti-peptide antibodies, peptides were synthesized (see Table 4 for the sequences) and covalently coupled to keyhole limpet hemocyanin. The fusion proteins and coupled peptides were used as antigens in rabbits and antisera were generated and characterized as described (Harlow and Lane, 1988). Anti-peptide antibodies were affinity purified by using a SulfoLink kit (Pierce, Rockford Ill.).

TABLE 4

HEK Receptor Antigens

| Receptor | Peptide Sequences | Amino Acids in Fusion Protein |
| --- | --- | --- |
| HEK4 | CLETQSKNGPVPV (SEQ ID NO: 38) | 22–159 |
| HEK5 | CRAQMNQIQSVEV (SEQ ID NO: 39) | 31–168 |
| HEK7 | CMKVQLVNGMVPL (SEQ ID NO: 40) | 335–545 |
| HEK8 | CMRTQMQQMHGRMVPV (SEQ ID NO: 41) | 27–188 |
| HEK11 | CQMLHLHGTGIQV (SEQ ID NO: 42) | 187–503 |

EXAMPLE 5

HEK/TrkB Chimeric Receptors

1. Generation of pSJA1 encoding rat trkB cytoplasmic domain.

All of the chimeric receptors are composed of the extracellular domain and the transmembrane region of one of the HEK receptors and the intracellular portion of rat trkB. To simplify each individual construction, an intermediate or parental plasmid, called RtrkB/AflII (or pSJA1), was generated. First, without altering the coded peptide sequence, an AflII site (CTTAAG) was introduced into position 2021 (cytosine at position 2021 (C2021) to guanine at position 2026 (G2026, CTCAAG) of the rat trkB cDNA (Middlemas, et al., Mol. Cell. Biol. 11, 143–153 (1991)) by PCR aided mutagenesis. Briefly, PCR primers were synthesized based on the rat trkB cDNA sequence. Primer I encompassed C2003 to G2034 of the cDNA. This primer contained two mutations, a cytosine to thymine(T) substitution at position 2023 (C2023T) and an insertion of an adenine(A) in between T2013 and G2014. These mutations created the AflII site at position C2021 and an additional XhoI site flanking the AflII site. Primer II was in the reverse direction encompassing T2141 to A2165 of the cDNA which bore an ApaI site. The PCR fragment produced with these primers and the rat trkB cDNA template was digested with XhoI and ApaI enzymes and sub cloned into the XhoI and ApaI sites of an expression vector, pcDNA3 (InVitroGen), to generate pSJA1-b. Following, pSJA1-b was linearized with ApaI and ligated with a BanII digested rat trkB cDNA fragment (G2151 to G4697) to reconstitute a larger fragment (C2021 to G4697) including the coding sequence of the whole intracellular domain of the rat trkB protein (L442 to G790) and 1571 residues (A3131 to G4697) of the 1627 nucleotide 3'-end non-coding region of the cDNA.

2. Generation of HEK8/rat trkB (pSJA5) chimera.

HEK8/rat trkB chimera was generated with a similar strategy as mentioned above. A SalI/BsaI cDNA fragment was first isolated from plasmid TK10/FL13. This fragment included the nucleotide sequence from the beginning to T1689 of the HEK8 cDNA (FIG. 3). Then, a pair of oligonucleotides was synthesized based on the HEK8 cDNA sequence. The sequence of the first oligonucleotide was the same as G1690 to C1740 of the Hek8 cDNA, with an additional C residue added to its 3'-end. The second oligonucleotide was in the reverse orientation of the HEK8 cDNA. It contained C1694 to C1740 of the HEK8 cDNA sequence and an additional five residue motif, TTAAG, at its 5'-end. These two oligonucleotides were kinased and annealed with equal molar ratio, to create a double strand DNA fragment with the sequence of G1690 to C1740 of the HEK8 cDNA and with the BsaI and the AflII cohesive ends at its 5' and 3' ends, respectively. This fragment was ligated together with the SalI/BsaI cDNA fragment into XhoI/AflII linearized pSJA1 to generate the HEK8/RtrkB (pSJA5) chimerical construct.

3. Generation of HEK11/rat trkB (pSJA6) chimera.

To generate the HEK11/rat trkB chimera, a SalI/AccI fragment covering the sequence of nucleotide C1 to T1674 of the HEK11 cDNA (FIG. 4) was first isolated from plasmid TK19T3. Then, a pair of oligonucleotides was synthesized based on the HEK11 cDNA sequence. The first oligonucleotide had the same sequence as from nucleotide A1666 to T1691 of the HEK11 cDNA, which contained the AccI site. The second oligonucleotide was in the reverse orientation of the HEK11 cDNA. It encompassed G1895 to T1919 of the HEK11 cDNA sequence. An additional ten residue motif, SEQ ID NO: 43 was added to the 5'-end of this oligonucleotide to introduce an AflII site, which would be used to link the external domain and the transmembrane region of the HEK11 receptor to the intracellular domain of the rat trkB cDNA cloned in pSJA1 in the same reading frame. PCR was performed with these oligonucleotides as primers and the HEK11 cDNA as template. The PCR fragment was digested with AccI and AflII enzymes and ligated with the SalI/AccI cDNA fragment and the XhoI/AflII linearized pSJA1 to generate the HEK11/rat trkB (pSJA6) chimerical construct.

EXAMPLE 6

Tissue Distribution of HEK Receptors

The distribution of mRNA expression for HEK4, HEK5, HEK7, HEK8 and HEK11 receptors in human and rat tissues was examined by Northern blot hybridization.

Rat total RNA was prepared from tissues using the method of Chomczynski and Sacchi (Anal. Biochem 162, 156–159 (1987)). The RNA was separated by formaldehyde-agarose electrophoresis and transferred to Hybond-N membranes (Amersham, Arlington Heights, Ill.) using 20×SSC (Maniatis et al. 1982). The membrane was dried at 80° C. in vacuo for 30 minutes, then crosslinked for 3 minutes on a UV transilluminator (Fotodyne, New Berlin, Wis.). The membrane was prehybridized for 2 hours at 42° C. in 50% formamide, 5× SSPE, 5× Denhardt's, 0.2% SDS, and 100 µg/ml denatured herring sperm DNA (Maniatis et al. 1982). Northern blots of human tissue were purchased from Clontech (Palo Alto, Calif.). Probes were prepared by labeling the fragment of cDNA which encoded the extracellular domain of the receptor with $^{32}$P-dCTP using a hexanucleotide random priming kit (Boehringer Mannheim, Indianapolis, Ind.) to a specific activity of at least $1 \times 10^9$ cpm/ug. The probe was hybridized to the membrane at a concentration of 1–5 ng/ml at 42° C. for 24 to 36 hours in a buffer similar to the prehybridization buffer except that 1× Denhardt's was used. After hybridization, the membranes were washed 2 times for 5 minutes each in 2×SSC, 0.1% SDS at room temperature followed by two 15 minute washes in 0.5×SSC, 0.1% SDS at 55° C. Blots were exposed for 1–2 weeks using Kodak XAR film (Kodak, Rochester, N.Y.) with a Dupont Lightning Plus intensifying screen. The results are shown in FIGS. 7–11.

Figure 7A:
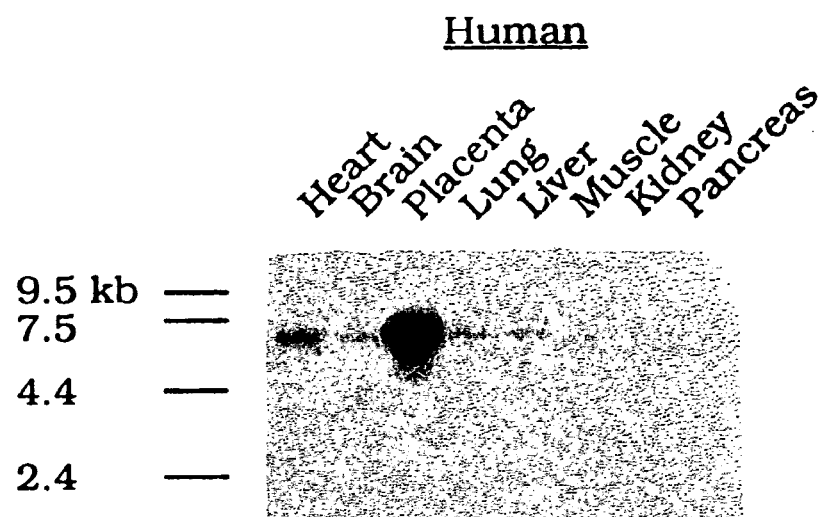
FIGS. 7–11 show Northern blot analyses of the tissue distribution of the HEK receptors. Receptor cDNA probes, labeled with $^{32}P$, were hybridized to either 2 µg of poly A$^+$ RNA from human tissues (panel A, Clontech) or 10 µg of total RNA from rat tissues (panel B). Sizes of the transcripts were determined by comparison with RNA molecular weight markers (Bethesda Research Labs, Gaithersburg, Md.).
Figure 7B:
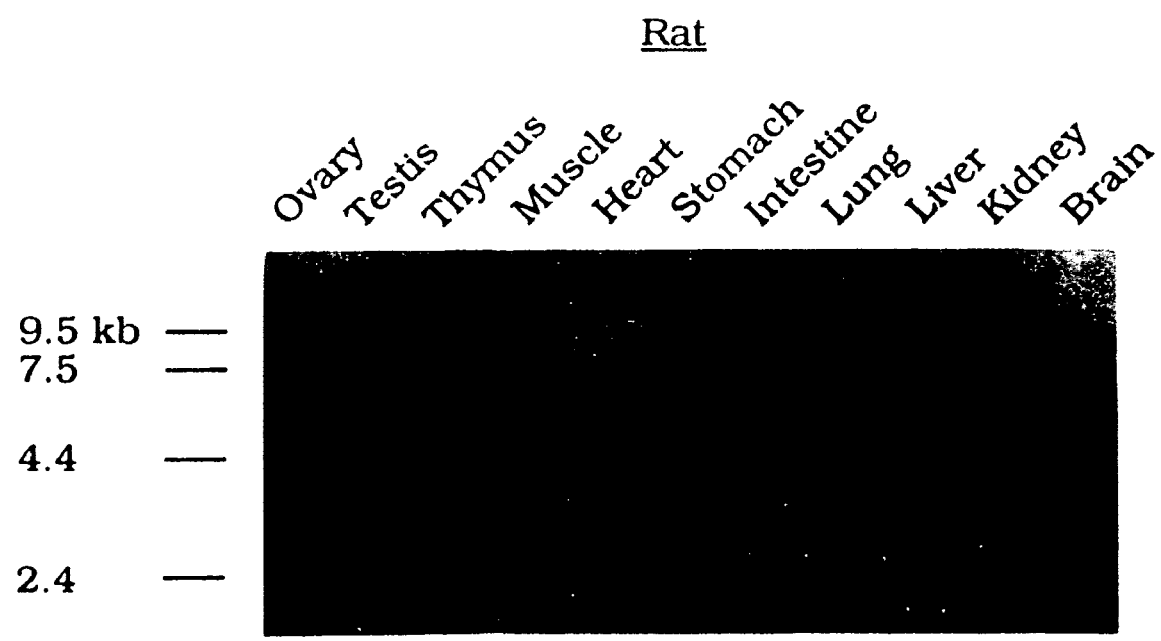

Homologs for HEK4 have been previously identified from mouse, chicken, and rat. In the adult mouse, expression is detected primarily in the brain and testis (Sajjadi et al. 1991). A slightly different pattern was found in adult chicken tissues, with the main sources of expression being the brain, liver, and kidney. Lower levels of expression were detectable in the lung and heart (Marcelle & Eichmann, Oncogene 1, 2479–2487 (1992)). A fragment of the Rek4 gene (tyro-4) has been isolated and used to look at tissue expression in the adult rat (Sajjadi et al. 1991). The brain was the only tissue that expressed Rek4 mRNA. However, RNA from lung or testis were not examined. Previous studies on HEK4 only looked at the expression of the mRNA in cell lines, where it was found in one pre-B cell line and two T-cell lines (Wicks et al. 1992). The significance of this with regard to in vivo expression remains to be determined. In this study we have looked at the HEK4 expression in human tissues, and also the expression of Rek4 in rat tissues. The HEK4 mRNA corresponds to a single transcript with a size of about 7 kb (FIG. 7A). HEK4 mRNA was most abundantly expressed in placenta, with lower levels present in heart, brain, lung, and liver. On prolonged exposures, trace amounts of mRNA were detectable in kidney and pancreas. Expression in the rat was more similar to that detected in the mouse and chicken. Rek4 was expressed at the lowest levels of any of the family members characterized herein. A transcript of about 7 kb was detectable in rat lung, with a lower amount detectable in brain (FIG. 7B). Also, a 4 kb transcript was expressed in rat testis. Because the transcripts were barely detectable using total RNA, some of the other rat tissues may contain amounts of Rek4 below the level of detection.

Figure 8A:
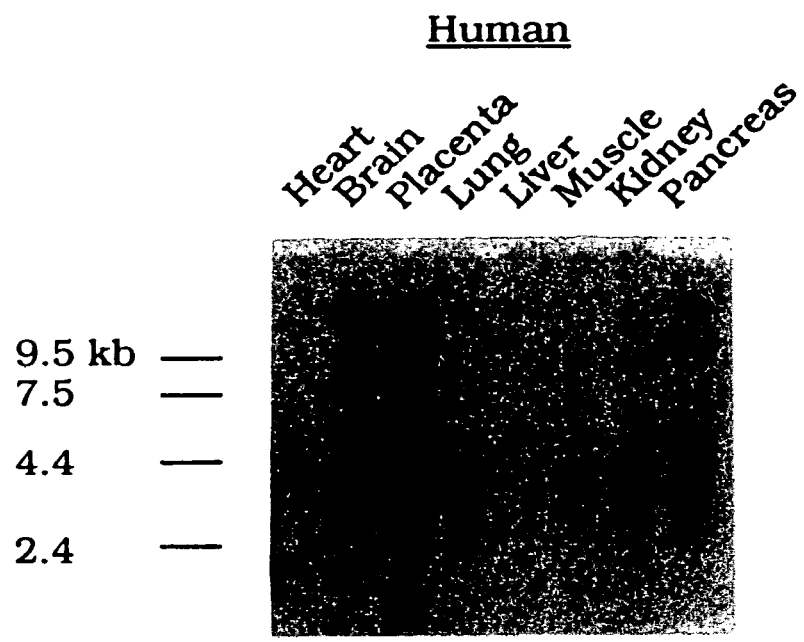
Figure 8B:
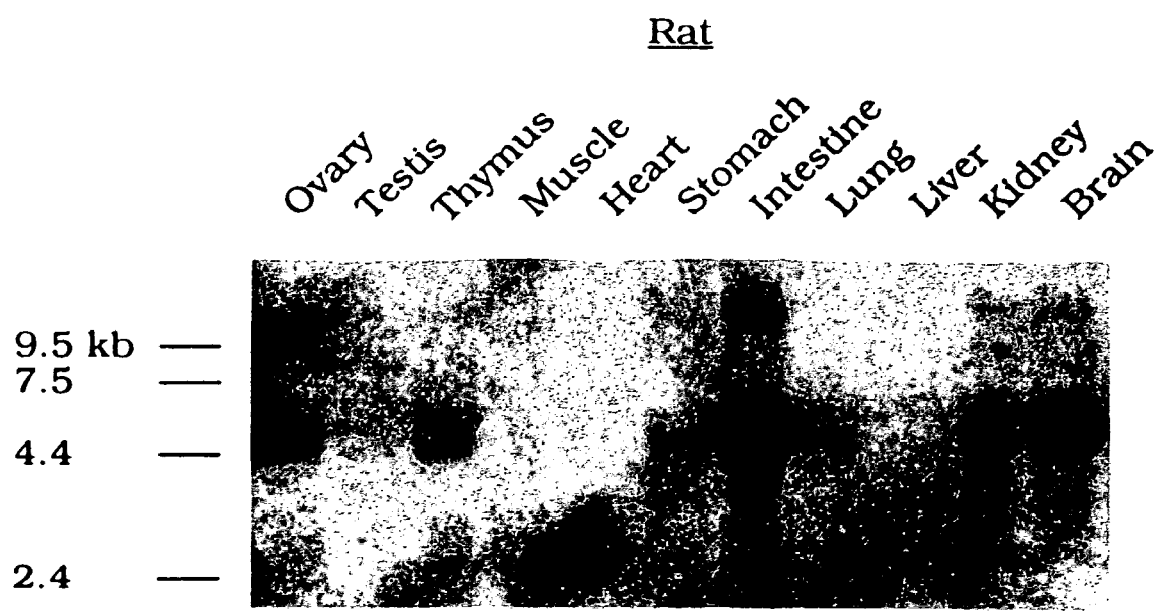

The expression of HEK5 in adult tissues has been previously studied in chicken and rat. Studies in the chicken have identified the Cek5 protein in the brain and liver, with a smaller protein detected in the intestine. In the rat, the tyro-5 fragment detected mRNA expression only in the adult brain, though intestine was not examined (Lai and Lemke, 1991). Our results show that HEK5 mRNA was expressed at much higher levels than HEK4 and was found as transcripts of several sizes. The most abundant mRNAs were of approximately 4.0 and 4.4 kb, with lesser amounts of higher molecular weight transcripts of 9.5 kb and longer (FIG. 8A). The HEK5 mRNA was most abundantly expressed in placenta, but was also highly expressed in brain, pancreas, kidney, muscle, and lung. Longer exposures of the blots revealed the presence of transcripts in heart and liver as well. The rat homolog of HEK5 (Rek5) showed a somewhat similar pattern of expression. Rek5 was most abundant in intestine, followed by brain, kidney, lung, thymus, stomach, and ovary (FIG. 8B). Expression was not detectable in testis, muscle, heart, or liver. During our analysis of this family, we concluded that the rat Erk fragment (Chan & Watt, 1991) likely encodes a portion of the Rek5 receptor. Erk expression was examined in several rat tissues and found only in the lung. The reason for the discrepancy between that report and what we and others (Lai & Lemke, 1991) have found is unclear.

Figure 10A:
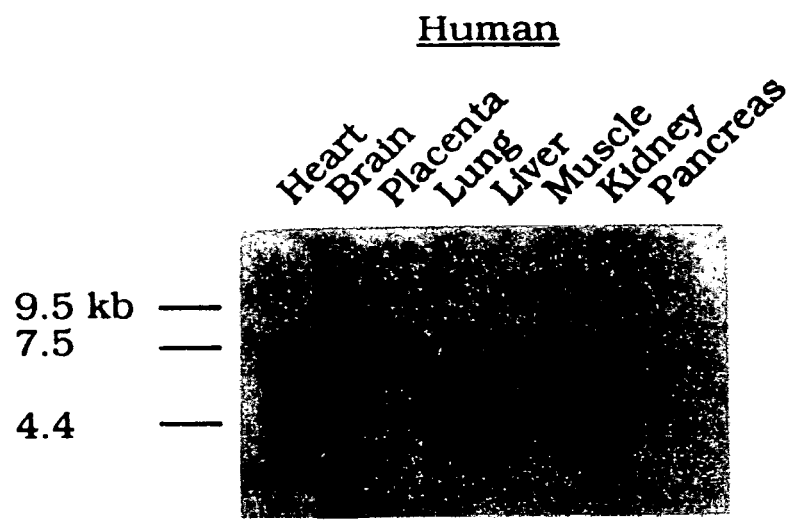
Figure 10B:
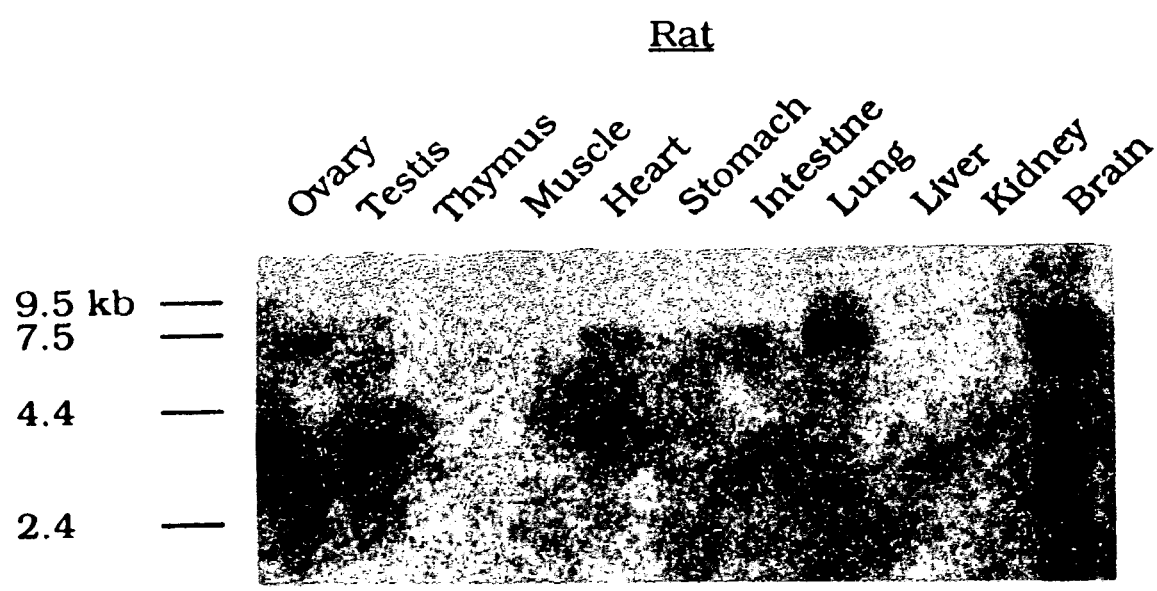

Homologs for HEK8 have been identified from chicken, mouse, and rat. In the adult chicken, a single Cek8 transcript was found to be expressed at high levels in the brain, with expression also detected in the kidney, lung, muscle, and thymus. The expression of the mouse homolog of HEK8, Sek, has been detected as a single transcript with abundant expression in the adult brain and lower expression in the heart, lung and kidney. A fragment of Rek8 (tyro-1) was used to look at expression in rat tissues, with expression found only in the brain (Lai & Lemke, 1991). We found that HEK8 mRNA was expressed at levels comparable to that of HEK5. Multiple transcripts were also observed, the most abundant at 7 kb and 5 kb. The highest level of mRNA expression was seen in the brain, although substantial levels were detected in other tissues including heart, lung, muscle, kidney, placenta, and pancreas. Expression in liver was much lower than in the other tissues. The only difference in expression patterns between human and mouse was expression in human muscle, also seen for Cek8 in chicken. Among the rat tissues, Rek8 was most highly expressed in the brain, followed by the lung, heart, and testis (FIG. 10B). In contrast to HEK8, expression of Rek8 appeared to be lower in muscle and kidney, two tissues where HEK8 was readily detectable. In addition, Rek8 was not expressed as a 5.0 kb transcript, as it was not visible even on prolonged exposures.

Figure 9A:
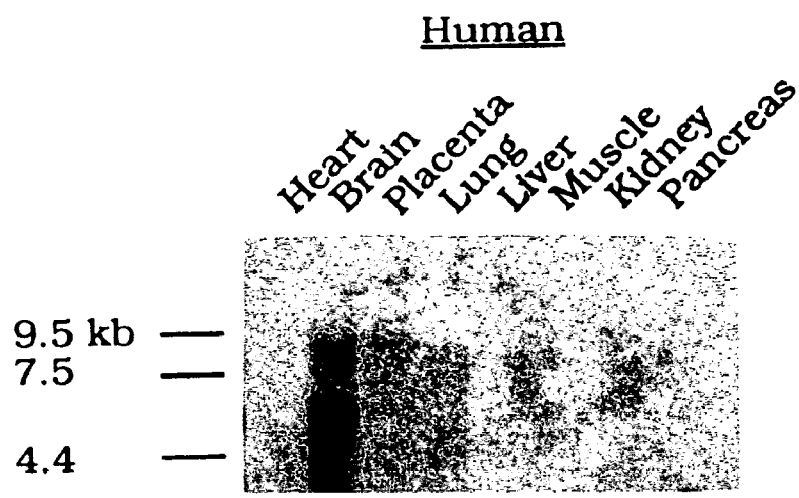
Figure 9B:
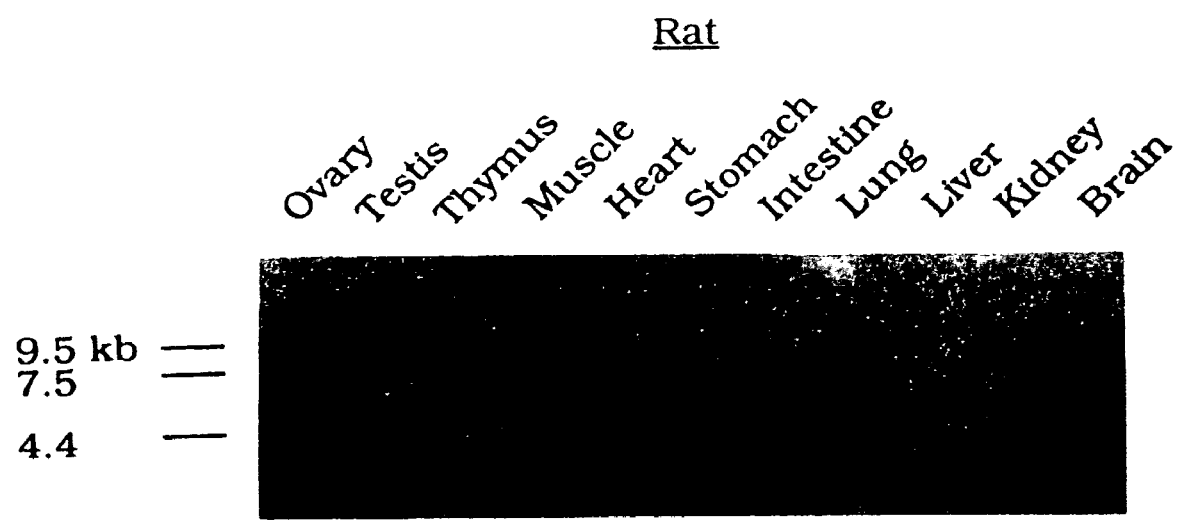

During the analysis of this family, we deduced that HEK7 is the human homolog of Cek7. The only expression seen in adult chicken was an 8.5 kb transcript found in the brain (Sajjadi & Pasquale, 1993). Of the five EPH sub-family members described here, HEK7 was the most restricted in its expression pattern. Analysis of human mRNA revealed significant expression only in the brain, with a much lower level detectable in the placenta (FIG. 9A). Prolonged exposures did not reveal expression in any other tissue examined. Two prominent transcripts were found in brain, the most highly expressed with a size of 6 kb and the other with a length of 9 kb. In the placenta, however, only the 9 kb transcript was detected. Rek7 mRNA was expressed in a pattern similar to HEK7. The highest level of expression was found in brain, with a much lower level in ovary (FIG. 9B). The transcripts were of similar size as for HEK7, with the 6 kb transcript detected only in brain.

Figure 11A:
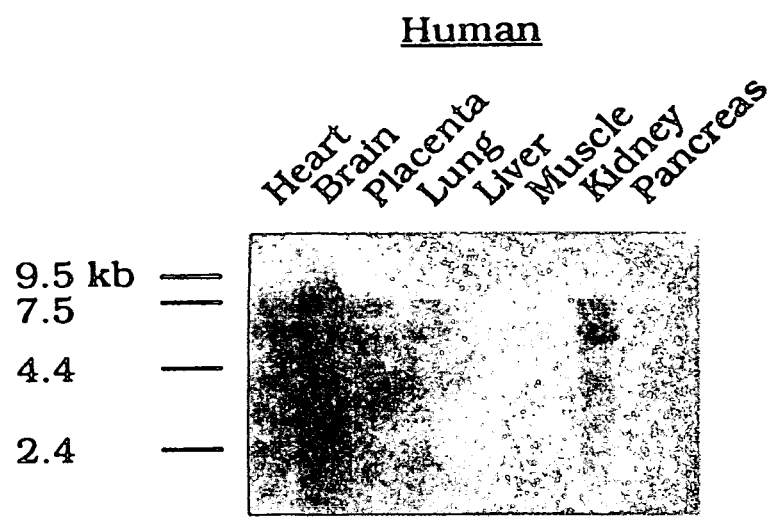
Figure 11B:
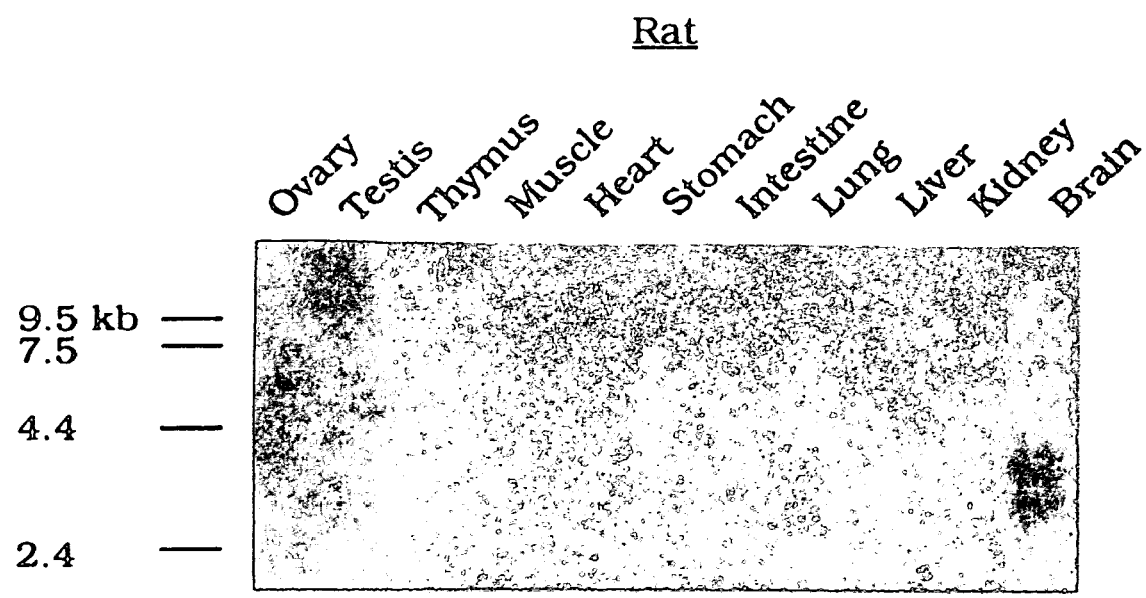

HEK11 was expressed as several transcripts, with major mRNAs of length 7.5, 6.0 and 3.0 kb and minor transcripts of 4.4 and 2.4 kb (FIG. 11A). All five mRNAs were expressed at the highest levels in brain, followed by heart. Placenta, lung and kidney had significant amounts of four of the five transcripts, with lower expression seen in muscle. Pancreas had barely detectable amounts of HEK11 mRNA, while liver had no detectable HEK11 transcript. Rek11 had a similar pattern of expression, with four transcripts (10, 7.5, 3.5 and 3.0 kb) detected in brain (FIG. 11B).

The relative level of mRNA expression for each of the five receptors in all tissues studied is summarized in Table 5.

TABLE 5

Tissue Distribution of HEK Receptors

|  | HEK4 | HEK5 | HEK7 | HEK8 | HEK11 |
|---|---|---|---|---|---|
| Human |  |  |  |  |  |
| Brain | ++ | ++ | ++ | +++ | ++ |
| Heart | + | + | bd | ++ | + |
| Kidney | + | + | bd | + | + |
| Liver | + | + | bd | + | bd |
| Lung | + | + | bd | ++ | + |
| Muscle | + | + | bd | ++ | + |
| Pancreas | + | ++ | bd | + | bd |
| Placenta | +++ | +++ | bd | ++ | + |
| Rat |  |  |  |  |  |
| Brain | + | ++ | +++ | +++ | ++ |
| Heart | bd | bd | bd | + | bd |
| Intestine | bd | +++ | bd | bd | bd |
| Kidney | bd | ++ | bd | bd | bd |
| Liver | bd | bd | bd | bd | bd |
| Lung | + | + | bd | ++ | bd |
| Muscle | bd | bd | bd | bd | bd |
| Ovary | bd | + | + | bd | bd |
| Stomach | bd | + | bd | bd | bd |
| Testis | + | bd | bd | + | bd |
| Thymus | bd | + | bd | bd | bd | bd = below detection

The transcripts for HEKs 4,5,8, and 11 were rather widely distributed in human tissue while REK7 was specific for brain. Expression patterns between rat and human tissue were roughly comparable given that the rat blots were less sensitive due to the use of total RNA rather than polyA$^+$. As was found for the Cek mRNAs by Sajjadi and Pasquale (Sajjadi & Pasquale, 1993), often there were several different size transcripts detected for a single receptor. The size distribution of the transcripts appears to be both tissue and species specific. Previous work has shown that the smaller transcript of Mek4 encodes a potentially secreted receptor (Sajjadi et al. 1991).

The following sections describe Materials and Methods used to carry out experiments described in Example 1.

Isolation, Cloning and Sequencing of HEK Receptor cDNAs

Fragments containing a portion of the catalytic domain of EPH sub-family receptors were generated using a polymerase chain reaction (PCR) with disrupted phage from a human fetal brain cDNA library as a template. A 10 µl aliquot of the cDNA library (Stratagene, La Jolla, Calif.) was treated at 70° C. for 5 minutes to disrupt the phage particles, then cooled on wet ice. The disrupted phage were added to 10 µl of 10× Taq polymerase buffer, 8ul of 2 mM each dNTP, 100 picomoles of each primer, and 1.5 µl of Taq polymerase (Promega, Madison, Wis.) in a total volume of 100 µl. The reaction was run for 35 cycles, each consisting of 1 minute at 96° C., 1 minute at 50° C., and 2 minutes at 72° C. A 5 minute, 72° C. incubation was added at the end to ensure complete extension. The primers used were degenerate mixtures of oligonucleotides based on amino acid sequences which are highly conserved among EPH sub-family members.

5'AGGGAATTCCAYCGNGAYYTNGCNGC' (SEQ ID NO: 27);

5'AGGGGATCCRWARSWCCANACRTC' (SEQ ID NO: 28).

The products of the PCR reaction were digested with EcoRI and BamHI and cloned into M13 mp19 (Messing, Methods Enzymol. (1983)) for sequence analysis. The five clones which were identified as fragments of EPH receptor sub-family members were labeled with $^{32}$P-dCTP by random priming and each was used to screen Genescreen nitrocellulose filters (NEN, Boston, Mass.) containing plaques from the human fetal brain cDNA library. Phage stocks prepared from positively screening plaques were plated and rescreened with the same probe in order to obtain single clones. cDNA inserts were transferred into pBluescript using the in vivo excision protocol supplied with the cDNA library (Stratagene, La Jolla, Calif.). Nucleotide sequences were determined using Taq DyeDeoxy Terminator Cycle Sequencing kits and an Applied Biosystems 373A automated DNA sequencer (Applied Biosystems, Foster City, Calif.).

5' Race

The 5' ends of the cDNAs were isolated using a 5' RACE kit (GIBCO/BRL, Gaithersburg, Md.) following the manufacturer's instructions. Excess primers were removed after first strand cDNA synthesis using ultrafree-MC cellulose filters (30,000 molecular weight cutoff, Millipore, Bedford, Mass.). Amplified PCR products were digested with the appropriate restriction enzymes, separated by agarose gel electrophoresis, and purified using a Gen clean kit (Bio101, La Jolla, Calif.). The purified PCR product was ligated into the plasmid vector pUC19 (Yanisch-Perron et al. Gene 33, 103–119 (1985)) which had been digested with appropriate restriction enzymes and the ligation mixture was introduced into host bacteria by electroporation. Plasmid DNA was prepared from the resulting colonies. Those clones with the largest inserts were selected for DNA sequencing.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A monoclonal antibody or fragment thereof that binds a polypeptide consisting of amino acids 1 to 524 of SEQ ID NO: 11.

2. The antibody or fragment thereof of claim 1, which is a chimeric antibody or a chimeric antibody fragment.

3. The antibody or fragment thereof of claim 1, which is a CDR-grafted antibody or a CDR-grafted antibody fragment.

4. A composition comprising an antibody or fragment thereof of claim 1 in a mixture with an adjuvant, carrier, solubilizer, or diluent.

5. A monoclonal antibody or fragment thereof which is raised against a polypeptide comprising amino acids 1 to 524 of SEQ ID NO: 11, wherein the antibody or fragment thereof binds the polypeptide comprising amino acids 1 to 524 of SEQ ID NO: 11.

6. The antibody or fragment thereof of claim 5 which is a chimeric antibody or a chimeric antibody fragment.

7. The antibody or fragment thereof of claim 5 which is a CDR-grafted antibody or a CDR-grafted antibody fragment.

8. A composition comprising an antibody or fragment thereof of claim 5 in a mixture with an adjuvant, carrier, solubilizer, or diluent.

* * * * *

UNITED STATES PATENT AND TRADEMARK OFFICE
CERTIFICATE OF CORRECTION

PATENT NO. : 6,992,175 B1
APPLICATION NO. : 09/378759
DATED : April 17, 2006
INVENTOR(S) : Gary M. Fox et al.

Page 1 of 1

It is certified that error appears in the above-identified patent and that said Letters Patent is hereby corrected as shown below:

<u>Title page,</u>
Item [54], Title, "NUCLEIC ACIDS ENCODING EPH-LIKE RECEPTOR TYROSINE KINASES" should read -- ANTIBODIES TO EPH-LIKE RECEPTOR TYROSINE KINASES --.

Signed and Sealed this

Twentieth Day of June, 2006

JON W. DUDAS
*Director of the United States Patent and Trademark Office*

UNITED STATES PATENT AND TRADEMARK OFFICE
CERTIFICATE OF CORRECTION

PATENT NO.      : 6,992,175 B1                                    Page 1 of 1
APPLICATION NO. : 09/378759
DATED           : January 31, 2006
INVENTOR(S)     : Gary M. Fox et al.

It is certified that error appears in the above-identified patent and that said Letters Patent is hereby corrected as shown below:

Title page,
Item [54], Title, "NUCLEIC ACIDS ENCODING EPH-LIKE RECEPTOR TYROSINE KINASES" should read -- ANTIBODIES TO EPH-LIKE RECEPTOR TYROSINE KINASES --.

This certificate supersedes certificate of correction issued June 20, 2006.

Signed and Sealed this

Twenty-ninth Day of August, 2006

JON W. DUDAS
*Director of the United States Patent and Trademark Office*

```
                            SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Trp Thr Ala Pro Glu Ala Ile
1               5

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Val Cys Lys Val Ser Asp Phe Gly
1               5

(2) INFORMATION FOR SEQ ID NO:3:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Val Cys Lys Val Ser Asp Phe Gly Leu Ser Arg Tyr Leu Gln Asp Asp
1               5                   10                  15

Thr Ser Asp Pro Thr Tyr Thr Ser Ser Leu Gly Gly Lys Ile Pro Val
            20                  25                  30

Arg Trp Thr Ala Pro Glu Ala Ile
        35                  40

(2) INFORMATION FOR SEQ ID NO:4:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:
```

```
Val Cys Lys Val Ser Asp Phe Gly Leu Ser Arg Val Leu Glu Asp Asp
1               5                   10                  15

Pro Glu Ala Ala Tyr Thr Thr Arg Gly Gly Lys Ile Pro Ile Arg Trp
            20                  25                  30

Thr Ala Pro Glu Ala Ile
            35
```

(2) INFORMATION FOR SEQ ID NO:5:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Val Cys Lys Val Ser Asp Phe Gly Leu Ser Arg Phe Leu Glu Asp Asp
1               5                   10                  15

Thr Ser Asp Pro Thr Tyr Thr Ser Ala Leu Gly Gly Lys Ile Pro Ile
            20                  25                  30

Arg Trp Thr Ala Pro Glu Ala Ile
            35                  40
```

(2) INFORMATION FOR SEQ ID NO:6:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Val Cys Lys Val Ser Asp Phe Gly Met Ser Arg Val Leu Glu Asp Asp
1               5                   10                  15

Pro Glu Ala Ala Tyr Thr Thr Arg Gly Gly Lys Ile Pro Ile Arg Trp
            20                  25                  30

Thr Ala Pro Glu Ala Ile
            35
```

(2) INFORMATION FOR SEQ ID NO:7:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Val Cys Lys Val Ser Asp Phe Gly Leu Ser Arg Val Ile Glu Asp Asp
1               5                   10                  15

Pro Glu Ala Val Tyr Thr Thr Thr Gly Gly Lys Ile Pro Val Arg Trp
            20                  25                  30

Thr Ala Pro Glu Ala Ile
            35
```

(2) INFORMATION FOR SEQ ID NO:8:

```
    (i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Val Cys Lys Val Ser Asp Phe Gly Leu Ala Arg Leu Ile Glu Asp Asn
1               5                   10                  15

Glu Tyr Thr Ala Arg Gln Gly Ala Lys Phe Pro Ile Lys Trp Thr Ala
            20                  25                  30

Pro Glu Ala Ile
        35

(2) INFORMATION FOR SEQ ID NO:9:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Val Cys Lys Val Ser Asp Phe Gly Leu Ala Arg Asp Ile Met Arg Asp
1               5                   10                  15

Ser Asn Tyr Ile Ser Lys Gly Ser Thr Phe Leu Pro Leu Lys Trp Thr
            20                  25                  30

Ala Pro Glu Ala Ile
        35

(2) INFORMATION FOR SEQ ID NO:10:

(i) SEQUENCE CHARACTERISTICS:
        (A) LENGTH: 2962 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2913

(xi) SEQUENCE DESCRIPTION: SEQ ID NO:10:

CTG CTC GCC GCC GTG GAA GAA ACG CTA ATG GAC TCC ACT ACA GCG ACT        48
Leu Leu Ala Ala Val Glu Glu Thr Leu Met Asp Ser Thr Thr Ala Thr
1               5                   10                  15

GCT GAG CTG GGC TGG ATG GTG CAT CCT CCA TCA GGG TGG GAA GAG GTG        96
Ala Glu Leu Gly Trp Met Val His Pro Pro Ser Gly Trp Glu Glu Val
            20                  25                  30

AGT GGC TAC GAT GAG AAC ATG AAC ACG ATC CGC ACG TAC CAG GTG TGC       144
Ser Gly Tyr Asp Glu Asn Met Asn Thr Ile Arg Thr Tyr Gln Val Cys
        35                  40                  45

AAC GTG TTT GAG TCA AGC CAG AAC AAC TGG CTA CGG ACC AAG TTT ATC       192
Asn Val Phe Glu Ser Ser Gln Asn Asn Trp Leu Arg Thr Lys Phe Ile
    50                  55                  60

CGG CGC CGT GGG GCC CAC CGC ATC CAC GTG GAG ATG AAG TTT TCG GTG       240
Arg Arg Arg Gly Ala His Arg Ile His Val Glu Met Lys Phe Ser Val
65                  70                  75                  80

CGT GAC TGC AGC AGC ATC CCC AGC GTG CCT GGC TCC TGC AAG GAG ACC       288
```

```
                                        -continued

Arg Asp Cys Ser Ser Ile Pro Ser Val Pro Gly Ser Cys Lys Glu Thr
             85              90              95

TTC AAC CTC TAT TAC TAT GAG GCT GAC TTT GAC TCG GCC ACC AAG ACC          336
Phe Asn Leu Tyr Tyr Tyr Glu Ala Asp Phe Asp Ser Ala Thr Lys Thr
            100             105             110

TTC CCC AAC TGG ATG GAG AAT CCA TGG GTG AAG GTG GAT ACC ATT GCA          384
Phe Pro Asn Trp Met Glu Asn Pro Trp Val Lys Val Asp Thr Ile Ala
            115             120             125

GCC GAC GAG AGC TTC TCC CAG GTG GAC CTG GGT GGC CGC GTC ATG AAA          432
Ala Asp Glu Ser Phe Ser Gln Val Asp Leu Gly Gly Arg Val Met Lys
130             135             140

ATC AAC ACC GAG GTG CGG AGC TTC GGA CCT GTG TCC CGC AGC GGC TTC          480
Ile Asn Thr Glu Val Arg Ser Phe Gly Pro Val Ser Arg Ser Gly Phe
145             150             155             160

TAC CTG GCC TTC CAG GAC TAT GGC GGC TGC ATG TCC CTC ATC GCC GTG          528
Tyr Leu Ala Phe Gln Asp Tyr Gly Gly Cys Met Ser Leu Ile Ala Val
            165             170             175

CGT GTC TTC TAC CGC AAG TGC CCC CGC ATC ATC CAG AAT GGC GCC ATC          576
Arg Val Phe Tyr Arg Lys Cys Pro Arg Ile Ile Gln Asn Gly Ala Ile
            180             185             190

TTC CAG GAA ACC CTG TCG GGG GCT GAG AGC ACA TCG CTG GTG GCT GCC          624
Phe Gln Glu Thr Leu Ser Gly Ala Glu Ser Thr Ser Leu Val Ala Ala
            195             200             205

CGG GGC AGC TGC ATC GCC AAT GCG GAA GAG GTG GAT GTA CCC ATC AAG          672
Arg Gly Ser Cys Ile Ala Asn Ala Glu Glu Val Asp Val Pro Ile Lys
210             215             220

CTC TAC TGT AAC GGG GAC GGC GAG TGG CTG GTG CCC ATC GGG CGC TGC          720
Leu Tyr Cys Asn Gly Asp Gly Glu Trp Leu Val Pro Ile Gly Arg Cys
225             230             235             240

ATG TGC AAA GCA GGC TTC GAG GCC GTT GAG AAT GGC ACC GTC TGC CGA          768
Met Cys Lys Ala Gly Phe Glu Ala Val Glu Asn Gly Thr Val Cys Arg
            245             250             255

GGT TGT CCA TCT GGG ACT TTC AAG GCC AAC CAA GGG GAT GAG GCC TGT          816
Gly Cys Pro Ser Gly Thr Phe Lys Ala Asn Gln Gly Asp Glu Ala Cys
            260             265             270

ACC CAC TGT CCC ATC AAC AGC CGG ACC ACT TCT GAA GGG GCC ACC AAC          864
Thr His Cys Pro Ile Asn Ser Arg Thr Thr Ser Glu Gly Ala Thr Asn
            275             280             285

TGT GTC TGC CGC AAT GGC TAC TAC AGA GCA GAC CTG GAC CCC TTG GAC          912
Cys Val Cys Arg Asn Gly Tyr Tyr Arg Ala Asp Leu Asp Pro Leu Asp
            290             295             300

ATG CCC TGC ACA ACC ATC CCC TCC GCG CCC CAG GCT GTG ATT TCC AGT          960
Met Pro Cys Thr Thr Ile Pro Ser Ala Pro Gln Ala Val Ile Ser Ser
305             310             315             320

GTC AAT GAG ACC TCC CTC ATG CTG GAG TGG ACC CCT CCC CGC GAC TCC         1008
Val Asn Glu Thr Ser Leu Met Leu Glu Trp Thr Pro Pro Arg Asp Ser
            325             330             335

GGA GGC CGA GAG GAC CTC GTC TAC AAC ATC ATC TGC AAG AGC TGT GGC         1056
Gly Gly Arg Glu Asp Leu Val Tyr Asn Ile Ile Cys Lys Ser Cys Gly
            340             345             350

TCG GGC CGG GGT GCC TGC ACC CGC TGC GGG GAC AAT GTA CAG TAC GCA         1104
Ser Gly Arg Gly Ala Cys Thr Arg Cys Gly Asp Asn Val Gln Tyr Ala
            355             360             365

CCA CGC CAG CTA GGC CTG ACC GAG CCA CGC ATT TAC ATC AGT GAC CTG         1152
Pro Arg Gln Leu Gly Leu Thr Glu Pro Arg Ile Tyr Ile Ser Asp Leu
            370             375             380

CTG GCC CAC ACC CAG TAC ACC TTC GAG ATC CAG GCT GTG AAC GGC GTT         1200
Leu Ala His Thr Gln Tyr Thr Phe Glu Ile Gln Ala Val Asn Gly Val
385             390             395             400
```

```
                                                            -continued

ACT GAC CAG AGC CCC TTC TCG CCT CAG TTC GCC TCT GTG AAC ATC ACC       1248
Thr Asp Gln Ser Pro Phe Ser Pro Gln Phe Ala Ser Val Asn Ile Thr
            405                 410                 415

ACC AAC CAG GCA GCT CCA TCG GCA GTG TCC ATC ATG CAT CAG GTG AGC       1296
Thr Asn Gln Ala Ala Pro Ser Ala Val Ser Ile Met His Gln Val Ser
        420                 425                 430

CGC ACC GTG GAC AGC ATT ACC CTG TCG TGG TCC CAG CCG GAC CAG CCC       1344
Arg Thr Val Asp Ser Ile Thr Leu Ser Trp Ser Gln Pro Asp Gln Pro
    435                 440                 445

AAT GGC GTG ATC CTG GAC TAT GAG CTG CAG TAC TAT GAG AAG GAG CTC       1392
Asn Gly Val Ile Leu Asp Tyr Glu Leu Gln Tyr Tyr Glu Lys Glu Leu
450                 455                 460

AGT GAG TAC AAC GCC ACA GCC ATA AAA AGC CCC ACC AAC ACG GTC ACG       1440
Ser Glu Tyr Asn Ala Thr Ala Ile Lys Ser Pro Thr Asn Thr Val Thr
465                 470                 475                 480

GGC CTC AAA GCC GGC GCC ATC TAT GTC TTC CAG GTG CGG GCA CGC ACT       1488
Gly Leu Lys Ala Gly Ala Ile Tyr Val Phe Gln Val Arg Ala Arg Thr
            485                 490                 495

GTG GCA GGC TAC GGG CGC TAC AGC GGC AAG ATG TAC TTC CAG ACC ATG       1536
Val Ala Gly Tyr Gly Arg Tyr Ser Gly Lys Met Tyr Phe Gln Thr Met
        500                 505                 510

ACA GAA GCC GAG TAC CAG ACA AGC ATC CAG GAG AAG TTG CCA CTC ATC       1584
Thr Glu Ala Glu Tyr Gln Thr Ser Ile Gln Glu Lys Leu Pro Leu Ile
    515                 520                 525

ATC GGC TCC TCG GCC GCT GGC CTG GTC TTC CTC ATT GCT GTG GTT GTC       1632
Ile Gly Ser Ser Ala Ala Gly Leu Val Phe Leu Ile Ala Val Val Val
530                 535                 540

ATC GCC ATC GTG TGT AAC AGA CGG GGG TTT GAG CGT GCT GAC TCG GAG       1680
Ile Ala Ile Val Cys Asn Arg Arg Gly Phe Glu Arg Ala Asp Ser Glu
545                 550                 555                 560

TAC ACG GAC AAG CTG CAA CAC TAC ACC AGT GGC CAC ATA ACC CCA GGC       1728
Tyr Thr Asp Lys Leu Gln His Tyr Thr Ser Gly His Ile Thr Pro Gly
            565                 570                 575

ATG AAG ATC TAC ATC GAT CCT TTC ACC TAC GAG GAC CCC AAC GAG GCA       1776
Met Lys Ile Tyr Ile Asp Pro Phe Thr Tyr Glu Asp Pro Asn Glu Ala
        580                 585                 590

GTG CGG GAG TTT GCC AAG GAA ATT GAC ATC TCC TGT GTC AAA ATT GAG       1824
Val Arg Glu Phe Ala Lys Glu Ile Asp Ile Ser Cys Val Lys Ile Glu
    595                 600                 605

CAG GTG ATC GGA GCA GGG GAG TTT GGC GAG GTC TGC AGT GGC CAC CTG       1872
Gln Val Ile Gly Ala Gly Glu Phe Gly Glu Val Cys Ser Gly His Leu
610                 615                 620

AAG CTG CCA GGC AAG AGA GAG ATC TTT GTG GCC ATC AAG ACG CTC AAG       1920
Lys Leu Pro Gly Lys Arg Glu Ile Phe Val Ala Ile Lys Thr Leu Lys
625                 630                 635                 640

TCG GGC TAC ACG GAG AAG CAG CGC CGG GAC TTC CTG AGC GAA GCC TCC       1968
Ser Gly Tyr Thr Glu Lys Gln Arg Arg Asp Phe Leu Ser Glu Ala Ser
            645                 650                 655

ATC ATG GGC CAG TTC GAC CAT CCC AAC GTC ATC CAC CTG GAG GGT GTC       2016
Ile Met Gly Gln Phe Asp His Pro Asn Val Ile His Leu Glu Gly Val
        660                 665                 670

GTG ACC AAG AGC ACA CCT GTG ATG ATC ATC ACC GAG TTC ATG GAG AAT       2064
Val Thr Lys Ser Thr Pro Val Met Ile Ile Thr Glu Phe Met Glu Asn
    675                 680                 685

GGC TCC CTG GAC TCC TTT CTC CGG CAA AAC GAT GGG CAG TTC ACA GTC       2112
Gly Ser Leu Asp Ser Phe Leu Arg Gln Asn Asp Gly Gln Phe Thr Val
690                 695                 700

ATC CAG CTG GTG GGC ATG CTT CGG GGC ATC GCA GCT GGC ATG AAG TAC       2160
Ile Gln Leu Val Gly Met Leu Arg Gly Ile Ala Ala Gly Met Lys Tyr
705                 710                 715                 720
```

```
CTG GCA GAC ATG AAC TAT GTT CAC CGT GAC CTG GCT GCC CGC AAC ATC        2208
Leu Ala Asp Met Asn Tyr Val His Arg Asp Leu Ala Ala Arg Asn Ile
                725                 730                 735

CTC GTC AAC AGC AAC CTG GTC TGC AAG GTG TCG GAC TTT GGG CTC TCA        2256
Leu Val Asn Ser Asn Leu Val Cys Lys Val Ser Asp Phe Gly Leu Ser
            740                 745                 750

CGC TTT CTA GAG GAC GAT ACC TCA GAC CCC ACC TAC ACC AGT GCC CTG        2304
Arg Phe Leu Glu Asp Asp Thr Ser Asp Pro Thr Tyr Thr Ser Ala Leu
            755                 760                 765

GGC GGA AAG TTC CCC ATC CGC TGG ACA GCC CCG GAA GCC ATC CAG TAC        2352
Gly Gly Lys Phe Pro Ile Arg Trp Thr Ala Pro Glu Ala Ile Gln Tyr
770                 775                 780

CGG AAG TTC ACC TCG GCC AGT GAT GTG TGG AGC TAC GGC ATT GTC ATG        2400
Arg Lys Phe Thr Ser Ala Ser Asp Val Trp Ser Tyr Gly Ile Val Met
785                 790                 795                 800

TGG GAG GTG ATG TCC TAT GGG GAG CGG CCC TAC TGG GAC ATG ACC AAC        2448
Trp Glu Val Met Ser Tyr Gly Glu Arg Pro Tyr Trp Asp Met Thr Asn
                805                 810                 815

CAG GAT GTA ATC AAT GCC ATT GAG CAG GAC TAT CGG CTG CCA CCG CCC        2496
Gln Asp Val Ile Asn Ala Ile Glu Gln Asp Tyr Arg Leu Pro Pro Pro
            820                 825                 830

ATG GAC TGC CCG AGC GCC CTG CAC CAA CTC ATG CTG GAC TGT TGG CAG        2544
Met Asp Cys Pro Ser Ala Leu His Gln Leu Met Leu Asp Cys Trp Gln
            835                 840                 845

AAG GAC CGC AAC CAC CGG CCC AAG TTC GGC CAA ATT GTC AAC ACG CTA        2592
Lys Asp Arg Asn His Arg Pro Lys Phe Gly Gln Ile Val Asn Thr Leu
            850                 855                 860

GAC AAG ATG ATC CGC AAT CCC AAC AGC CTC AAA GCC ATG GCG CCC CTC        2640
Asp Lys Met Ile Arg Asn Pro Asn Ser Leu Lys Ala Met Ala Pro Leu
865                 870                 875                 880

TCC TCT GGC ATC AAC CTG CCG CTG CTG GAC CGC ACG ATC CCC GAC TAC        2688
Ser Ser Gly Ile Asn Leu Pro Leu Leu Asp Arg Thr Ile Pro Asp Tyr
                885                 890                 895

ACC AGC TTT AAC ACG GTG GAC GAG TGG CTG GAG GCC ATC AAG ATG GGG        2736
Thr Ser Phe Asn Thr Val Asp Glu Trp Leu Glu Ala Ile Lys Met Gly
            900                 905                 910

CAG TAC AAG GAG AGC TTC GCC AAT GCC GGC TTC ACC TCC TTT GAC GTC        2784
Gln Tyr Lys Glu Ser Phe Ala Asn Ala Gly Phe Thr Ser Phe Asp Val
            915                 920                 925

GTG TCT CAG ATG ATG ATG GAG GAC ATT CTC CGG GTT GGG GTC ACT TTG        2832
Val Ser Gln Met Met Met Glu Asp Ile Leu Arg Val Gly Val Thr Leu
930                 935                 940

GCT GGC CAC CAG AAA AAA ATC CTG AAC AGT ATC CAG GTG ATG CGG GCG        2880
Ala Gly His Gln Lys Lys Ile Leu Asn Ser Ile Gln Val Met Arg Ala
945                 950                 955                 960

CAG ATG AAC CAG ATT CAG TCT GTG GAG GTT TGA CATTCACCTG CCTCGGCTCA     2933
Gln Met Asn Gln Ile Gln Ser Val Glu Val  *
                965                 970

CCTCTTCCTC CAAGCCCCGC CCCCTCTGC                                        2962

(2) INFORMATION FOR SEQ ID NO:11:

(i) SEQUENCE CHARACTERISTICS:
        (A) LENGTH:  970 amino acids
        (B) TYPE: amino acid
        (D) TOPOLOGY: linear (ii) MOLECULE TYPE: protein (xi) SEQUENCE DESCRIPTION: SEQ ID NO:11:
```

```
Leu Leu Ala Ala Val Glu Glu Thr Leu Met Asp Ser Thr Thr Ala Thr
  1               5                  10                  15

Ala Glu Leu Gly Trp Met Val His Pro Pro Ser Gly Trp Glu Val
         20                  25                  30

Ser Gly Tyr Asp Glu Asn Met Asn Thr Ile Arg Thr Tyr Gln Val Cys
             35                  40                  45

Asn Val Phe Glu Ser Ser Gln Asn Asn Trp Leu Arg Thr Lys Phe Ile
     50                  55                  60

Arg Arg Arg Gly Ala His Arg Ile His Val Glu Met Lys Phe Ser Val
 65                  70                  75                  80

Arg Asp Cys Ser Ser Ile Pro Ser Val Pro Gly Ser Cys Lys Glu Thr
                 85                  90                  95

Phe Asn Leu Tyr Tyr Tyr Glu Ala Asp Phe Asp Ser Ala Thr Lys Thr
             100                 105                 110

Phe Pro Asn Trp Met Glu Asn Pro Trp Val Lys Val Asp Thr Ile Ala
             115                 120                 125

Ala Asp Glu Ser Phe Ser Gln Val Asp Leu Gly Gly Arg Val Met Lys
         130                 135                 140

Ile Asn Thr Glu Val Arg Ser Phe Gly Pro Val Ser Arg Ser Gly Phe
145                 150                 155                 160

Tyr Leu Ala Phe Gln Asp Tyr Gly Gly Cys Met Ser Leu Ile Ala Val
                 165                 170                 175

Arg Val Phe Tyr Arg Lys Cys Pro Arg Ile Ile Gln Asn Gly Ala Ile
             180                 185                 190

Phe Gln Glu Thr Leu Ser Gly Ala Glu Ser Thr Ser Leu Val Ala Ala
         195                 200                 205

Arg Gly Ser Cys Ile Ala Asn Ala Glu Glu Val Asp Val Pro Ile Lys
210                 215                 220

Leu Tyr Cys Asn Gly Asp Gly Glu Trp Leu Val Pro Ile Gly Arg Cys
225                 230                 235                 240

Met Cys Lys Ala Gly Phe Glu Ala Val Glu Asn Gly Thr Val Cys Arg
                 245                 250                 255

Gly Cys Pro Ser Gly Thr Phe Lys Ala Asn Gln Gly Asp Glu Ala Cys
             260                 265                 270

Thr His Cys Pro Ile Asn Ser Arg Thr Thr Ser Glu Gly Ala Thr Asn
         275                 280                 285

Cys Val Cys Arg Asn Gly Tyr Tyr Arg Ala Asp Leu Asp Pro Leu Asp
290                 295                 300

Met Pro Cys Thr Thr Ile Pro Ser Ala Pro Gln Ala Val Ile Ser Ser
305                 310                 315                 320

Val Asn Glu Thr Ser Leu Met Leu Glu Trp Thr Pro Pro Arg Asp Ser
             325                 330                 335

Gly Gly Arg Glu Asp Leu Val Tyr Asn Ile Ile Cys Lys Ser Cys Gly
         340                 345                 350

Ser Gly Arg Gly Ala Cys Thr Arg Cys Gly Asp Asn Val Gln Tyr Ala
         355                 360                 365

Pro Arg Gln Leu Gly Leu Thr Glu Pro Arg Ile Tyr Ile Ser Asp Leu
         370                 375                 380

Leu Ala His Thr Gln Tyr Thr Phe Glu Ile Gln Ala Val Asn Gly Val
385                 390                 395                 400

Thr Asp Gln Ser Pro Phe Ser Pro Gln Phe Ala Ser Val Asn Ile Thr
                 405                 410                 415

Thr Asn Gln Ala Ala Pro Ser Ala Val Ser Ile Met His Gln Val Ser
```

-continued

```
            420                 425                 430
Arg Thr Val Asp Ser Ile Thr Leu Ser Trp Ser Gln Pro Asp Gln Pro
            435                 440                 445
Asn Gly Val Ile Leu Asp Tyr Glu Leu Gln Tyr Tyr Glu Lys Glu Leu
            450                 455                 460
Ser Glu Tyr Asn Ala Thr Ala Ile Lys Ser Pro Thr Asn Thr Val Thr
465                 470                 475                 480
Gly Leu Lys Ala Gly Ala Ile Tyr Val Phe Gln Val Arg Ala Arg Thr
                    485                 490                 495
Val Ala Gly Tyr Gly Arg Tyr Ser Gly Lys Met Tyr Phe Gln Thr Met
                500                 505                 510
Thr Glu Ala Glu Tyr Gln Thr Ser Ile Gln Glu Lys Leu Pro Leu Ile
            515                 520                 525
Ile Gly Ser Ser Ala Ala Gly Leu Val Phe Leu Ile Ala Val Val Val
        530                 535                 540
Ile Ala Ile Val Cys Asn Arg Arg Gly Phe Glu Arg Ala Asp Ser Glu
545                 550                 555                 560
Tyr Thr Asp Lys Leu Gln His Tyr Thr Ser Gly His Ile Thr Pro Gly
                565                 570                 575
Met Lys Ile Tyr Ile Asp Pro Phe Thr Tyr Glu Asp Pro Asn Glu Ala
                580                 585                 590
Val Arg Glu Phe Ala Lys Glu Ile Asp Ile Ser Cys Val Lys Ile Glu
            595                 600                 605
Gln Val Ile Gly Ala Gly Glu Phe Gly Glu Val Cys Ser Gly His Leu
        610                 615                 620
Lys Leu Pro Gly Lys Arg Glu Ile Phe Val Ala Ile Lys Thr Leu Lys
625                 630                 635                 640
Ser Gly Tyr Thr Glu Lys Gln Arg Arg Asp Phe Leu Ser Glu Ala Ser
                645                 650                 655
Ile Met Gly Gln Phe Asp His Pro Asn Val Ile His Leu Glu Gly Val
                660                 665                 670
Val Thr Lys Ser Thr Pro Val Met Ile Ile Thr Glu Phe Met Glu Asn
            675                 680                 685
Gly Ser Leu Asp Ser Phe Leu Arg Gln Asn Asp Gly Gln Phe Thr Val
        690                 695                 700
Ile Gln Leu Val Gly Met Leu Arg Gly Ile Ala Ala Gly Met Lys Tyr
705                 710                 715                 720
Leu Ala Asp Met Asn Tyr Val His Arg Asp Leu Ala Ala Arg Asn Ile
                725                 730                 735
Leu Val Asn Ser Asn Leu Val Cys Lys Val Ser Asp Phe Gly Leu Ser
            740                 745                 750
Arg Phe Leu Glu Asp Asp Thr Ser Asp Pro Thr Tyr Thr Ser Ala Leu
        755                 760                 765
Gly Gly Lys Phe Pro Ile Arg Trp Thr Ala Pro Glu Ala Ile Gln Tyr
        770                 775                 780
Arg Lys Phe Thr Ser Ala Ser Asp Val Trp Ser Tyr Gly Ile Val Met
785                 790                 795                 800
Trp Glu Val Met Ser Tyr Gly Glu Arg Pro Tyr Trp Asp Met Thr Asn
                805                 810                 815
Gln Asp Val Ile Asn Ala Ile Glu Gln Asp Tyr Arg Leu Pro Pro Pro
            820                 825                 830
Met Asp Cys Pro Ser Ala Leu His Gln Leu Met Leu Asp Cys Trp Gln
        835                 840                 845
```

```
Lys Asp Arg Asn His Arg Pro Lys Phe Gly Gln Ile Val Asn Thr Leu
    850                 855                 860

Asp Lys Met Ile Arg Asn Pro Asn Ser Leu Lys Ala Met Ala Pro Leu
865                 870                 875                 880

Ser Ser Gly Ile Asn Leu Pro Leu Leu Asp Arg Thr Ile Pro Asp Tyr
                885                 890                 895

Thr Ser Phe Asn Thr Val Asp Glu Trp Leu Glu Ala Ile Lys Met Gly
            900                 905                 910

Gln Tyr Lys Glu Ser Phe Ala Asn Ala Gly Phe Thr Ser Phe Asp Val
        915                 920                 925

Val Ser Gln Met Met Met Glu Asp Ile Leu Arg Val Gly Val Thr Leu
    930                 935                 940

Ala Gly His Gln Lys Lys Ile Leu Asn Ser Ile Gln Val Met Arg Ala
945                 950                 955                 960

Gln Met Asn Gln Ile Gln Ser Val Glu Val
                965                 970
```

(2) INFORMATION FOR SEQ ID NO:12:

(i) SEQUENCE CHARACTERISTICS:
        (A) LENGTH: 3162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2976

(xi) SEQUENCE DESCRIPTION: SEQ ID NO:12:

```
CCA GCG TCC CTG GCC GGC TGC TAC TCT GCA CCT CGA CGG GCT CCC CTC     48
Pro Ala Ser Leu Ala Gly Cys Tyr Ser Ala Pro Arg Arg Ala Pro Leu
 1               5                  10                  15

TGG ACG TGC CTT CTC CTG TGC GCC GCA CTC CGG ACC CTC CTG GCC AGC     96
Trp Thr Cys Leu Leu Leu Cys Ala Ala Leu Arg Thr Leu Leu Ala Ser
             20                  25                  30

CCC AGC AAC GAA GTG AAT TTA TTG GAT TCA CGC ACT GTC ATG GGG GAC    144
Pro Ser Asn Glu Val Asn Leu Leu Asp Ser Arg Thr Val Met Gly Asp
         35                  40                  45

CTG GGA TGG ATT GCT TTT CCA AAA AAT GGG TGG GAA GAG ATT GGT GAA    192
Leu Gly Trp Ile Ala Phe Pro Lys Asn Gly Trp Glu Glu Ile Gly Glu
     50                  55                  60

GTG GAT GAA AAT TAT GCC CCT ATC CAC ACA TAC CAA GTA TGC AAA GTG    240
Val Asp Glu Asn Tyr Ala Pro Ile His Thr Tyr Gln Val Cys Lys Val
 65                  70                  75                  80

ATG GAA CAG AAT CAG AAT AAC TGG CTT TTG ACC AGT TGG ATC TCC AAT    288
Met Glu Gln Asn Gln Asn Asn Trp Leu Leu Thr Ser Trp Ile Ser Asn
             85                  90                  95

GAA GGT GCT TCC AGA ATC TTC ATA GAA CTC AAA TTT ACC CTG CGG GAC    336
Glu Gly Ala Ser Arg Ile Phe Ile Glu Leu Lys Phe Thr Leu Arg Asp
            100                 105                 110

TGC AAC AGC CTT CCT GGA GGA CTG GGG ACC TGT AAG GAA ACC TTT AAT    384
Cys Asn Ser Leu Pro Gly Gly Leu Gly Thr Cys Lys Glu Thr Phe Asn
        115                 120                 125

ATG TAT TAC TTT GAG TCA GAT GAT CAG AAT GGG AGA AAC ATC AAG GAA    432
Met Tyr Tyr Phe Glu Ser Asp Asp Gln Asn Gly Arg Asn Ile Lys Glu
    130                 135                 140

AAC CAA TAC ATC AAA ATT GAT ACC ATT GCT GCC GAT GAA AGC TTT ACA    480
```

```
                                                           -continued

Asn Gln Tyr Ile Lys Ile Asp Thr Ile Ala Ala Asp Glu Ser Phe Thr
145                 150                 155                 160

GAA CTT GAT CTT GGT GAC CGT GTT ATG AAA CTG AAT ACA GAG GTC AGA      528
Glu Leu Asp Leu Gly Asp Arg Val Met Lys Leu Asn Thr Glu Val Arg
                    165                 170                 175

GAT GTA GGA CCT CTA AGC AAA AAG GGA TTT TAT CTT GCT TTT CAA GAT      576
Asp Val Gly Pro Leu Ser Lys Lys Gly Phe Tyr Leu Ala Phe Gln Asp
                180                 185                 190

GTT GGT GCT TGC ATT GCT CTG GTT TCT GTG CGT GTA TAC TAT AAA AAA      624
Val Gly Ala Cys Ile Ala Leu Val Ser Val Arg Val Tyr Tyr Lys Lys
            195                 200                 205

TGC CCT TCT GTG GTA CGA CAC TTG GCT GTC TTC CCT GAC ACC ATC ACT      672
Cys Pro Ser Val Val Arg His Leu Ala Val Phe Pro Asp Thr Ile Thr
210                 215                 220

GGA GCT GAT TCT TCC CAA TTG CTC GAA GTG TCG GGC TCC TGT GTC AAC      720
Gly Ala Asp Ser Ser Gln Leu Leu Glu Val Ser Gly Ser Cys Val Asn
225                 230                 235                 240

CAT TCT GTG ACC GAT GAA CCT CCC AAA ATG CAC TGC AGC GCC GAA GGG      768
His Ser Val Thr Asp Glu Pro Pro Lys Met His Cys Ser Ala Glu Gly
                245                 250                 255

GAG TGG CTG GTG CCC ATC GGG AAA TGC ATG TGC AAG GCA GGA TAT GAA      816
Glu Trp Leu Val Pro Ile Gly Lys Cys Met Cys Lys Ala Gly Tyr Glu
                260                 265                 270

GAG AAA AAT GGC ACC TGT CAA GTG TGC AGA CCT GGG TTC TTC AAA GCC      864
Glu Lys Asn Gly Thr Cys Gln Val Cys Arg Pro Gly Phe Phe Lys Ala
            275                 280                 285

TCA CCT CAC ATC CAG AGC TGC GGC AAA TGT CCA CCT CAC AGT TAT ACC      912
Ser Pro His Ile Gln Ser Cys Gly Lys Cys Pro Pro His Ser Tyr Thr
290                 295                 300

CAT GAG GAA GCT TCA ACC TCT TGT GTC TGT GAA AAG GAT TAT TTC AGG      960
His Glu Glu Ala Ser Thr Ser Cys Val Cys Glu Lys Asp Tyr Phe Arg
305                 310                 315                 320

AGA GAG TCT GAT CCA CCC ACA ATG GCA TGC ACA AGA CCC CCC TCT GCT     1008
Arg Glu Ser Asp Pro Pro Thr Met Ala Cys Thr Arg Pro Pro Ser Ala
                325                 330                 335

CCT CGG AAT GCC ATC TCA AAT GTT AAT GAA ACT AGT GTC TTT CTG GAA     1056
Pro Arg Asn Ala Ile Ser Asn Val Asn Glu Thr Ser Val Phe Leu Glu
                340                 345                 350

TGG ATT CCG CCT GCT GAC ACT GGT GGA AGG AAA GAC GTG TCA TAT TAT     1104
Trp Ile Pro Pro Ala Asp Thr Gly Gly Arg Lys Asp Val Ser Tyr Tyr
            355                 360                 365

ATT GCA TGC AAG AAG TGC AAC TCC CAT GCA GGT GTG TGT GAG GAG TGT     1152
Ile Ala Cys Lys Lys Cys Asn Ser His Ala Gly Val Cys Glu Glu Cys
370                 375                 380

GGC GGT CAT GTC AGG TAC CTT CCC CGG CAA AGC GGC CTG AAA AAC ACC     1200
Gly Gly His Val Arg Tyr Leu Pro Arg Gln Ser Gly Leu Lys Asn Thr
385                 390                 395                 400

TCT GTC ATG ATG GTG GAT CTA CTC GCT CAC ACA AAC TAT ACC TTT GAG     1248
Ser Val Met Met Val Asp Leu Leu Ala His Thr Asn Tyr Thr Phe Glu
                405                 410                 415

ATT GAG GCA GTG AAT GGA GTG TCC GAC TTG AGC CCA GGA GCC CGG CAG     1296
Ile Glu Ala Val Asn Gly Val Ser Asp Leu Ser Pro Gly Ala Arg Gln
                420                 425                 430

TAT GTG TCT GTA AAT GTA ACC ACA AAT CAA GCA GCT CCA TCT CCA GTC     1344
Tyr Val Ser Val Asn Val Thr Thr Asn Gln Ala Ala Pro Ser Pro Val
            435                 440                 445

ACC AAT GTG AAA AAA GGG AAA ATT GCA AAA AAC AGC ATC TCT TTG TCT     1392
Thr Asn Val Lys Lys Gly Lys Ile Ala Lys Asn Ser Ile Ser Leu Ser
450                 455                 460
```

```
                                                                        -continued TGG CAA GAA CCA GAT CGT CCC AAT GGA ATC ATC CTA GAG TAT GAA ATC         1440
Trp Gln Glu Pro Asp Arg Pro Asn Gly Ile Ile Leu Glu Tyr Glu Ile
465                 470                 475                 480

AAG CAT TTT GAA AAG GAC CAA GAG ACC AGC TAC ACG ATT ATC AAA TCT         1488
Lys His Phe Glu Lys Asp Gln Glu Thr Ser Tyr Thr Ile Ile Lys Ser
                    485                 490                 495

AAA GAG ACA ACT ATT ACT GCA GAG GGC TTG AAA CCA GCT TCA GTT TAT         1536
Lys Glu Thr Thr Ile Thr Ala Glu Gly Leu Lys Pro Ala Ser Val Tyr
                500                 505                 510

GTC TTC CAA ATT CGA GCA CGT ACA GCA GCA GGC TAT GGT GTC TTC AGT         1584
Val Phe Gln Ile Arg Ala Arg Thr Ala Ala Gly Tyr Gly Val Phe Ser
            515                 520                 525

CGA AGA TTT GAG TTT GAA ACC ACC CCA GTG TTT GCA GCA TCC AGC GAT         1632
Arg Arg Phe Glu Phe Glu Thr Thr Pro Val Phe Ala Ala Ser Ser Asp
530                 535                 540

CAA AGC CAG ATT CCT GTA ATT GCT GTG TCT GTG ACA GTA GGA GTC ATT         1680
Gln Ser Gln Ile Pro Val Ile Ala Val Ser Val Thr Val Gly Val Ile
545                 550                 555                 560

TTG TTG GCA GTG GTT ATC GGC GTC CTC CTC AGT GGA AGG CGG TGT GGC         1728
Leu Leu Ala Val Val Ile Gly Val Leu Leu Ser Gly Arg Arg Cys Gly
                    565                 570                 575

TAC AGC AAA GCA AAA CAA GAT CCA GAA GAG GAA AAG ATG CAT TTT CAT         1776
Tyr Ser Lys Ala Lys Gln Asp Pro Glu Glu Glu Lys Met His Phe His
                580                 585                 590

AAT GGG CAC ATT AAA CTG CCA GGA GTA AGA ACT TAC ATT GAT CCA CAT         1824
Asn Gly His Ile Lys Leu Pro Gly Val Arg Thr Tyr Ile Asp Pro His
            595                 600                 605

ACC TAT GAG GAT CCC AAT CAA GCT GTC CAC GAA TTT GCC AAG GAG ATA         1872
Thr Tyr Glu Asp Pro Asn Gln Ala Val His Glu Phe Ala Lys Glu Ile
610                 615                 620

GAA GCA TCA TGT ATC ACC ATT GAG AGA GTT ATT GGA GCA GGT GAA TTT         1920
Glu Ala Ser Cys Ile Thr Ile Glu Arg Val Ile Gly Ala Gly Glu Phe
625                 630                 635                 640

GGT GAA GTT TGT AGT GGA CGT TTG AAA CTA CCA GGA AAA AGA GAA TTA         1968
Gly Glu Val Cys Ser Gly Arg Leu Lys Leu Pro Gly Lys Arg Glu Leu
                    645                 650                 655

CCT GTG GCT ATC AAA ACC CTT AAA GTA GGC TAT ACT GAA AAG CAA CGC         2016
Pro Val Ala Ile Lys Thr Leu Lys Val Gly Tyr Thr Glu Lys Gln Arg
                660                 665                 670

AGA GAT TTC CTA GGT GAA GCA AGT ATC ATG GGA CAG TTT GAT CAT CCT         2064
Arg Asp Phe Leu Gly Glu Ala Ser Ile Met Gly Gln Phe Asp His Pro
            675                 680                 685

AAC ATC ATC CAT TTA GAA GGT GTG GTG ACC AAA AGT AAA CCA GTG ATG         2112
Asn Ile Ile His Leu Glu Gly Val Val Thr Lys Ser Lys Pro Val Met
690                 695                 700

ATC GTG ACA GAG TAT ATG GAG AAT GGC TCT TTA GAT ACA TTT TTG AAG         2160
Ile Val Thr Glu Tyr Met Glu Asn Gly Ser Leu Asp Thr Phe Leu Lys
705                 710                 715                 720

AAA AAC GAT GGG CAG TTC ACT GTG ATT CAG CTT GTT GGC ATG CTG AGA         2208
Lys Asn Asp Gly Gln Phe Thr Val Ile Gln Leu Val Gly Met Leu Arg
                    725                 730                 735

GGT ATC TCT GCA GGA ATG AAG TAC CTT TCT GAC ATG GGC TAT GTG CAT         2256
Gly Ile Ser Ala Gly Met Lys Tyr Leu Ser Asp Met Gly Tyr Val His
                740                 745                 750

AGA GAT CTT GCT GCC AGA AAC ATC TTA ATC AAC AGT AAC CTT GTG TGC         2304
Arg Asp Leu Ala Ala Arg Asn Ile Leu Ile Asn Ser Asn Leu Val Cys
            755                 760                 765

AAA GTG TCT GAC TTT GGA CTT TCC CGG GTA CTG GAA GAT GAT CCC GAG         2352
Lys Val Ser Asp Phe Gly Leu Ser Arg Val Leu Glu Asp Asp Pro Glu
770                 775                 780
```

```
GCA GCC TAC ACC ACA AGG GGA GGA AAA ATT CCA ATC AGA TGG ACT GCC    2400
Ala Ala Tyr Thr Thr Arg Gly Gly Lys Ile Pro Ile Arg Trp Thr Ala
785             790                 795                 800

CCA GAA GCA ATA GCT TTC CGA AAG TTT ACT TCT GCC AGT GAT GTC TGG    2448
Pro Glu Ala Ile Ala Phe Arg Lys Phe Thr Ser Ala Ser Asp Val Trp
                805                 810                 815

AGT TAT GGA ATA GTA ATG TGG GAA GTT GTG TCT TAT GGA GAG AGA CCC    2496
Ser Tyr Gly Ile Val Met Trp Glu Val Val Ser Tyr Gly Glu Arg Pro
            820                 825                 830

TAC TGG GAG ATG ACC AAT CAA GAT GTG ATT AAA GCG GTA GAG GAA GGC    2544
Tyr Trp Glu Met Thr Asn Gln Asp Val Ile Lys Ala Val Glu Glu Gly
                835                 840                 845

TAT CGT CTG CCA AGC CCC ATG GAT TGT CCT GCT GCT CTC TAT CAG TTA    2592
Tyr Arg Leu Pro Ser Pro Met Asp Cys Pro Ala Ala Leu Tyr Gln Leu
850             855                 860

ATG CTG GAT TGC TGG CAG AAA GAG CGA AAT AGC AGG CCC AAG TTT GAT    2640
Met Leu Asp Cys Trp Gln Lys Glu Arg Asn Ser Arg Pro Lys Phe Asp
865             870                 875                 880

GAA ATA GTC AAC ATG TTG GAC AAG CTG ATA CGT AAC CCA AGT AGT CTG    2688
Glu Ile Val Asn Met Leu Asp Lys Leu Ile Arg Asn Pro Ser Ser Leu
                885                 890                 895

AAG ACG CTG GTT AAT GCA TCC TGC AGA GTA TCT AAT TTA TTG GCA GAA    2736
Lys Thr Leu Val Asn Ala Ser Cys Arg Val Ser Asn Leu Leu Ala Glu
            900                 905                 910

CAT AGC CCA CTA GGA TCT GGG GCC TAC AGA TCA GTA GGT GAA TGG CTA    2784
His Ser Pro Leu Gly Ser Gly Ala Tyr Arg Ser Val Gly Glu Trp Leu
                915                 920                 925

GAG GCA ATC AAG ATG GGC CGG TAT ACA GAG ATT TTC ATG GAA AAT GGA    2832
Glu Ala Ile Lys Met Gly Arg Tyr Thr Glu Ile Phe Met Glu Asn Gly
            930                 935                 940

TAC AGT TCA ATG GAC GCT GTG GCT CAG GTG ACC TTG GAG GAT TTG AGA    2880
Tyr Ser Ser Met Asp Ala Val Ala Gln Val Thr Leu Glu Asp Leu Arg
945             950                 955                 960

CGG CTT GGA GTG ACT CTT GTC GGT CAC CAG AAG AAG ATC ATG AAC AGC    2928
Arg Leu Gly Val Thr Leu Val Gly His Gln Lys Lys Ile Met Asn Ser
                965                 970                 975

CTT CAA GAA ATG AAG GTG CAG CTG GTA AAC GGA ATG GTG CCA TTG TAA    2976
Leu Gln Glu Met Lys Val Gln Leu Val Asn Gly Met Val Pro Leu  *
            980                 985                 990

CTTCATGTAA ATGTCGCTTC TTCAAGTGAA TGATTCTGCA CTTTGTAAAC AGCACTGAGA   3036

TTTATTTTAA CAAAAAAAGG GGGAAAAGGG AAAACAGTGA TTTCTAAACC TTAGAAAACA   3096

TTTGCCTCAG CCACAGAATT TGTAATCATG GTTTTACTGA AGTATCCAGT TCTTAGTCCT   3156

TAGTCT                                                              3162

(2) INFORMATION FOR SEQ ID NO:13:

(i) SEQUENCE CHARACTERISTICS:
        (A) LENGTH: 991 amino acids
        (B) TYPE: amino acid
        (D) TOPOLOGY: linear (ii) MOLECULE TYPE: protein (xi) SEQUENCE DESCRIPTION: SEQ ID NO:13:

Pro Ala Ser Leu Ala Gly Cys Tyr Ser Ala Pro Arg Arg Ala Pro Leu
 1               5                  10                  15

Trp Thr Cys Leu Leu Leu Cys Ala Ala Leu Arg Thr Leu Leu Ala Ser
            20                  25                  30
```

```
Pro Ser Asn Glu Val Asn Leu Leu Asp Ser Arg Thr Val Met Gly Asp
         35                  40                  45

Leu Gly Trp Ile Ala Phe Pro Lys Asn Gly Trp Glu Ile Gly Glu
     50                  55                  60

Val Asp Glu Asn Tyr Ala Pro Ile His Thr Tyr Gln Val Cys Lys Val
 65                  70                  75                  80

Met Glu Gln Asn Gln Asn Asn Trp Leu Leu Thr Ser Trp Ile Ser Asn
                 85                  90                  95

Glu Gly Ala Ser Arg Ile Phe Ile Glu Leu Lys Phe Thr Leu Arg Asp
             100                 105                 110

Cys Asn Ser Leu Pro Gly Gly Leu Gly Thr Cys Lys Glu Thr Phe Asn
         115                 120                 125

Met Tyr Tyr Phe Glu Ser Asp Asp Gln Asn Gly Arg Asn Ile Lys Glu
     130                 135                 140

Asn Gln Tyr Ile Lys Ile Asp Thr Ile Ala Ala Asp Glu Ser Phe Thr
145                 150                 155                 160

Glu Leu Asp Leu Gly Asp Arg Val Met Lys Leu Asn Thr Glu Val Arg
                 165                 170                 175

Asp Val Gly Pro Leu Ser Lys Lys Gly Phe Tyr Leu Ala Phe Gln Asp
             180                 185                 190

Val Gly Ala Cys Ile Ala Leu Val Ser Val Arg Val Tyr Tyr Lys Lys
         195                 200                 205

Cys Pro Ser Val Val Arg His Leu Ala Val Phe Pro Asp Thr Ile Thr
     210                 215                 220

Gly Ala Asp Ser Ser Gln Leu Leu Glu Val Ser Gly Ser Cys Val Asn
225                 230                 235                 240

His Ser Val Thr Asp Glu Pro Pro Lys Met His Cys Ser Ala Glu Gly
                 245                 250                 255

Glu Trp Leu Val Pro Ile Gly Lys Cys Met Cys Lys Ala Gly Tyr Glu
             260                 265                 270

Glu Lys Asn Gly Thr Cys Gln Val Cys Arg Pro Gly Phe Phe Lys Ala
         275                 280                 285

Ser Pro His Ile Gln Ser Cys Gly Lys Cys Pro Pro His Ser Tyr Thr
     290                 295                 300

His Glu Glu Ala Ser Thr Ser Cys Val Cys Glu Lys Asp Tyr Phe Arg
305                 310                 315                 320

Arg Glu Ser Asp Pro Pro Thr Met Ala Cys Thr Arg Pro Pro Ser Ala
                 325                 330                 335

Pro Arg Asn Ala Ile Ser Asn Val Asn Glu Thr Ser Val Phe Leu Glu
             340                 345                 350

Trp Ile Pro Pro Ala Asp Thr Gly Gly Arg Lys Asp Val Ser Tyr Tyr
         355                 360                 365

Ile Ala Cys Lys Lys Cys Asn Ser His Ala Gly Val Cys Glu Glu Cys
     370                 375                 380

Gly Gly His Val Arg Tyr Leu Pro Arg Gln Ser Gly Leu Lys Asn Thr
385                 390                 395                 400

Ser Val Met Met Val Asp Leu Leu Ala His Thr Asn Tyr Thr Phe Glu
                 405                 410                 415

Ile Glu Ala Val Asn Gly Val Ser Asp Leu Ser Pro Gly Ala Arg Gln
             420                 425                 430

Tyr Val Ser Val Asn Val Thr Thr Asn Gln Ala Ala Pro Ser Pro Val
         435                 440                 445

Thr Asn Val Lys Lys Gly Lys Ile Ala Lys Asn Ser Ile Ser Leu Ser
```

```
                450                 455                 460
Trp Gln Glu Pro Asp Arg Pro Asn Gly Ile Ile Leu Glu Tyr Glu Ile
465                 470                 475                 480

Lys His Phe Glu Lys Asp Gln Glu Thr Ser Tyr Thr Ile Ile Lys Ser
                485                 490                 495

Lys Glu Thr Thr Ile Thr Ala Glu Gly Leu Lys Pro Ala Ser Val Tyr
                500                 505                 510

Val Phe Gln Ile Arg Ala Arg Thr Ala Ala Gly Tyr Gly Val Phe Ser
                515                 520                 525

Arg Arg Phe Glu Phe Glu Thr Thr Pro Val Phe Ala Ala Ser Ser Asp
530                 535                 540

Gln Ser Gln Ile Pro Val Ile Ala Val Ser Val Thr Gly Val Ile
545                 550                 555                 560

Leu Leu Ala Val Val Ile Gly Val Leu Leu Ser Gly Arg Arg Cys Gly
                565                 570                 575

Tyr Ser Lys Ala Lys Gln Asp Pro Glu Glu Lys Met His Phe His
                580                 585                 590

Asn Gly His Ile Lys Leu Pro Gly Val Arg Thr Tyr Ile Asp Pro His
                595                 600                 605

Thr Tyr Glu Asp Pro Asn Gln Ala Val His Glu Phe Ala Lys Glu Ile
                610                 615                 620

Glu Ala Ser Cys Ile Thr Ile Glu Arg Val Ile Gly Ala Gly Glu Phe
625                 630                 635                 640

Gly Glu Val Cys Ser Gly Arg Leu Lys Leu Pro Gly Lys Arg Glu Leu
                645                 650                 655

Pro Val Ala Ile Lys Thr Leu Lys Val Gly Tyr Thr Glu Lys Gln Arg
                660                 665                 670

Arg Asp Phe Leu Gly Glu Ala Ser Ile Met Gly Gln Phe Asp His Pro
                675                 680                 685

Asn Ile Ile His Leu Glu Gly Val Val Thr Lys Ser Lys Pro Val Met
                690                 695                 700

Ile Val Thr Glu Tyr Met Glu Asn Gly Ser Leu Asp Thr Phe Leu Lys
705                 710                 715                 720

Lys Asn Asp Gly Gln Phe Thr Val Ile Gln Leu Val Gly Met Leu Arg
                725                 730                 735

Gly Ile Ser Ala Gly Met Lys Tyr Leu Ser Asp Met Gly Tyr Val His
                740                 745                 750

Arg Asp Leu Ala Ala Arg Asn Ile Leu Ile Asn Ser Asn Leu Val Cys
                755                 760                 765

Lys Val Ser Asp Phe Gly Leu Ser Arg Val Leu Glu Asp Asp Pro Glu
                770                 775                 780

Ala Ala Tyr Thr Thr Arg Gly Gly Lys Ile Pro Ile Arg Trp Thr Ala
785                 790                 795                 800

Pro Glu Ala Ile Ala Phe Arg Lys Phe Thr Ser Ala Ser Asp Val Trp
                805                 810                 815

Ser Tyr Gly Ile Val Met Trp Glu Val Val Ser Tyr Gly Glu Arg Pro
                820                 825                 830

Tyr Trp Glu Met Thr Asn Gln Asp Val Ile Lys Ala Val Glu Glu Gly
                835                 840                 845

Tyr Arg Leu Pro Ser Pro Met Asp Cys Pro Ala Ala Leu Tyr Gln Leu
                850                 855                 860

Met Leu Asp Cys Trp Gln Lys Glu Arg Asn Ser Arg Pro Lys Phe Asp
865                 870                 875                 880
```

-continued

```
Glu Ile Val Asn Met Leu Asp Lys Leu Ile Arg Asn Pro Ser Ser Leu
            885                 890                 895

Lys Thr Leu Val Asn Ala Ser Cys Arg Val Ser Asn Leu Leu Ala Glu
            900                 905                 910

His Ser Pro Leu Gly Ser Gly Ala Tyr Arg Ser Val Gly Glu Trp Leu
            915                 920                 925

Glu Ala Ile Lys Met Gly Arg Tyr Thr Glu Ile Phe Met Glu Asn Gly
            930                 935                 940

Tyr Ser Ser Met Asp Ala Val Ala Gln Val Thr Leu Glu Asp Leu Arg
945                 950                 955                 960

Arg Leu Gly Val Thr Leu Val Gly His Gln Lys Lys Ile Met Asn Ser
            965                 970                 975

Leu Gln Glu Met Lys Val Gln Leu Val Asn Gly Met Val Pro Leu
            980                 985                 990
```

(2) INFORMATION FOR SEQ ID NO:14:

(i) SEQUENCE CHARACTERISTICS:
        (A) LENGTH: 3116 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 34..2994

(xi) SEQUENCE DESCRIPTION: SEQ ID NO:14:

```
AAGCGGCAGG AGCAGCGTTG GCACCGGCGA ACC ATG GCT GGG ATT TTC TAT TTC      54
                                    Met Ala Gly Ile Phe Tyr Phe
                                      1               5

GCC CTA TTT TCG TGT CTC TTC GGG ATT TGC GAC GCT GTC ACA GGT TCC      102
Ala Leu Phe Ser Cys Leu Phe Gly Ile Cys Asp Ala Val Thr Gly Ser
            10                  15                  20

AGG GTA TAC CCC GCG AAT GAA GTT ACC TTA TTG GAT TCC AGA TCT GTT      150
Arg Val Tyr Pro Ala Asn Glu Val Thr Leu Leu Asp Ser Arg Ser Val
    25                  30                  35

CAG GGA GAA CTT GGG TGG ATA GCA AGC CCT CTG GAA GGA GGG TGG GAG      198
Gln Gly Glu Leu Gly Trp Ile Ala Ser Pro Leu Glu Gly Gly Trp Glu
40                  45                  50                  55

GAA GTG AGT ATC ATG GAT GAA AAA AAT ACA CCA ATC CGA ACC TAC CAA      246
Glu Val Ser Ile Met Asp Glu Lys Asn Thr Pro Ile Arg Thr Tyr Gln
                60                  65                  70

GTG TGC AAT GTG ATG GAA CCC AGC CAG AAT AAC TGG CTA CGA ACT GAT      294
Val Cys Asn Val Met Glu Pro Ser Gln Asn Asn Trp Leu Arg Thr Asp
            75                  80                  85

TGG ATC ACC CGA GAA GGG GCT CAG AGG GTG TAT ATT GAG ATT AAA TTC      342
Trp Ile Thr Arg Glu Gly Ala Gln Arg Val Tyr Ile Glu Ile Lys Phe
        90                  95                 100

ACC TTG AGG GAC TGC AAT AGT CTT CCG GGC GTC ATG GGG ACT TGC AAG      390
Thr Leu Arg Asp Cys Asn Ser Leu Pro Gly Val Met Gly Thr Cys Lys
    105                 110                 115

GAG ACG TTT AAC CTG TAC TAC TAT GAA TCA GAC AAC GAC AAA GAG CGT      438
Glu Thr Phe Asn Leu Tyr Tyr Tyr Glu Ser Asp Asn Asp Lys Glu Arg
120                 125                 130                 135

TTC ATC AGA GAG AAC CAG TTT GTC AAA ATT GAC ACC ATT GCT GCT GAT      486
Phe Ile Arg Glu Asn Gln Phe Val Lys Ile Asp Thr Ile Ala Ala Asp
                140                 145                 150
```

```
GAG AGC TTC ACC CAA GTG GAC ATT GGT GAC AGA ATC ATG AAG CTG AAC      534
Glu Ser Phe Thr Gln Val Asp Ile Gly Asp Arg Ile Met Lys Leu Asn
            155                 160                 165

ACC GAG ATC CGG GAT GTA GGG CCA TTA AGC AAA AAG GGG TTT TAC CTG      582
Thr Glu Ile Arg Asp Val Gly Pro Leu Ser Lys Lys Gly Phe Tyr Leu
        170                 175                 180

GCT TTT CAG GAT GTG GGG GCC TGC ATC GCC CTG GTA TCA GTC CGT GTG      630
Ala Phe Gln Asp Val Gly Ala Cys Ile Ala Leu Val Ser Val Arg Val
    185                 190                 195

TTC TAT AAA AAG TGT CCA CTC ACA GTC CGC AAT CTG GCC CAG TTT CCT      678
Phe Tyr Lys Lys Cys Pro Leu Thr Val Arg Asn Leu Ala Gln Phe Pro
200                 205                 210                 215

GAC ACC ATC ACA GGG GCT GAT ACG TCT TCC CTG GTG GAA GTT CGA GGC      726
Asp Thr Ile Thr Gly Ala Asp Thr Ser Ser Leu Val Glu Val Arg Gly
            220                 225                 230

TCC TGT GTC AAC AAC TCA GAA GAG AAA GAT GTG CCA AAA ATG TAC TGT      774
Ser Cys Val Asn Asn Ser Glu Glu Lys Asp Val Pro Lys Met Tyr Cys
        235                 240                 245

GGG GCA GAT GGT GAA TGG CTG GTA CCC ATT GGC AAC TGC CTA TGC AAC      822
Gly Ala Asp Gly Glu Trp Leu Val Pro Ile Gly Asn Cys Leu Cys Asn
    250                 255                 260

GCT GGG CAT GAG GAG CGG AGC GGA GAA TGC CAA GCT TGC AAA ATT GGA      870
Ala Gly His Glu Glu Arg Ser Gly Glu Cys Gln Ala Cys Lys Ile Gly
265                 270                 275

TAT TAC AAG GCT CTC TCC ACG GAT GCC ACC TGT GCC AAG TGC CCA CCC      918
Tyr Tyr Lys Ala Leu Ser Thr Asp Ala Thr Cys Ala Lys Cys Pro Pro
280                 285                 290                 295

CAC AGC TAC TCT GTC TGG GAA GGA GCC ACC TCG TGC ACC TGT GAC CGA      966
His Ser Tyr Ser Val Trp Glu Gly Ala Thr Ser Cys Thr Cys Asp Arg
            300                 305                 310

GGC TTT TTC AGA GCT GAC AAC GAT GCT GCC TCT ATG CCC TGC ACC CGT     1014
Gly Phe Phe Arg Ala Asp Asn Asp Ala Ala Ser Met Pro Cys Thr Arg
        315                 320                 325

CCA CCA TCT GCT CCC CTG AAC TTG ATT TCA AAT GTC AAC GAG ACA TCT     1062
Pro Pro Ser Ala Pro Leu Asn Leu Ile Ser Asn Val Asn Glu Thr Ser
    330                 335                 340

GTG AAC TTG GAA TGG AGT AGC CCT CAG AAT ACA GGT GGC CGC CAG GAC     1110
Val Asn Leu Glu Trp Ser Ser Pro Gln Asn Thr Gly Gly Arg Gln Asp
345                 350                 355

ATT TCC TAT AAT GTG GTA TGC AAG AAA TGT GGA GCT GGT GAC CCC AGC     1158
Ile Ser Tyr Asn Val Val Cys Lys Lys Cys Gly Ala Gly Asp Pro Ser
360                 365                 370                 375

AAG TGC CGA CCC TGT GGA AGT GGG GTC CAC TAC ACC CCA CAG CAG AAT     1206
Lys Cys Arg Pro Cys Gly Ser Gly Val His Tyr Thr Pro Gln Gln Asn
            380                 385                 390

GGC TTG AAG ACC ACC AAA GTC TCC ATC ACT GAC CTC CTA GCT CAT ACC     1254
Gly Leu Lys Thr Thr Lys Val Ser Ile Thr Asp Leu Leu Ala His Thr
        395                 400                 405

AAT TAC ACC TTT GAA ATC TGG GCT GTG AAT GGA GTG TCC AAA TAT AAC     1302
Asn Tyr Thr Phe Glu Ile Trp Ala Val Asn Gly Val Ser Lys Tyr Asn
    410                 415                 420

CCT AAC CCA GAC CAA TCA GTT TCT GTC ACT GTG ACC ACC AAC CAA GCA     1350
Pro Asn Pro Asp Gln Ser Val Ser Val Thr Val Thr Thr Asn Gln Ala
425                 430                 435

GCA CCA TCA TCC ATT GCT TTG GTC CAG GCT AAA GAA GTC ACA AGA TAC     1398
Ala Pro Ser Ser Ile Ala Leu Val Gln Ala Lys Glu Val Thr Arg Tyr
440                 445                 450                 455

AGT GTG GCA CTG GCT TGG CTG GAA CCA GAT CGG CCC AAT GGG TAA ATC     1446
Ser Val Ala Leu Ala Trp Leu Glu Pro Asp Arg Pro Asn Gly Val Ile
            460                 465                 470
```

-continued

| | | |
|---|---|---|
| CTG GAA TAT GAA GTC AAG TAT TAT GAG AAG GAT CAG AAT GAG CGA AGC<br>Leu Glu Tyr Glu Val Lys Tyr Tyr Glu Lys Asp Gln Asn Glu Arg Ser<br>                475                       480                 485 | 1494 |
| TAT CGT ATA GTT CGG ACA GCT GCC AGG AAC ACA GAT ATC AAA GGC CTG<br>Tyr Arg Ile Val Arg Thr Ala Ala Arg Asn Thr Asp Ile Lys Gly Leu<br>         490                      495                    500 | 1542 |
| AAC CCT CTC ACT TCC TAT GTT TTC CAC GTG CGA GCC AGG ACA GCA GCT<br>Asn Pro Leu Thr Ser Tyr Val Phe His Val Arg Ala Arg Thr Ala Ala<br>505                      510                     515 | 1590 |
| GGC TAT GGA GAC TTC AGT GAG CCC TTG GAG GTT ACA ACC AAC ACA GTG<br>Gly Tyr Gly Asp Phe Ser Glu Pro Leu Glu Val Thr Thr Asn Thr Val<br>520                 525                    530                 535 | 1638 |
| CCT TCC CGG ATC ATT GGA GAT GGG GCT AAC TCC ACA GTC CTT CTG GTC<br>Pro Ser Arg Ile Ile Gly Asp Gly Ala Asn Ser Thr Val Leu Leu Val<br>                540                     545                 550 | 1686 |
| TCT GTC TCG GGC AGT GTG GTG CTG GTG GTA ATT CTC ATT GCA GCT TTT<br>Ser Val Ser Gly Ser Val Val Leu Val Val Ile Leu Ile Ala Ala Phe<br>                  555                     560                 565 | 1734 |
| GTC ATC AGC CGG AGA CGG AGT AAA TAC AGT AAA GCC AAA CAA GAA GCG<br>Val Ile Ser Arg Arg Arg Ser Lys Tyr Ser Lys Ala Lys Gln Glu Ala<br>              570                     575                 580 | 1782 |
| GAT GAA GAG AAA CAT TTG AAT CAA GGT GTA AGA ACA TAT GTG GAC CCC<br>Asp Glu Glu Lys His Leu Asn Gln Gly Val Arg Thr Tyr Val Asp Pro<br>585                      590                     595 | 1830 |
| TTT ACG TAC GAA GAT CCC AAC CAA GCA GTG CGA GAG TTT GCC AAA GAA<br>Phe Thr Tyr Glu Asp Pro Asn Gln Ala Val Arg Glu Phe Ala Lys Glu<br>600                      605                     610                 615 | 1878 |
| ATT GAC GCA TCC TGC ATT AAG ATT GAA AAA GTT ATA GGA GTT GGT GAA<br>Ile Asp Ala Ser Cys Ile Lys Ile Glu Lys Val Ile Gly Val Gly Glu<br>                  620                     625                 630 | 1926 |
| TTT GGT GAG GTA TGC AGT GGG CGT CTC AAA GTG CCT GGC AAG AGA GAG<br>Phe Gly Glu Val Cys Ser Gly Arg Leu Lys Val Pro Gly Lys Arg Glu<br>              635                     640                 645 | 1974 |
| ATC TGT GTG GCT ATC AAG ACT CTG AAA GCT GGT TAT ACA GAC AAA CAG<br>Ile Cys Val Ala Ile Lys Thr Leu Lys Ala Gly Tyr Thr Asp Lys Gln<br>650                      655                     660 | 2022 |
| AGG AGA GAC TTC CTG AGT GAG GCC AGC ATC ATG GGA CAG TTT GAC CAT<br>Arg Arg Asp Phe Leu Ser Glu Ala Ser Ile Met Gly Gln Phe Asp His<br>              665                     670                 675 | 2070 |
| CCG AAC ATC ATT CAC TTG GAA GGC GTG GTC ACT AAA TGT AAA CCA GTA<br>Pro Asn Ile Ile His Leu Glu Gly Val Val Thr Lys Cys Lys Pro Val<br>680                      685                     690                 695 | 2118 |
| ATG ATC ATA ACA GAG TAC ATG GAG AAT GGC TCC TTG GAT GCA TTC CTC<br>Met Ile Ile Thr Glu Tyr Met Glu Asn Gly Ser Leu Asp Ala Phe Leu<br>                  700                     705                 710 | 2166 |
| AGG AAA AAT GAT GGC AGA TTT ACA GTC ATT CAG CTG GTG GGC ATG CTT<br>Arg Lys Asn Asp Gly Arg Phe Thr Val Ile Gln Leu Val Gly Met Leu<br>              715                     720                 725 | 2214 |
| CGT GGC ATT GGG TCT GGG ATG AAG TAT TTA TCT GAT ATG AGC TAT GTG<br>Arg Gly Ile Gly Ser Gly Met Lys Tyr Leu Ser Asp Met Ser Tyr Val<br>730                      735                     740 | 2262 |
| CAT CGT GAT CTG GCC GCA CGG AAC ATC CTG GTG AAC AGC AAC TTG GTC<br>His Arg Asp Leu Ala Ala Arg Asn Ile Leu Val Asn Ser Asn Leu Val<br>              745                     750                 755 | 2310 |
| TGC AAA GTG TCT GAT TTT GGC ATG TCC CGA GTG CTT GAG GAT GAT CCG<br>Cys Lys Val Ser Asp Phe Gly Met Ser Arg Val Leu Glu Asp Asp Pro<br>760                      765                     770                 775 | 2358 |
| GAA GCA GCT TAC ACC ACC AGG GGT GGC AAG ATT CCT ATC CGG TGG ACT<br>Glu Ala Ala Tyr Thr Thr Arg Gly Gly Lys Ile Pro Ile Arg Trp Thr | 2406 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 780 |     |     |     |     | 785 |     |     |     |     | 790 |     |      |
| GCG | CCA | GAA | GCA | ATT | GCC | TAT | CGT | AAA | TTC | ACA | TCA | GCA | AGT | GAT | GTA | 2454 |
| Ala | Pro | Glu | Ala | Ile | Ala | Tyr | Arg | Lys | Phe | Thr | Ser | Ala | Ser | Asp | Val |      |
|     |     |     | 795 |     |     |     | 800 |     |     |     |     | 805 |     |     |     |      |
| TGG | AGC | TAT | GGA | ATC | GTT | ATG | TGG | GAA | GTG | ATG | TCG | TAC | GGG | GAG | AGG | 2502 |
| Trp | Ser | Tyr | Gly | Ile | Val | Met | Trp | Glu | Val | Met | Ser | Tyr | Gly | Glu | Arg |      |
|     |     | 810 |     |     |     |     | 815 |     |     |     |     | 820 |     |     |     |      |
| CCC | TAT | TGG | GAT | ATG | TCC | AAT | CAA | GAT | GTG | ATT | AAA | GCC | ATT | GAG | GAA | 2550 |
| Pro | Tyr | Trp | Asp | Met | Ser | Asn | Gln | Asp | Val | Ile | Lys | Ala | Ile | Glu | Glu |      |
|     | 825 |     |     |     |     | 830 |     |     |     |     | 835 |     |     |     |     |      |
| GGC | TAT | CGG | TTA | CCC | CCT | CCA | ATG | GAC | TGC | CCC | ATT | GCG | CTC | CAC | CAG | 2598 |
| Gly | Tyr | Arg | Leu | Pro | Pro | Pro | Met | Asp | Cys | Pro | Ile | Ala | Leu | His | Gln |      |
| 840 |     |     |     |     | 845 |     |     |     |     | 850 |     |     |     |     | 855 |      |
| CTG | ATG | CTA | GAC | TGC | TGG | CAG | AAG | GAG | AGG | AGC | GAC | AGG | CCT | AAA | TTT | 2646 |
| Leu | Met | Leu | Asp | Cys | Trp | Gln | Lys | Glu | Arg | Ser | Asp | Arg | Pro | Lys | Phe |      |
|     |     |     |     | 860 |     |     |     |     | 865 |     |     |     |     | 870 |     |      |
| GGG | CAG | ATT | GTC | AAC | ATG | TTG | GAC | AAA | CTC | ATC | CGC | AAC | CCC | AAC | AGC | 2694 |
| Gly | Gln | Ile | Val | Asn | Met | Leu | Asp | Lys | Leu | Ile | Arg | Asn | Pro | Asn | Ser |      |
|     |     |     | 875 |     |     |     | 880 |     |     |     |     | 885 |     |     |     |      |
| TTG | AAG | AGG | ACA | GGG | ACG | GAG | AGC | TCC | AGA | CCT | AAC | ACT | GCC | TTG | TTG | 2742 |
| Leu | Lys | Arg | Thr | Gly | Thr | Glu | Ser | Ser | Arg | Pro | Asn | Thr | Ala | Leu | Leu |      |
|     |     | 890 |     |     |     |     | 895 |     |     |     |     | 900 |     |     |     |      |
| GAT | CCA | AGC | TCC | CCT | GAA | TTC | TCT | GCT | GTG | GTA | TCA | GTG | GGC | GAT | TGG | 2790 |
| Asp | Pro | Ser | Ser | Pro | Glu | Phe | Ser | Ala | Val | Val | Ser | Val | Gly | Asp | Trp |      |
|     | 905 |     |     |     |     | 910 |     |     |     |     | 915 |     |     |     |     |      |
| CTC | CAG | GCC | ATT | AAA | ATG | GAC | CGG | TAT | AAG | GAT | AAC | TTC | ACA | GCT | GCT | 2838 |
| Leu | Gln | Ala | Ile | Lys | Met | Asp | Arg | Tyr | Lys | Asp | Asn | Phe | Thr | Ala | Ala |      |
| 920 |     |     |     |     | 925 |     |     |     |     | 930 |     |     |     |     | 935 |      |
| GGT | TAT | ACC | ACA | CTA | GAG | GCT | GTG | GTG | CAC | GTG | AAC | CAG | GAG | GAC | CTG | 2886 |
| Gly | Tyr | Thr | Thr | Leu | Glu | Ala | Val | Val | His | Val | Asn | Gln | Glu | Asp | Leu |      |
|     |     |     |     | 940 |     |     |     |     | 945 |     |     |     |     | 950 |     |      |
| GCA | AGA | ATT | GGT | ATC | ACA | GCC | ATC | ACG | CAC | CAG | AAT | AAG | ATT | TTG | AGC | 2934 |
| Ala | Arg | Ile | Gly | Ile | Thr | Ala | Ile | Thr | His | Gln | Asn | Lys | Ile | Leu | Ser |      |
|     |     |     | 955 |     |     |     | 960 |     |     |     |     | 965 |     |     |     |      |
| AGT | GTC | CAG | GCA | ATG | CGA | ACC | CAA | ATG | CAG | CAG | ATG | CAC | GGC | AGA | ATG | 2982 |
| Ser | Val | Gln | Ala | Met | Arg | Thr | Gln | Met | Gln | Gln | Met | His | Gly | Arg | Met |      |
|     | 970 |     |     |     |     | 975 |     |     |     |     | 980 |     |     |     |     |      |
| GTT | CCC | GTC | TGA | GCCAGTACTG | | AATAAACTCA | | AAACTCTTGA | | AATTAGTTTA | | | | | | 3034 |
| Val | Pro | Val | *   |     |     |     |     |     |     |     |     |     |     |     |     |      |
|     | 985 |     |     |     |     |     |     |     |     |     |     |     |     |     |     |      |

CCTCATCCAT GCACTTTAAT TGAAGAACTG CACTTTTTTT ACTTCGTCTT CGCCCTCTGA            3094

AATTAAAGAA ATGAAAAAAA AA                                                   3116

(2) INFORMATION FOR SEQ ID NO:15:

(i) SEQUENCE CHARACTERISTICS:
        (A) LENGTH:   986 amino acids
        (B) TYPE: amino acid
        (D) TOPOLOGY: linear (ii) MOLECULE TYPE: protein (xi) SEQUENCE DESCRIPTION: SEQ ID NO:15:

Met Ala Gly Ile Phe Tyr Phe Ala Leu Phe Ser Cys Leu Phe Gly Ile
 1               5                  10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

```
Pro Leu Glu Gly Gly Trp Glu Val Ser Ile Met Asp Glu Lys Asn
     50                  55                  60

Thr Pro Ile Arg Thr Tyr Gln Val Cys Asn Val Met Glu Pro Ser Gln
 65              70                  75                  80

Asn Asn Trp Leu Arg Thr Asp Trp Ile Thr Arg Glu Gly Ala Gln Arg
                 85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
            115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
            195                 200                 205

Arg Asn Leu Ala Gln Phe Pro Asp Thr Ile Thr Gly Ala Asp Thr Ser
210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
        355                 360                 365

Cys Gly Ala Gly Asp Pro Ser Lys Cys Arg Pro Cys Gly Ser Gly Val
        370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
            420                 425                 430

Thr Val Thr Thr Asn Gln Ala Ala Pro Ser Ser Ile Ala Leu Val Gln
        435                 440                 445

Ala Lys Glu Val Thr Arg Tyr Ser Val Ala Leu Ala Trp Leu Glu Pro
450                 455                 460

Asp Arg Pro Asn Gly Val Ile Leu Glu Tyr Glu Val Lys Tyr Tyr Glu
```

```
                465                 470                 475                 480
Lys Asp Gln Asn Glu Arg Ser Tyr Arg Ile Val Arg Thr Ala Ala Arg
                    485                 490                 495
Asn Thr Asp Ile Lys Gly Leu Asn Pro Leu Thr Ser Tyr Val Phe His
            500                 505                 510
Val Arg Ala Arg Thr Ala Ala Gly Tyr Gly Asp Phe Ser Glu Pro Leu
            515                 520                 525
Glu Val Thr Thr Asn Thr Val Pro Ser Arg Ile Ile Gly Asp Gly Ala
        530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Ser Lys Tyr
                565                 570                 575
Ser Lys Ala Lys Gln Glu Ala Asp Glu Lys His Leu Asn Gln Gly
            580                 585                 590
Val Arg Thr Tyr Val Asp Pro Phe Thr Tyr Glu Asp Pro Asn Gln Ala
        595                 600                 605
Val Arg Glu Phe Ala Lys Glu Ile Asp Ala Ser Cys Ile Lys Ile Glu
        610                 615                 620
Lys Val Ile Gly Val Gly Glu Phe Gly Glu Val Cys Ser Gly Arg Leu
625                 630                 635                 640
Lys Val Pro Gly Lys Arg Glu Ile Cys Val Ala Ile Lys Thr Leu Lys
                645                 650                 655
Ala Gly Tyr Thr Asp Lys Gln Arg Arg Asp Phe Leu Ser Glu Ala Ser
                660                 665                 670
Ile Met Gly Gln Phe Asp His Pro Asn Ile Ile His Leu Glu Gly Val
            675                 680                 685
Val Thr Lys Cys Lys Pro Val Met Ile Ile Thr Glu Tyr Met Glu Asn
        690                 695                 700
Gly Ser Leu Asp Ala Phe Leu Arg Lys Asn Asp Gly Arg Phe Thr Val
705                 710                 715                 720
Ile Gln Leu Val Gly Met Leu Arg Gly Ile Gly Ser Gly Met Lys Tyr
                725                 730                 735
Leu Ser Asp Met Ser Tyr Val His Arg Asp Leu Ala Ala Arg Asn Ile
                740                 745                 750
Leu Val Asn Ser Asn Leu Val Cys Lys Val Ser Asp Phe Gly Met Ser
            755                 760                 765
Arg Val Leu Glu Asp Asp Pro Glu Ala Ala Tyr Thr Thr Arg Gly Gly
        770                 775                 780
Lys Ile Pro Ile Arg Trp Thr Ala Pro Glu Ala Ile Ala Tyr Arg Lys
785                 790                 795                 800
Phe Thr Ser Ala Ser Asp Val Trp Ser Tyr Gly Ile Val Met Trp Glu
                805                 810                 815
Val Met Ser Tyr Gly Glu Arg Pro Tyr Trp Asp Met Ser Asn Gln Asp
            820                 825                 830
Val Ile Lys Ala Ile Glu Glu Gly Tyr Arg Leu Pro Pro Pro Met Asp
            835                 840                 845
Cys Pro Ile Ala Leu His Gln Leu Met Leu Asp Cys Trp Gln Lys Glu
        850                 855                 860
Arg Ser Asp Arg Pro Lys Phe Gly Gln Ile Val Asn Met Leu Asp Lys
865                 870                 875                 880
Leu Ile Arg Asn Pro Asn Ser Leu Lys Arg Thr Gly Thr Glu Ser Ser
                885                 890                 895
```

```
Arg Pro Asn Thr Ala Leu Leu Asp Pro Ser Ser Pro Glu Phe Ser Ala
            900                 905                 910
Val Val Ser Val Gly Asp Trp Leu Gln Ala Ile Lys Met Asp Arg Tyr
            915                 920                 925
Lys Asp Asn Phe Thr Ala Ala Gly Tyr Thr Thr Leu Glu Ala Val Val
            930                 935                 940
His Val Asn Gln Glu Asp Leu Ala Arg Ile Gly Ile Thr Ala Ile Thr
945                 950                 955                 960
His Gln Asn Lys Ile Leu Ser Ser Val Gln Ala Met Arg Thr Gln Met
                965                 970                 975
Gln Gln Met His Gly Arg Met Val Pro Val
            980                 985

(2) INFORMATION FOR SEQ ID NO:16:

(i) SEQUENCE CHARACTERISTICS:
        (A) LENGTH: 4529 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 186..3182

(xi) SEQUENCE DESCRIPTION: SEQ ID NO:16:

CGGTGCGAGC GAACAGGAGT GGGGGGGAAA TTAAAAAAAG CTAAACGTGG AGCAGCCGAT        60

CGGGGACCGA AAGGGGAAT CGATGCAAGG AGCACACTAA AACAAAAGCT ACTTCGGAAC        120

AAACAGCATT TAAAAATCCA CGACTCAAGA TAACTGAAAC CTAAAATAAA ACCTGCTCAT       180

GCACC ATG GTT TTT CAA ACT CGG TAC CCT TCA TGG ATT ATT TTA TGC          227
      Met Val Phe Gln Thr Arg Tyr Pro Ser Trp Ile Ile Leu Cys
        1               5                  10

TAC ATC TGG CTG CTC CGC TTT GCA CAC ACA GGG GAG GCG CAG GCT GCG         275
Tyr Ile Trp Leu Leu Arg Phe Ala His Thr Gly Glu Ala Gln Ala Ala
 15              20                  25                  30

AAG GAA GTA CTA CTG CTG GAT TCT AAA GCA CAA CAA ACA GAG TTG GAG         323
Lys Glu Val Leu Leu Leu Asp Ser Lys Ala Gln Gln Thr Glu Leu Glu
            35                  40                  45

TGG ATT TCC TCT CCA CCC AAT GGG TGG GAA GAA ATT AGT GGT TTG GAT         371
Trp Ile Ser Ser Pro Pro Asn Gly Trp Glu Glu Ile Ser Gly Leu Asp
        50                  55                  60

GAG AAC TAT ACC CCG ATA CGA ACA TAC CAG GTG TGC CAA GTC ATG GAG         419
Glu Asn Tyr Thr Pro Ile Arg Thr Tyr Gln Val Cys Gln Val Met Glu
65                  70                  75

CCC AAC CAA AAC AAC TGG CTG CGG ACT AAC TGG ATT TCC AAA GGC AAT         467
Pro Asn Gln Asn Asn Trp Leu Arg Thr Asn Trp Ile Ser Lys Gly Asn
        80                  85                  90

GCA CAA AGG ATT TTT GTA GAA TTG AAA TTC ACC CTG AGG GAT TGT AAC         515
Ala Gln Arg Ile Phe Val Glu Leu Lys Phe Thr Leu Arg Asp Cys Asn
 95                 100                 105                 110

AGT CTT CCT GGA GTA CTG GGA ACT TGC AAG GAA ACA TTT AAT TTG TAC         563
Ser Leu Pro Gly Val Leu Gly Thr Cys Lys Glu Thr Phe Asn Leu Tyr
                115                 120                 125

TAT TAT GAA ACA GAC TAT GAC ACT GGC AGG AAT ATA AGA GAA AAC CTC         611
Tyr Tyr Glu Thr Asp Tyr Asp Thr Gly Arg Asn Ile Arg Glu Asn Leu
            130                 135                 140

TAT GTA AAA ATA GAC ACC ATT GCT GCA GAT GAA AGT TTT ACC CAA GGT         659
```

-continued

```
                Tyr Val Lys Ile Asp Thr Ile Ala Ala Asp Glu Ser Phe Thr Gln Gly
                        145                 150                 155

GAC CTT GGT GAA AGA AAG ATG AAG CTT AAC ACT GAG GTG AGA GAG ATT               707
Asp Leu Gly Glu Arg Lys Met Lys Leu Asn Thr Glu Val Arg Glu Ile
        160                 165                 170

GGA CCT TTG TCC AAA AAG GGA TTC TAT CTT GCC TTT CAG GAT GTA GGG               755
Gly Pro Leu Ser Lys Lys Gly Phe Tyr Leu Ala Phe Gln Asp Val Gly
175                 180                 185                 190

GCT TGC ATA GCT TTG GTT TCT GTC AAA GTG TAC TAC AAG AAG TGC TGG               803
Ala Cys Ile Ala Leu Val Ser Val Lys Val Tyr Tyr Lys Lys Cys Trp
                    195                 200                 205

TCC ATT ATT GAG AAC TTA GCT ATC TTT CCA GAT ACA GTG ACT GGT TCA               851
Ser Ile Ile Glu Asn Leu Ala Ile Phe Pro Asp Thr Val Thr Gly Ser
                210                 215                 220

GAA TTT TCC TCT TTA GTC GAG GTT CGA GGG ACA TGT GTC AGC AGT GCA               899
Glu Phe Ser Ser Leu Val Glu Val Arg Gly Thr Cys Val Ser Ser Ala
            225                 230                 235

GAG GAA GAA GCG GAA AAC GCC CCC AGG ATG CAC TGC AGT GCA GAA GGA               947
Glu Glu Glu Ala Glu Asn Ala Pro Arg Met His Cys Ser Ala Glu Gly
        240                 245                 250

GAA TGG TTA GTG CCC ATT GGA AAA TGT ATC TGC AAA GCA GGC TAC CAG               995
Glu Trp Leu Val Pro Ile Gly Lys Cys Ile Cys Lys Ala Gly Tyr Gln
255                 260                 265                 270

CAA AAA GGA GAC ACT TGT GAA CCC TGT GGC CGT GGG TTC TAC AAG TCT              1043
Gln Lys Gly Asp Thr Cys Glu Pro Cys Gly Arg Gly Phe Tyr Lys Ser
                275                 280                 285

TCC TCT CAA GAT CTT CAG TGC TCT CGT TGT CCA ACT CAC AGT TTT TCT              1091
Ser Ser Gln Asp Leu Gln Cys Ser Arg Cys Pro Thr His Ser Phe Ser
                290                 295                 300

GAT AAA GAA GGC TCC TCC AGA TGT GAA TGT GAA GAT GGG TAT TAC AGG              1139
Asp Lys Glu Gly Ser Ser Arg Cys Glu Cys Glu Asp Gly Tyr Tyr Arg
            305                 310                 315

GCT CCA TCT GAC CCA CCA TAC GTT GCA TGC ACA AGG CCT CCA TCT GCA              1187
Ala Pro Ser Asp Pro Pro Tyr Val Ala Cys Thr Arg Pro Pro Ser Ala
        320                 325                 330

CCA CAG AAC CTC ATT TTC AAC ATC AAC CAA ACC ACA GTA AGT TTG GAA              1235
Pro Gln Asn Leu Ile Phe Asn Ile Asn Gln Thr Thr Val Ser Leu Glu
335                 340                 345                 350

TGG AGT CCT CCT GCA GAC AAT GGG GGA AGA AAC GAT GTG ACC TAC AGA              1283
Trp Ser Pro Pro Ala Asp Asn Gly Gly Arg Asn Asp Val Thr Tyr Arg
                355                 360                 365

ATA TTG TGT AAG CGG TGC AGT TGG GAG CAG GGC GAA TGT GTT CCC TGT              1331
Ile Leu Cys Lys Arg Cys Ser Trp Glu Gln Gly Glu Cys Val Pro Cys
                370                 375                 380

GGG AGT AAC ATT GGA TAC ATG CCC CAG CAG ACT GGA TTA GAG GAT AAC              1379
Gly Ser Asn Ile Gly Tyr Met Pro Gln Gln Thr Gly Leu Glu Asp Asn
            385                 390                 395

TAT GTC ACT GTC ATG GAC CTG CTA GCC CAC GCT AAT TAT ACT TTT GAA              1427
Tyr Val Thr Val Met Asp Leu Leu Ala His Ala Asn Tyr Thr Phe Glu
        400                 405                 410

GTT GAA GCT GTA AAT GGA GTT TCT GAC TTA AGC CGA TCC CAG AGG CTC              1475
Val Glu Ala Val Asn Gly Val Ser Asp Leu Ser Arg Ser Gln Arg Leu
415                 420                 425                 430

TTT GCT GCT GTC AGT ATC ACC ACT GGT CAA GCA GCT CCC TCG CAA GTG              1523
Phe Ala Ala Val Ser Ile Thr Thr Gly Gln Ala Ala Pro Ser Gln Val
                435                 440                 445

AGC GGA GTA ATG AAG GAG AGA GTA CTG CAG CGG AGT GTC GAG CTT TCC              1571
Ser Gly Val Met Lys Glu Arg Val Leu Gln Arg Ser Val Glu Leu Ser
            450                 455                 460
```

```
TGG CAG GAA CCA GAG CAT CCC AAT GGA GTC ATC ACA GAA TAT GAA ATC      1619
Trp Gln Glu Pro Glu His Pro Asn Gly Val Ile Thr Glu Tyr Glu Ile
        465                 470                 475

AAG TAT TAC GAG AAA GAT CAA AGG GAA CGG ACC TAC TCA ACA GTA AAA      1667
Lys Tyr Tyr Glu Lys Asp Gln Arg Glu Arg Thr Tyr Ser Thr Val Lys
        480                 485                 490

ACC AAG TCT ACT TCA GCC TCC ATT AAT AAT CTG AAA CCA GGA ACA GTG      1715
Thr Lys Ser Thr Ser Ala Ser Ile Asn Asn Leu Lys Pro Gly Thr Val
495                 500                 505                 510

TAT GTT TTC CAG ATT CGG GCT TTT ACT GCT GCT GGT TAT GGA AAT TAC      1763
Tyr Val Phe Gln Ile Arg Ala Phe Thr Ala Ala Gly Tyr Gly Asn Tyr
            515                 520                 525

AGT CCC AGA CTT GAT GTT GCT ACA CTA GAG GAA GCT ACA GGT AAA ATG      1811
Ser Pro Arg Leu Asp Val Ala Thr Leu Glu Glu Ala Thr Gly Lys Met
                530                 535                 540

TTT GAA GCT ACA GCT GTC TCC AGT GAA CAG AAT CCT GTT ATT ATC ATT      1859
Phe Glu Ala Thr Ala Val Ser Ser Glu Gln Asn Pro Val Ile Ile Ile
            545                 550                 555

GCT GTG GTT GCT GTA GCT GGG ACC ATC ATT TTG GTG TTC ATG GTC TTT      1907
Ala Val Val Ala Val Ala Gly Thr Ile Ile Leu Val Phe Met Val Phe
560                 565                 570

GGC TTC ATC ATT GGG AGA AGG CAC TGT GGT TAT AGC AAA GCT GAC CAA      1955
Gly Phe Ile Ile Gly Arg Arg His Cys Gly Tyr Ser Lys Ala Asp Gln
575                 580                 585                 590

GAA GGC GAT GAA GAG CTT TAC TTT CAT TTT AAA TTT CCA GGC ACC AAA      2003
Glu Gly Asp Glu Glu Leu Tyr Phe His Phe Lys Phe Pro Gly Thr Lys
                595                 600                 605

ACC TAC ATT GAC CCT GAA ACC TAT GAG GAC CCA AAT AGA GCT GTC CAT      2051
Thr Tyr Ile Asp Pro Glu Thr Tyr Glu Asp Pro Asn Arg Ala Val His
            610                 615                 620

CAA TTC GCC AAG GAG CTA GAT GCC TCC TGT ATT AAA ATT GAG CGT GTG      2099
Gln Phe Ala Lys Glu Leu Asp Ala Ser Cys Ile Lys Ile Glu Arg Val
        625                 630                 635

ATT GGT GCA GGA GAA TTC GGT GAA GTC TGC AGT GGC CGT TTG AAA CTT      2147
Ile Gly Ala Gly Glu Phe Gly Glu Val Cys Ser Gly Arg Leu Lys Leu
640                 645                 650

CCA GGG AAA AGA GAT GTT GCA GTA GCC ATA AAA ACC CTG AAA GTT GGT      2195
Pro Gly Lys Arg Asp Val Ala Val Ala Ile Lys Thr Leu Lys Val Gly
655                 660                 665                 670

TAC ACA GAA AAA CAA AGG AGA GAC TTT TTG TGT GAA GCA AGC ATC ATG      2243
Tyr Thr Glu Lys Gln Arg Arg Asp Phe Leu Cys Glu Ala Ser Ile Met
                675                 680                 685

GGG CAG TTT GAC CAC CCA AAT GTT GTC CAT TTG GAA GGG GTT GTT ACA      2291
Gly Gln Phe Asp His Pro Asn Val Val His Leu Glu Gly Val Val Thr
            690                 695                 700

AGA GGG AAA CCA GTC ATG ATA GTA ATA GAG TTC ATG GAA AAT GGA GCC      2339
Arg Gly Lys Pro Val Met Ile Val Ile Glu Phe Met Glu Asn Gly Ala
        705                 710                 715

CTA GAT GCA TTT CTC AGG AAA CAT GAT GGG CAA TTT ACA GTC ATT CAG      2387
Leu Asp Ala Phe Leu Arg Lys His Asp Gly Gln Phe Thr Val Ile Gln
720                 725                 730

TTA GTA GGA ATG CTG AGA GGA ATT GCT GCT GGA ATG AGA TAT TTG GCT      2435
Leu Val Gly Met Leu Arg Gly Ile Ala Ala Gly Met Arg Tyr Leu Ala
735                 740                 745                 750

GAT ATG GGA TAT GTT CAC AGG GAC CTT GCA GCT CGC AAT ATT CTT GTC      2483
Asp Met Gly Tyr Val His Arg Asp Leu Ala Ala Arg Asn Ile Leu Val
                755                 760                 765

AAC AGC AAT CTC GTT TGT AAA GTG TCA GAT TTT GGC CTG TCC CGA GTT      2531
Asn Ser Asn Leu Val Cys Lys Val Ser Asp Phe Gly Leu Ser Arg Val
            770                 775                 780
```

```
ATA GAG GAT GAT CCA GAA GCT GTC TAT ACA ACT ACT GGT GGA AAA ATT      2579
Ile Glu Asp Asp Pro Glu Ala Val Tyr Thr Thr Thr Gly Gly Lys Ile
            785                 790                 795

CCA GTA AGG TGG ACA GCA CCC GAA GCC ATC CAG TAC CGG AAA TTC ACA      2627
Pro Val Arg Trp Thr Ala Pro Glu Ala Ile Gln Tyr Arg Lys Phe Thr
800                 805                 810

TCA GCC AGT GAT GTA TGG AGC TAT GGA ATA GTC ATG TGG GAA GTT ATG      2675
Ser Ala Ser Asp Val Trp Ser Tyr Gly Ile Val Met Trp Glu Val Met
815                 820                 825                 830

TCT TAT GGA GAA AGA CCT TAT TGG GAC ATG TCA AAT CAA GAT GTT ATA      2723
Ser Tyr Gly Glu Arg Pro Tyr Trp Asp Met Ser Asn Gln Asp Val Ile
            835                 840                 845

AAA GCA ATA GAA GAA GGT TAT CGT TTA CCA GCA CCC ATG GAC TGC CCA      2771
Lys Ala Ile Glu Glu Gly Tyr Arg Leu Pro Ala Pro Met Asp Cys Pro
                850                 855                 860

GCT GGC CTT CAC CAG CTA ATG TTG GAT TGT TGG CAA AAG GAG CGT GCT      2819
Ala Gly Leu His Gln Leu Met Leu Asp Cys Trp Gln Lys Glu Arg Ala
            865                 870                 875

GAA AGG CCA AAA TTT GAA CAG ATA GTT GGA ATT CTA GAC AAA ATG ATT      2867
Glu Arg Pro Lys Phe Glu Gln Ile Val Gly Ile Leu Asp Lys Met Ile
880                 885                 890

CGA AAC CCA AAT AGT CTG AAA ACT CCC CTG GGA ACT TGT AGT AGG CCA      2915
Arg Asn Pro Asn Ser Leu Lys Thr Pro Leu Gly Thr Cys Ser Arg Pro
895                 900                 905                 910

ATA AGC CCT CTT CTG GAT CAA AAC ACT CCT GAT TTC ACT ACC TTT TGT      2963
Ile Ser Pro Leu Leu Asp Gln Asn Thr Pro Asp Phe Thr Thr Phe Cys
            915                 920                 925

TCA GTT GGA GAA TGG CTA CAA GCT ATT AAG ATG GAA AGA TAT AAA GAT      3011
Ser Val Gly Glu Trp Leu Gln Ala Ile Lys Met Glu Arg Tyr Lys Asp
                930                 935                 940

AAT TTC ACG GCA GCT GGC TAC AAT TCC CTT GAA TCA GTA GCC AGG ATG      3059
Asn Phe Thr Ala Ala Gly Tyr Asn Ser Leu Glu Ser Val Ala Arg Met
            945                 950                 955

ACT ATT GAG GAT GTG ATG AGT TTA GGG ATC ACA CTG GTT GGT CAT CAA      3107
Thr Ile Glu Asp Val Met Ser Leu Gly Ile Thr Leu Val Gly His Gln
960                 965                 970

AAG AAA ATC ATG AGC AGC ATT CAG ACT ATG AGA GCA CAA ATG CTA CAT      3155
Lys Lys Ile Met Ser Ser Ile Gln Thr Met Arg Ala Gln Met Leu His
975                 980                 985                 990

TTA CAT GGA ACT GGC ATT CAA GTG TGA TATGCATTTC TCCCTTTTAA            3202
Leu His Gly Thr Gly Ile Gln Val  *
            995

GGGAGATTAC AGACTGCAAG AGAACAGTAC TGGCCTTCAG TATATGCATA GAATGCTGCT    3262

AGAAGACAAG TGATGTCCTG GGTCCTTCCA ACAGTGAAGA GAAGATTTAA GAAGCACCTA    3322

TAGACTTGAA CTCCTAAGTG CCACCAGAAT ATATAAAAAG GGAATTTAGG ATCCACCATC    3382

GGTGGCCAGG AAAATAGCAG TGACAATAAA CAAAGTACTA CCTGAAAAAC ATCCAAACAC    3442

CTTGAGCTCT CTAACCTCCT TTTTGTCTTA TAGACTTTTT AAAATGTACA TAAAGAATTT    3502

AAGAAAGAAT ATATTTGTCA AATAAAATCA TGATCTTATT GTTAAAATTA ATGAAATATT    3562

TTCCTTAAAT ATGTGATTTC AGACTATTCC TTTTTAAAAT CATTTGTGTT TATTCTTCAT    3622

AAGGACTTTG TTTAGAAAG CTGTTTATAG CTTTGGACCT TTTTAGTGTT AAATCTGTAA     3682

CATTACTACA CTGGGTACCT TTGAAAGAAT CTCAAATTTC AAAAGAAATA GCATGATTGA    3742

AGATACATCT CTGTTAGAAC ATTGGTATCC TTTTTGTGCC ATTTTATTCT GTTTAATCAG    3802

TGCTGTTTTG ATATTGTTTG CTAATTGGCA GGTAGTCAAG AAAAATGCAAG TTGCCAAGAG   3862
```

-continued

```
CTCTGATATT TTTTAAAAAG AATTTTTTTG TAAAGATCAG ACAACACACT ATCTTTTCAA    3922

TGAAAAAAGC AATAATGATC CATACATACT ATAAGGCACT TTAACAGAT TGTTTATAGA     3982

GTGATTTTAC TAGAAAGAAT TTAATAAACT CGAAGTTTAG GTTTATGAGT ATATAAACAA    4042

ATGAGGCACT TCATCTGAAG AATGTTGGTG AAGGCAAGTC TCTGAAAGCA GAACTATCCA    4102

GTGTTATCTA AAAATTAATC TGAGCACATC AAGATTTTTT CATTCTCGTG ACATTAGGAA    4162

ATTTAGGATA AATAGTTGAC ATATATTTTA TATCCTCTTC TGTTGAATGC AGTCCAAACA    4222

TGAAAGGAAA TAATTGTTTT ATATTATAAC TCTGAAGCAT GATAAAGGGG CAGTTCACAA    4282

TTTTCACCAT TTAAACACAA ATTTGCTGCA CAGAATATCA CCATTGCAGT TCAAAACAAA    4342

ACAAAACAAA AAGTCTTTTG TTTGTGAACA CTGATGCAAG AAACTTGTTA AATGAAAGGA    4402

CTCTTTACCC TAGAAGGAAG AGGTGAAGGA TCTGGCTTGT TTTTAAAGCT TTATTTATTA    4462

AACCATATTA TTTGATTACT GTGTTAGAAT TTCATAAGCA ATAATTAAAT GTGTCTTTAT    4522

GGAATTC                                                             4529
```

(2) INFORMATION FOR SEQ ID NO:17:

(i) SEQUENCE CHARACTERISTICS:
        (A) LENGTH: 998 amino acids
        (B) TYPE: amino acid
        (D) TOPOLOGY: linear (ii) MOLECULE TYPE: protein (xi) SEQUENCE DESCRIPTION: SEQ ID NO:17:

```
Met Val Phe Gln Thr Arg Tyr Pro Ser Trp Ile Ile Leu Cys Tyr Ile
 1               5                  10                  15

Trp Leu Leu Arg Phe Ala His Thr Gly Glu Ala Gln Ala Ala Lys Glu
            20                  25                  30

Val Leu Leu Leu Asp Ser Lys Ala Gln Gln Thr Glu Leu Glu Trp Ile
        35                  40                  45

Ser Ser Pro Pro Asn Gly Trp Glu Glu Ile Ser Gly Leu Asp Glu Asn
    50                  55                  60

Tyr Thr Pro Ile Arg Thr Tyr Gln Val Cys Gln Val Met Glu Pro Asn
65                  70                  75                  80

Gln Asn Asn Trp Leu Arg Thr Asn Trp Ile Ser Lys Gly Asn Ala Gln
                85                  90                  95

Arg Ile Phe Val Glu Leu Lys Phe Thr Leu Arg Asp Cys Asn Ser Leu
            100                 105                 110

Pro Gly Val Leu Gly Thr Cys Lys Glu Thr Phe Asn Leu Tyr Tyr Tyr
        115                 120                 125

Glu Thr Asp Tyr Asp Thr Gly Arg Asn Ile Arg Glu Asn Leu Tyr Val
    130                 135                 140

Lys Ile Asp Thr Ile Ala Ala Asp Glu Ser Phe Thr Gln Gly Asp Leu
145                 150                 155                 160

Gly Glu Arg Lys Met Lys Leu Asn Thr Glu Val Arg Glu Ile Gly Pro
                165                 170                 175

Leu Ser Lys Lys Gly Phe Tyr Leu Ala Phe Gln Asp Val Gly Ala Cys
            180                 185                 190

Ile Ala Leu Val Ser Val Lys Val Tyr Tyr Lys Lys Cys Trp Ser Ile
        195                 200                 205

Ile Glu Asn Leu Ala Ile Phe Pro Asp Thr Val Thr Gly Ser Glu Phe
    210                 215                 220

Ser Ser Leu Val Glu Val Arg Gly Thr Cys Val Ser Ser Ala Glu Glu
```

```
              225                 230                 235                 240

Glu Ala Glu Asn Ala Pro Arg Met His Cys Ser Ala Glu Gly Glu Trp
                245                 250                 255

Leu Val Pro Ile Gly Lys Cys Ile Cys Lys Ala Gly Tyr Gln Gln Lys
                260                 265                 270

Gly Asp Thr Cys Glu Pro Cys Gly Arg Gly Phe Tyr Lys Ser Ser Ser
                275                 280                 285

Gln Asp Leu Gln Cys Ser Arg Cys Pro Thr His Ser Phe Ser Asp Lys
            290                 295                 300

Glu Gly Ser Ser Arg Cys Glu Cys Glu Asp Gly Tyr Tyr Arg Ala Pro
305                 310                 315                 320

Ser Asp Pro Pro Tyr Val Ala Cys Thr Arg Pro Pro Ser Ala Pro Gln
                325                 330                 335

Asn Leu Ile Phe Asn Ile Asn Gln Thr Thr Val Ser Leu Glu Trp Ser
                340                 345                 350

Pro Pro Ala Asp Asn Gly Gly Arg Asn Asp Val Thr Tyr Arg Ile Leu
            355                 360                 365

Cys Lys Arg Cys Ser Trp Glu Gln Gly Glu Cys Val Pro Cys Gly Ser
        370                 375                 380

Asn Ile Gly Tyr Met Pro Gln Gln Thr Gly Leu Glu Asp Asn Tyr Val
385                 390                 395                 400

Thr Val Met Asp Leu Leu Ala His Ala Asn Tyr Thr Phe Glu Val Glu
                405                 410                 415

Ala Val Asn Gly Val Ser Asp Leu Ser Arg Ser Gln Arg Leu Phe Ala
            420                 425                 430

Ala Val Ser Ile Thr Thr Gly Gln Ala Ala Pro Ser Gln Val Ser Gly
            435                 440                 445

Val Met Lys Glu Arg Val Leu Gln Arg Ser Val Glu Leu Ser Trp Gln
    450                 455                 460

Glu Pro Glu His Pro Asn Gly Val Ile Thr Glu Tyr Glu Ile Lys Tyr
465                 470                 475                 480

Tyr Glu Lys Asp Gln Arg Glu Arg Thr Tyr Ser Thr Val Lys Thr Lys
                485                 490                 495

Ser Thr Ser Ala Ser Ile Asn Asn Leu Lys Pro Gly Thr Val Tyr Val
            500                 505                 510

Phe Gln Ile Arg Ala Phe Thr Ala Ala Gly Tyr Gly Asn Tyr Ser Pro
        515                 520                 525

Arg Leu Asp Val Ala Thr Leu Glu Glu Ala Thr Gly Lys Met Phe Glu
    530                 535                 540

Ala Thr Ala Val Ser Ser Glu Gln Asn Pro Val Ile Ile Ala Val
545                 550                 555                 560

Val Ala Val Ala Gly Thr Ile Ile Leu Val Phe Met Val Phe Gly Phe
                565                 570                 575

Ile Ile Gly Arg Arg His Cys Gly Tyr Ser Lys Ala Asp Gln Glu Gly
            580                 585                 590

Asp Glu Glu Leu Tyr Phe His Phe Lys Phe Pro Gly Thr Lys Thr Tyr
        595                 600                 605

Ile Asp Pro Glu Thr Tyr Glu Asp Pro Asn Arg Ala Val His Gln Phe
    610                 615                 620

Ala Lys Glu Leu Asp Ala Ser Cys Ile Lys Ile Glu Arg Val Ile Gly
625                 630                 635                 640

Ala Gly Glu Phe Gly Glu Val Cys Ser Gly Arg Leu Lys Leu Pro Gly
                645                 650                 655
```

-continued

```
Lys Arg Asp Val Ala Val Ala Ile Lys Thr Leu Lys Val Gly Tyr Thr
            660                 665                 670

Glu Lys Gln Arg Arg Asp Phe Leu Cys Glu Ala Ser Ile Met Gly Gln
        675                 680                 685

Phe Asp His Pro Asn Val Val His Leu Glu Gly Val Val Thr Arg Gly
    690                 695                 700

Lys Pro Val Met Ile Val Ile Glu Phe Met Glu Asn Gly Ala Leu Asp
705                 710                 715                 720

Ala Phe Leu Arg Lys His Asp Gly Gln Phe Thr Val Ile Gln Leu Val
                725                 730                 735

Gly Met Leu Arg Gly Ile Ala Ala Gly Met Arg Tyr Leu Ala Asp Met
            740                 745                 750

Gly Tyr Val His Arg Asp Leu Ala Ala Arg Asn Ile Leu Val Asn Ser
        755                 760                 765

Asn Leu Val Cys Lys Val Ser Asp Phe Gly Leu Ser Arg Val Ile Glu
    770                 775                 780

Asp Asp Pro Glu Ala Val Tyr Thr Thr Thr Gly Gly Lys Ile Pro Val
785                 790                 795                 800

Arg Trp Thr Ala Pro Glu Ala Ile Gln Tyr Arg Lys Phe Thr Ser Ala
                805                 810                 815

Ser Asp Val Trp Ser Tyr Gly Ile Val Met Trp Glu Val Met Ser Tyr
            820                 825                 830

Gly Glu Arg Pro Tyr Trp Asp Met Ser Asn Gln Asp Val Ile Lys Ala
        835                 840                 845

Ile Glu Glu Gly Tyr Arg Leu Pro Ala Pro Met Asp Cys Pro Ala Gly
    850                 855                 860

Leu His Gln Leu Met Leu Asp Cys Trp Gln Lys Glu Arg Ala Glu Arg
865                 870                 875                 880

Pro Lys Phe Glu Gln Ile Val Gly Ile Leu Asp Lys Met Ile Arg Asn
                885                 890                 895

Pro Asn Ser Leu Lys Thr Pro Leu Gly Thr Cys Ser Arg Pro Ile Ser
            900                 905                 910

Pro Leu Leu Asp Gln Asn Thr Pro Asp Phe Thr Thr Phe Cys Ser Val
        915                 920                 925

Gly Glu Trp Leu Gln Ala Ile Lys Met Glu Arg Tyr Lys Asp Asn Phe
    930                 935                 940

Thr Ala Ala Gly Tyr Asn Ser Leu Glu Ser Val Ala Arg Met Thr Ile
945                 950                 955                 960

Glu Asp Val Met Ser Leu Gly Ile Thr Leu Val Gly His Gln Lys Lys
                965                 970                 975

Ile Met Ser Ser Ile Gln Thr Met Arg Ala Gln Met Leu His Leu His
            980                 985                 990

Gly Thr Gly Ile Gln Val
        995
```

(2) INFORMATION FOR SEQ ID NO:18:

(i) SEQUENCE CHARACTERISTICS:
        (A) LENGTH: 976 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

-continued

```
Met Glu Leu Gln Ala Ala Arg Ala Cys Phe Ala Leu Leu Trp Gly Cys
 1               5                  10                 15

Ala Leu Ala Ala Ala Ala Ala Gln Gly Lys Glu Val Val Leu Leu
            20                  25                  30

Asp Phe Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
 50                  55                  60

Tyr Met Tyr Ser Val Cys Asn Val Met Ser Gly Asp Gln Asp Asn Trp
 65                  70                  75                  80

Leu Arg Thr Asn Trp Val Tyr Arg Gly Glu Ala Glu Arg Asn Asn Phe
            85                  90                  95

Glu Leu Asn Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
 130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
            165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
            195                 200                 205

Ala His Phe Pro Glu Thr Ile Ala Gly Ser Asp Ala Pro Ser Leu Ala
            210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
            245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
            275                 280                 285

Pro Cys Leu Glu Cys Pro Glu His Thr Leu Pro Ser Pro Glu Gly Ala
            290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
            370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
            405                 410                 415
```

-continued

```
Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
```

-continued

```
                835                 840                 845
Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
                900                 905                 910

Leu Glu Ser Ile Lys Met Gln Gln Tyr Thr Glu His Phe Met Ala Ala
                915                 920                 925

Gly Tyr Thr Ala Ile Glu Lys Val Val Gln Met Thr Asn Asp Asp Ile
                930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975
```

(2) INFORMATION FOR SEQ ID NO:19:

(i) SEQUENCE CHARACTERISTICS:
        (A) LENGTH: 984 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met Glu Arg Arg Trp Pro Leu Gly Leu Gly Leu Val Leu Leu Leu Cys
1               5                   10                  15

Ala Pro Leu Pro Pro Gly Ala Arg Ala Lys Glu Val Thr Leu Met Asp
                20                  25                  30

Thr Ser Lys Ala Gln Gly Glu Leu Gly Trp Leu Leu Asp Pro Pro Lys
                35                  40                  45

Asp Gly Trp Ser Glu Gln Gln Gln Ile Leu Asn Gly Thr Pro Leu Tyr
50                  55                  60

Met Tyr Gln Asp Cys Pro Met Gln Gly Arg Arg Asp Thr Asp His Trp
65                  70                  75                  80

Leu Arg Ser Asn Trp Ile Tyr Arg Gly Glu Glu Ala Ser Arg Val His
                85                  90                  95

Val Glu Leu Gln Phe Thr Val Arg Asp Cys Lys Ser Phe Pro Gly Gly
                100                 105                 110

Ala Gly Pro Leu Gly Cys Lys Glu Thr Phe Asn Leu Leu Tyr Met Glu
                115                 120                 125

Ser Asp Gln Asp Val Gly Ile Gln Leu Arg Arg Pro Leu Phe Gln Lys
130                 135                 140

Val Thr Thr Val Ala Ala Asp Gln Ser Phe Thr Ile Arg Asp Leu Ala
145                 150                 155                 160

Ser Gly Ser Val Lys Leu Asn Val Glu Arg Cys Ser Leu Gly Arg Leu
                165                 170                 175

Thr Arg Arg Gly Leu Tyr Leu Ala Phe His Asn Pro Gly Ala Cys Val
                180                 185                 190

Ala Leu Val Ser Val Arg Val Phe Tyr Gln Arg Cys Pro Glu Thr Leu
                195                 200                 205

Asn Gly Leu Ala Gln Phe Pro Asp Thr Leu Pro Gly Pro Ala Gly Leu
```

-continued

```
            210                 215                 220
Val Glu Val Ala Gly Thr Cys Leu Pro His Ala Arg Ala Ser Pro Arg
225                 230                 235                 240

Pro Ser Gly Ala Pro Arg Met His Cys Ser Pro Asp Gly Glu Trp Leu
                245                 250                 255

Val Pro Val Gly Arg Cys His Cys Glu Pro Gly Tyr Glu Glu Gly Gly
                260                 265                 270

Ser Gly Glu Ala Cys Val Ala Cys Pro Ser Gly Ser Tyr Arg Met Asp
                275                 280                 285

Met Asp Thr Pro His Cys Leu Thr Cys Pro Gln Gln Ser Thr Ala Glu
290                 295                 300

Ser Glu Gly Ala Thr Ile Cys Thr Cys Glu Ser Gly His Tyr Arg Ala
305                 310                 315                 320

Pro Gly Glu Gly Pro Gln Val Ala Cys Thr Gly Pro Pro Ser Ala Pro
                325                 330                 335

Arg Asn Leu Ser Phe Ser Ala Ser Gly Thr Gln Leu Ser Leu Arg Trp
                340                 345                 350

Glu Pro Pro Ala Asp Thr Gly Gly Arg Gln Asp Val Arg Tyr Ser Val
                355                 360                 365

Arg Cys Ser Gln Cys Gln Gly Thr Ala Gln Asp Gly Gly Pro Cys Gln
370                 375                 380

Pro Cys Gly Val Gly Val His Phe Ser Pro Gly Ala Arg Ala Leu Thr
385                 390                 395                 400

Thr Pro Ala Val His Val Asn Gly Leu Glu Pro Tyr Ala Asn Tyr Thr
                405                 410                 415

Phe Asn Val Glu Ala Gln Asn Gly Val Ser Gly Leu Gly Ser Ser Gly
                420                 425                 430

His Ala Ser Thr Ser Val Ser Ile Ser Met Gly His Ala Glu Ser Leu
                435                 440                 445

Ser Gly Leu Ser Leu Arg Leu Val Lys Lys Glu Pro Arg Gln Leu Glu
450                 455                 460

Leu Thr Trp Ala Gly Ser Arg Pro Arg Ser Pro Gly Ala Asn Leu Thr
465                 470                 475                 480

Tyr Glu Leu His Val Leu Asn Gln Asp Glu Glu Arg Tyr Gln Met Val
                485                 490                 495

Leu Glu Pro Arg Val Leu Leu Thr Glu Leu Gln Pro Asp Thr Thr Tyr
                500                 505                 510

Ile Val Arg Val Arg Met Leu Thr Pro Leu Gly Pro Gly Pro Phe Ser
                515                 520                 525

Pro Asp His Glu Phe Arg Thr Ser Pro Pro Val Ser Arg Gly Leu Thr
530                 535                 540

Gly Gly Glu Ile Val Ala Val Ile Phe Gly Leu Leu Leu Gly Ala Ala
545                 550                 555                 560

Leu Leu Leu Gly Ile Leu Val Phe Arg Ser Arg Arg Ala Gln Arg Gln
                565                 570                 575

Arg Gln Gln Arg His Val Thr Ala Pro Pro Met Trp Ile Glu Arg Thr
                580                 585                 590

Ser Cys Ala Glu Ala Leu Cys Gly Thr Ser Arg His Thr Arg Thr Leu
                595                 600                 605

His Arg Glu Pro Trp Thr Leu Pro Gly Gly Trp Ser Asn Phe Pro Ser
                610                 615                 620

Arg Glu Leu Asp Pro Ala Trp Leu Met Val Asp Thr Val Ile Gly Glu
625                 630                 635                 640
```

-continued

```
Gly Glu Phe Gly Glu Val Tyr Arg Gly Thr Leu Arg Leu Pro Ser Gln
                645                 650                 655

Asp Cys Lys Thr Val Ala Ile Lys Thr Leu Lys Asp Thr Ser Pro Gly
            660                 665                 670

Gly Gln Trp Trp Asn Phe Leu Arg Glu Ala Thr Ile Met Gly Gln Phe
        675                 680                 685

Ser His Pro His Ile Leu His Leu Glu Gly Val Val Thr Lys Arg Lys
    690                 695                 700

Pro Ile Met Ile Ile Thr Glu Phe Met Glu Asn Ala Ala Leu Asp Ala
705                 710                 715                 720

Phe Leu Arg Glu Arg Glu Asp Gln Leu Val Pro Gly Gln Leu Val Ala
                725                 730                 735

Met Leu Gln Gly Ile Ala Ser Gly Met Asn Tyr Leu Ser Asn His Asn
            740                 745                 750

Tyr Val His Arg Asp Leu Ala Ala Arg Asn Ile Leu Val Asn Gln Asn
        755                 760                 765

Leu Cys Cys Lys Val Ser Asp Phe Gly Leu Thr Arg Leu Leu Asp Asp
    770                 775                 780

Phe Asp Gly Thr Tyr Glu Thr Gln Gly Gly Lys Ile Pro Ile Arg Trp
785                 790                 795                 800

Thr Ala Pro Glu Ala Ile Ala His Arg Ile Phe Thr Thr Ala Ser Asp
                805                 810                 815

Val Trp Ser Phe Gly Ile Val Met Trp Glu Val Leu Ser Phe Gly Asp
            820                 825                 830

Lys Pro Tyr Gly Glu Met Ser Asn Gln Glu Val Met Lys Ser Ile Glu
        835                 840                 845

Asp Gly Tyr Arg Leu Pro Pro Pro Val Asp Cys Pro Ala Pro Leu Tyr
    850                 855                 860

Glu Leu Met Lys Asn Cys Trp Ala Tyr Asp Arg Ala Arg Arg Pro His
865                 870                 875                 880

Phe Gln Lys Leu Gln Ala His Leu Glu Gln Leu Leu Ala Asn Pro His
                885                 890                 895

Ser Leu Arg Thr Ile Ala Asn Phe Asp Pro Arg Val Thr Leu Arg Leu
            900                 905                 910

Pro Ser Leu Ser Gly Ser Asp Gly Ile Pro Tyr Arg Thr Val Ser Glu
        915                 920                 925

Trp Leu Glu Ser Ile Arg Met Lys Arg Tyr Ile Leu His Phe His Ser
    930                 935                 940

Ala Gly Leu Asp Thr Met Glu Cys Val Leu Glu Leu Thr Ala Glu Asp
945                 950                 955                 960

Leu Thr Gln Met Gly Ile Thr Leu Pro Gly His Gln Lys Arg Ile Leu
                965                 970                 975

Cys Ser Ile Gln Gly Phe Lys Asp
            980
```

(2) INFORMATION FOR SEQ ID NO:20:

(i) SEQUENCE CHARACTERISTICS:
        (A) LENGTH: 998 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Met Ala Arg Ala Arg Pro Pro Pro Pro Ser Pro Pro Gly Leu
1               5                   10                  15

Leu Pro Leu Leu Pro Pro Leu Leu Leu Pro Leu Leu Leu Pro
            20              25              30

Ala Gly Cys Arg Ala Leu Glu Glu Thr Leu Met Asp Thr Lys Trp Val
            35                  40              45

Thr Ser Glu Leu Ala Trp Thr Ser His Pro Glu Ser Gly Trp Glu Glu
50                      55                  60

Val Ser Gly Tyr Asp Glu Ala Met Asn Pro Ile Arg Thr Tyr Gln Val
65                  70              75                      80

Cys Asn Val Arg Glu Ser Ser Gln Asn Asn Trp Leu Arg Thr Gly Phe
                85              90                  95

Ile Trp Arg Arg Asp Val Gln Arg Val Tyr Val Glu Leu Lys Phe Thr
            100             105             110

Val Arg Asp Cys Asn Ser Ile Pro Asn Ile Pro Gly Ser Cys Lys Glu
            115             120             125

Thr Phe Asn Leu Phe Tyr Tyr Glu Ala Asp Ser Asp Val Ala Ser Ala
    130             135             140

Ser Ser Pro Phe Trp Met Glu Asn Pro Tyr Val Lys Val Asp Thr Ile
145             150             155             160

Ala Pro Asp Glu Ser Phe Ser Arg Leu Asp Ala Gly Arg Val Asn Thr
                165             170             175

Lys Val Arg Ser Phe Gly Pro Leu Ser Lys Ala Gly Phe Tyr Leu Ala
            180             185             190

Phe Gln Asp Gln Gly Ala Cys Met Ser Leu Ile Ser Val Arg Ala Phe
        195             200             205

Tyr Lys Lys Cys Ala Ser Thr Thr Ala Gly Phe Ala Leu Phe Pro Glu
    210             215             220

Thr Leu Thr Gly Ala Glu Pro Thr Ser Leu Val Ile Ala Pro Gly Thr
225             230             235             240

Cys Ile Pro Asn Ala Val Glu Val Ser Val Pro Leu Lys Leu Tyr Cys
            245             250             255

Asn Gly Asp Gly Glu Trp Met Val Pro Val Gly Ala Cys Thr Cys Ala
            260             265             270

Thr Gly His Glu Pro Ala Ala Lys Glu Ser Gln Cys Arg Pro Cys Pro
        275             280             285

Pro Gly Ser Tyr Lys Ala Lys Gln Gly Glu Gly Pro Cys Leu Pro Cys
    290             295             300

Pro Pro Asn Ser Arg Thr Thr Ser Pro Ala Ala Ser Ile Cys Thr Cys
305             310             315             320

His Asn Asn Phe Tyr Arg Ala Asp Ser Asp Ser Ala Asp Ser Ala Cys
            325             330             335

Thr Thr Val Pro Ser Pro Pro Arg Gly Val Ile Ser Asn Val Asn Glu
            340             345             350

Thr Ser Leu Ile Leu Glu Trp Ser Glu Pro Arg Asp Leu Gly Val Arg
        355             360             365

Asp Asp Leu Leu Tyr Asn Val Ile Cys Lys Lys Cys His Gly Ala Gly
        370             375             380

Gly Ala Ser Ala Cys Ser Arg Cys Asp Asp Asn Val Glu Phe Val Pro
385             390             395             400

Arg Gln Leu Gly Leu Ser Glu Pro Arg Val His Thr Ser His Leu Leu
            405             410             415
```

```
Ala His Thr Arg Tyr Thr Phe Glu Val Gln Ala Val Asn Gly Val Ser
            420                 425                 430

Gly Lys Ser Pro Leu Pro Pro Arg Tyr Ala Ala Val Asn Ile Thr Thr
            435                 440                 445

Asn Gln Ala Ala Pro Ser Glu Val Pro Thr Leu Arg Leu His Ser Ser
            450                 455                 460

Ser Gly Ser Ser Leu Thr Leu Ser Trp Ala Pro Pro Glu Arg Pro Asn
465                 470                 475                 480

Gly Val Ile Leu Asp Tyr Glu Met Lys Tyr Phe Glu Lys Ser Glu Gly
                485                 490                 495

Ile Ala Ser Thr Val Thr Ser Gln Met Asn Ser Val Gln Leu Asp Gly
            500                 505                 510

Leu Arg Pro Asp Ala Arg Tyr Val Val Gln Val Arg Ala Arg Thr Val
            515                 520                 525

Ala Gly Tyr Gly Gln Tyr Ser Arg Pro Ala Glu Phe Glu Thr Thr Ser
            530                 535                 540

Glu Arg Gly Ser Gly Ala Gln Gln Leu Gln Glu Gln Leu Pro Leu Ile
545                 550                 555                 560

Val Gly Ser Ala Thr Ala Gly Leu Val Phe Val Ala Val Val Val Val
                565                 570                 575

Ile Ala Ile Val Cys Leu Arg Lys Gln Arg His Gly Ser Asp Ser Glu
            580                 585                 590

Tyr Thr Glu Lys Leu Gln Gln Tyr Ile Ala Pro Gly Met Lys Val Tyr
            595                 600                 605

Ile Asp Pro Phe Thr Tyr Glu Asp Pro Asn Glu Ala Val Arg Glu Phe
            610                 615                 620

Ala Lys Glu Ile Asp Val Ser Cys Val Lys Ile Glu Glu Val Ile Gly
625                 630                 635                 640

Ala Gly Glu Phe Gly Glu Val Cys Arg Gly Arg Leu Lys Gln Pro Gly
                645                 650                 655

Arg Arg Glu Val Phe Val Ala Ile Lys Thr Leu Lys Val Gly Tyr Thr
            660                 665                 670

Glu Arg Gln Arg Arg Asp Phe Leu Ser Glu Ala Ser Ile Met Gly Gln
            675                 680                 685

Phe Asp His Pro Asn Ile Ile Arg Leu Glu Gly Val Val Thr Lys Ser
            690                 695                 700

Arg Pro Val Met Ile Leu Thr Glu Phe Met Glu Asn Cys Ala Leu Asp
705                 710                 715                 720

Ser Phe Leu Arg Leu Asn Asp Gly Gln Phe Thr Val Ile Gln Leu Val
                725                 730                 735

Gly Met Leu Arg Gly Ile Ala Ala Gly Met Lys Tyr Leu Ser Glu Met
            740                 745                 750

Asn Tyr Val His Arg Asp Leu Ala Ala Arg Asn Ile Leu Val Asn Ser
            755                 760                 765

Asn Leu Val Cys Lys Val Ser Asp Phe Gly Leu Ser Arg Phe Leu Glu
            770                 775                 780

Asp Asp Pro Ser Asp Pro Thr Tyr Thr Ser Ser Leu Gly Gly Lys Ile
785                 790                 795                 800

Pro Ile Arg Trp Thr Ala Pro Glu Ala Ile Ala Tyr Arg Lys Phe Thr
                805                 810                 815

Ser Ala Ser Asp Val Trp Ser Tyr Gly Ile Val Met Trp Glu Val Met
            820                 825                 830

Ser Tyr Gly Glu Arg Pro Tyr Trp Asp Met Ser Asn Gln Asp Val Ile
```

-continued

```
                835                 840                 845
Asn Ala Val Glu Gln Asp Tyr Arg Leu Pro Pro Met Asp Cys Pro
            850                 855                 860

Thr Ala Leu His Gln Leu Met Leu Asp Cys Trp Val Arg Asp Arg Asn
865                 870                 875                 880

Leu Arg Pro Lys Phe Ser Gln Ile Val Asn Thr Leu Asp Lys Leu Ile
                885                 890                 895

Arg Asn Ala Ala Ser Leu Lys Val Ile Ala Ser Ala Gln Ser Gly Met
            900                 905                 910

Ser Gln Pro Leu Leu Asp Arg Thr Val Pro Asp Tyr Thr Thr Phe Thr
            915                 920                 925

Thr Val Gly Asp Trp Leu Asp Ala Ile Lys Met Gly Arg Tyr Lys Glu
        930                 935                 940

Ser Phe Val Ser Ala Gly Phe Ala Ser Phe Asp Leu Val Ala Gln Met
945                 950                 955                 960

Thr Ala Glu Asp Leu Leu Arg Ile Gly Val Thr Leu Ala Gly His Gln
                965                 970                 975

Lys Lys Ile Leu Ser Ser Ile Gln Asp Met Arg Leu Gln Met Asn Gln
            980                 985                 990

Thr Leu Pro Val Gln Val
        995
```

(2) INFORMATION FOR SEQ ID NO:21:

(i) SEQUENCE CHARACTERISTICS:
        (A) LENGTH: 983 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Asp Cys Gln Leu Ser Ile Leu Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
```

-continued

```
                180                 185                 190
Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220

Glu Val Arg Gly Ser Cys Val Asn Asn Ser Lys Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
    290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
        355                 360                 365

Asn Ile Lys Gln Cys Glu Pro Cys Ser Pro Asn Val Arg Phe Leu Pro
    370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
                405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
        435                 440                 445

Ser Arg Asn Ser Ile Ser Leu Ser Trp Gln Glu Pro Glu His Pro Asn
    450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
                485                 490                 495

Ser Ser Leu Lys Pro Asp Thr Ile Tyr Val Leu Gln Ile Arg Ala Arg
            500                 505                 510

Thr Ala Ala Gly Tyr Gly Thr Asn Ser Arg Lys Phe Glu Phe Glu Thr
        515                 520                 525

Ser Pro Asp Ser Phe Ser Ile Ser Gly Glu Ser Ser Gln Val Val Met
    530                 535                 540

Ile Ala Ile Ser Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
                565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
        595                 600                 605
```

```
Val His Glu Phe Ala Lys Glu Leu Asp Ala Thr Asn Ile Ser Ile Asp
    610             615                 620
Lys Val Val Gly Ala Gly Glu Phe Gly Glu Val Cys Ser Gly Arg Leu
625             630                 635                 640
Lys Leu Pro Ser Lys Lys Glu Ile Ser Val Ala Ile Lys Thr Leu Lys
                645                 650                 655
Val Gly Tyr Thr Glu Lys Gln Arg Arg Asp Phe Leu Gly Glu Ala Ser
            660                 665                 670
Ile Met Gly Gln Phe Asp His Pro Asn Ile Ile Arg Leu Glu Gly Val
        675                 680                 685
Val Thr Lys Ser Lys Pro Val Met Ile Val Thr Glu Tyr Met Glu Asn
    690                 695                 700
Gly Ser Leu Asp Ser Phe Leu Arg Lys His Asp Ala Gln Phe Thr Val
705                 710                 715                 720
Ile Gln Leu Val Gly Met Leu Arg Gly Ile Ala Ser Gly Met Lys Tyr
                725                 730                 735
Leu Ser Asp Met Gly Tyr Val His Arg Asp Leu Ala Ala Arg Asn Ile
            740                 745                 750
Leu Ile Asn Ser Asn Leu Val Cys Lys Val Ser Asp Phe Gly Leu Ser
        755                 760                 765
Arg Val Leu Glu Asp Asp Pro Glu Ala Ala Tyr Thr Thr Arg Gly Gly
    770                 775                 780
Lys Ile Pro Ile Arg Trp Thr Ser Pro Glu Ala Ile Ala Tyr Arg Lys
785                 790                 795                 800
Phe Thr Ser Ala Ser Asp Val Trp Ser Tyr Gly Ile Val Leu Trp Glu
                805                 810                 815
Val Met Ser Tyr Gly Glu Arg Pro Tyr Trp Glu Met Ser Asn Gln Asp
            820                 825                 830
Val Ile Lys Ala Val Asp Glu Gly Tyr Arg Leu Pro Pro Pro Met Asp
        835                 840                 845
Cys Pro Ala Ala Leu Tyr Gln Leu Met Leu Asp Cys Trp Gln Lys Asp
    850                 855                 860
Arg Asn Asn Arg Pro Lys Phe Glu Gln Ile Val Ser Ile Leu Asp Lys
865                 870                 875                 880
Leu Ile Arg Asn Pro Gly Ser Leu Lys Ile Ile Thr Ser Ala Ala Ala
                885                 890                 895
Arg Pro Ser Asn Leu Leu Leu Asp Gln Ser Asn Val Asp Ile Ser Thr
            900                 905                 910
Phe Arg Thr Thr Gly Asp Trp Leu Asn Gly Val Arg Thr Ala His Cys
        915                 920                 925
Lys Glu Ile Phe Thr Gly Val Glu Tyr Ser Ser Cys Asp Thr Ile Ala
    930                 935                 940
Lys Ile Ser Thr Asp Asp Met Lys Lys Val Gly Val Thr Val Val Gly
945                 950                 955                 960
Pro Gln Lys Lys Ile Ile Ser Ser Ile Lys Ala Leu Glu Thr Gln Ser
                965                 970                 975
Lys Asn Gly Pro Val Pro Val
            980
```

(2) INFORMATION FOR SEQ ID NO:22:

(i) SEQUENCE CHARACTERISTICS:
        (A) LENGTH: 24 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:22:

CTGCTCGCCG CCGTGGAAGA AACG                                              24

(2) INFORMATION FOR SEQ ID NO:23:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GCGTCTAGAT TATCACTTCT CCTGGATGCT TGTCTGGTA                               39

(2) INFORMATION FOR SEQ ID NO:24:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GCGGACGCCG CCGCCATGGC CCTGGATTGC CTGCTGCTGT TCCTCCTG                     48

(2) INFORMATION FOR SEQ ID NO:25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CGTTTCTTCC ACGGCGGCGA GCAGAGATGC CAGGAGGAAC AGCAGCAGGC AATC              54

(2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Met Ala Leu Asp Cys Leu Leu Leu Phe Leu Leu Ala Ser
1               5                   10

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:27:

AGGGAATTCC AYCGNGAYYT NGCNGC                                            26

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

AGGGGATCCR WARSWCCANA CRTC                                              24

(2) INFORMATION FOR SEQ ID NO:29:

(i) SEQUENCE CHARACTERISTICS:
        (A) LENGTH: 687 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Met Ala Arg Ala Arg Pro Pro Ser Leu Leu Leu Leu Leu Asp Ala
1               5                   10                  15

Leu Ala Ala Pro Ala Glu Val Thr Leu Leu Asp Ser Lys Thr Gln Gly
                20                  25                  30

Glu Leu Gly Trp Ile Ser His Pro Gly Trp Glu Ser Gly Asp
            35                  40                  45

Glu Asn Thr Pro Ile Arg Thr Tyr Gln Val Cys Asn Val Met Glu Ser
        50                  55                  60

Gln Asn Asn Trp Leu Arg Thr Asn Trp Ile Ala Phe Gln Asp Val Gly
65                  70                  75                  80

Ala Cys Ala Leu Val Ser Val Arg Val Tyr Lys Lys Cys Pro Ser Thr
                85                  90                  95

Val Asn Leu Ala Phe Pro Asp Thr Thr Gly Ala Asp Ser Ser Ser Leu
            100                 105                 110

Val Glu Val Arg Gly Cys Val Asn Asn Ala Glu Pro Pro Met Cys Ser
            115                 120                 125

Ala Asp Gly Glu Trp Leu Val Pro Ile Gly Lys Cys Cys Lys Ala Gly
        130                 135                 140

Tyr Glu Glu Gly Thr Ala Cys Gln Ala Cys Pro Cys Glu Pro Cys Gly
145                 150                 155                 160

Asn Val Arg Tyr Pro Arg Gln Leu Gly Leu Thr Thr Val Thr Val Ser
                165                 170                 175

Asp Leu Leu Ala His Thr Asn Tyr Thr Phe Glu Glu Ala Val Asn Gly
            180                 185                 190

Val Ser Leu Ser Pro Gln Ala Ser Val Ser Val Ile Thr Thr Asn Gln
            195                 200                 205

Ala Ala Pro Ser Val Thr Val Arg Ser Arg Ser Ser Leu Ser Trp Gln
        210                 215                 220

Glu Pro Arg Pro Asn Gly Val Ile Leu Tyr Glu Val Lys Tyr Tyr Glu
225                 230                 235                 240

-continued

```
Lys Asp Gln Glu Arg Ser Tyr Ile Val Lys Thr Ser Val Thr Asp Gly
            245                 250                 255

Leu Lys Pro Asp Thr Tyr Val Phe Gln Val Arg Ala Arg Thr Ala Ala
            260                 265                 270

Gly Tyr Gly Ser Arg Glu Phe Glu Thr Pro Glu Ala Ser Gly Ser Gly
            275                 280                 285

Ile Val Val Ile Ile Val Ser Ala Gly Ala Leu Leu Val Val Val
290                 295                 300

Leu Arg Arg Gln Ser Arg Asp Asp Glu Tyr Lys Glu Gln Lys Leu Pro
305                 310                 315                 320

Gly Lys Thr Tyr Ile Asp Pro Thr Tyr Glu Asp Pro Asn Gln Ala Val
                325                 330                 335

Glu Phe Ala Lys Glu Ile Asp Ala Ser Cys Ile Lys Ile Glu Lys Val
            340                 345                 350

Ile Gly Ala Gly Glu Phe Gly Glu Val Cys Ser Gly Arg Leu Lys Leu
            355                 360                 365

Pro Gly Lys Arg Glu Val Ala Ile Lys Thr Leu Lys Val Gly Tyr Thr
    370                 375                 380

Glu Lys Gln Arg Arg Asp Phe Leu Glu Ala Ser Ile Met Gly Gln Phe
385                 390                 395                 400

Asp His Pro Asn Ile Ile His Leu Glu Gly Val Val Thr Lys Ser Lys
                405                 410                 415

Pro Val Met Ile Ile Thr Glu Met Glu Asn Gly Leu Asp Phe Leu Arg
            420                 425                 430

Lys Asn Asp Gly Gln Phe Thr Val Ile Gln Leu Val Gly Met Leu Arg
            435                 440                 445

Gly Ile Ala Ala Gly Met Lys Tyr Leu Ser Asp Met Asn Tyr Val His
    450                 455                 460

Arg Asp Leu Ala Ala Arg Asn Ile Leu Val Asn Ser Asn Leu Val Cys
465                 470                 475                 480

Lys Val Ser Asp Phe Gly Leu Ser Arg Val Leu Glu Asp Asp Pro Glu
                485                 490                 495

Ala Tyr Thr Thr Arg Gly Gly Lys Ile Pro Ile Arg Trp Thr Ala Pro
            500                 505                 510

Glu Ala Ile Ala Tyr Arg Lys Phe Thr Ser Ala Ser Asp Val Trp Ser
            515                 520                 525

Tyr Gly Ile Val Met Trp Glu Val Met Ser Tyr Gly Glu Arg Pro Tyr
    530                 535                 540

Trp Met Ser Asn Gln Asp Val Ile Lys Ala Ile Glu Glu Gly Tyr Arg
545                 550                 555                 560

Leu Pro Pro Pro Met Asp Cys Pro Ala Ala Leu Gln Leu Met Leu Asp
                565                 570                 575

Cys Trp Gln Lys Arg Asn Arg Arg Pro Lys Phe Gln Ile Val Asn Ile
            580                 585                 590

Leu Asp Lys Leu Ile Arg Asn Pro Asn Ser Leu Lys Thr Ile Ala Ala
            595                 600                 605

Ser Ser Arg Ser Pro Leu Leu Asp Ser Gly Pro Asp Thr Thr Phe Arg
    610                 615                 620

Thr Val Gly Glu Trp Leu Glu Ala Ile Lys Met Gly Arg Tyr Lys Glu
625                 630                 635                 640

Phe Thr Ala Ala Gly Tyr Thr Ser Ala Val Ala Gln Met Thr Ala Glu
                645                 650                 655

Asp Leu Arg Ile Gly Val Thr Leu Val Gly His Gln Lys Lys Ile Leu
```

|                 660                 665                 670         |
|---|

Ser Ser Ile Gln Met Arg Gln Met Asn Gln Gly His Pro Val Val
        675                 680                 685

(2) INFORMATION FOR SEQ ID NO:30:

(i) SEQUENCE CHARACTERISTICS:
        (A) LENGTH: 967 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Ala Leu Arg Thr Leu Leu Ala Ser Pro Ser Asn Glu Val Asn Leu Leu
1               5                   10                  15

Asp Ser Arg Thr Val Met Gly Asp Leu Gly Trp Ile Ala Phe Pro Lys
                20                  25                  30

Asn Gly Trp Glu Glu Ile Gly Glu Val Asp Glu Asn Tyr Ala Pro Ile
            35                  40                  45

His Thr Tyr Gln Val Cys Lys Val Met Glu Gln Asn Gln Asn Asn Trp
        50                  55                  60

Leu Leu Thr Ser Trp Ile Ser Asn Glu Gly Ala Ser Arg Ile Phe Ile
65                  70                  75                  80

Glu Leu Lys Phe Thr Leu Arg Asp Cys Asn Ser Leu Pro Gly Gly Leu
                85                  90                  95

Gly Thr Cys Lys Glu Thr Phe Asn Met Tyr Tyr Phe Glu Ser Asp Asp
                100                 105                 110

Gln Asn Gly Arg Asn Ile Lys Glu Asn Gln Tyr Ile Lys Ile Asp Thr
            115                 120                 125

Ile Ala Ala Asp Glu Ser Phe Thr Glu Leu Asp Leu Gly Asp Arg Val
        130                 135                 140

Met Lys Leu Asn Thr Glu Val Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Tyr Tyr Lys Lys Cys Pro Ser Val Val Arg His Leu
                180                 185                 190

Ala Val Phe Pro Asp Thr Ile Thr Gly Ala Asp Ser Ser Gln Leu Leu
            195                 200                 205

Glu Val Ser Gly Ser Cys Val Asn His Ser Val Thr Asp Glu Pro Pro
        210                 215                 220

Lys Met His Cys Ser Ala Glu Gly Glu Trp Leu Val Pro Ile Gly Lys
225                 230                 235                 240

Cys Met Cys Lys Ala Gly Tyr Glu Glu Lys Asn Gly Thr Cys Gln Val
                245                 250                 255

Cys Arg Pro Gly Phe Phe Lys Ala Ser Pro His Ile Gln Ser Cys Gly
                260                 265                 270

Lys Cys Pro Pro His Ser Tyr Thr His Glu Glu Ala Ser Thr Ser Cys
            275                 280                 285

Val Cys Glu Lys Asp Tyr Phe Arg Arg Glu Ser Asp Pro Pro Thr Met
        290                 295                 300

Ala Cys Thr Arg Pro Pro Ser Ala Pro Arg Asn Ala Ile Ser Asn Val
305                 310                 315                 320

Asn Glu Thr Ser Val Phe Leu Glu Trp Ile Pro Pro Ala Asp Thr Gly

-continued

```
                325                 330                 335
Gly Arg Lys Asp Val Ser Tyr Tyr Ile Ala Cys Lys Lys Cys Asn Ser
            340                 345                 350
His Ala Gly Val Cys Glu Glu Cys Gly Gly His Val Arg Tyr Leu Pro
            355                 360                 365
Arg Gln Ser Gly Leu Lys Asn Thr Ser Val Met Met Val Asp Leu Leu
            370                 375                 380
Ala His Thr Asn Tyr Thr Phe Glu Ile Glu Ala Val Asn Gly Val Ser
385                 390                 395                 400
Asp Leu Ser Pro Gly Ala Arg Gln Tyr Val Ser Val Asn Val Thr Thr
            405                 410                 415
Asn Gln Ala Ala Pro Ser Pro Val Thr Asn Val Lys Lys Gly Lys Ile
            420                 425                 430
Ala Lys Asn Ser Ile Ser Leu Ser Trp Gln Glu Pro Asp Arg Pro Asn
            435                 440                 445
Gly Ile Ile Leu Glu Tyr Glu Ile Lys His Phe Glu Lys Asp Gln Glu
            450                 455                 460
Thr Ser Tyr Thr Ile Ile Lys Ser Lys Glu Thr Thr Ile Thr Ala Glu
465                 470                 475                 480
Gly Leu Lys Pro Ala Ser Val Tyr Val Phe Gln Ile Arg Ala Arg Thr
            485                 490                 495
Ala Ala Gly Tyr Gly Val Phe Ser Arg Arg Phe Glu Phe Glu Thr Thr
            500                 505                 510
Pro Val Phe Ala Ala Ser Ser Asp Gln Ser Gln Ile Pro Val Ile Ala
            515                 520                 525
Val Ser Val Thr Val Gly Val Ile Leu Leu Ala Val Val Ile Gly Val
            530                 535                 540
Leu Leu Ser Gly Arg Arg Cys Gly Tyr Ser Lys Ala Lys Gln Asp Pro
545                 550                 555                 560
Glu Glu Glu Lys Met His Phe His Asn Gly His Ile Lys Leu Pro Gly
            565                 570                 575
Val Arg Thr Tyr Ile Asp Pro His Thr Tyr Glu Asp Pro Asn Gln Ala
            580                 585                 590
Val His Glu Phe Ala Lys Glu Ile Glu Ala Ser Cys Ile Thr Ile Glu
            595                 600                 605
Arg Val Ile Gly Ala Gly Glu Phe Gly Glu Val Cys Ser Gly Arg Leu
            610                 615                 620
Lys Leu Pro Gly Lys Arg Glu Leu Pro Val Ala Ile Lys Thr Leu Lys
625                 630                 635                 640
Val Gly Tyr Thr Glu Lys Gln Arg Arg Asp Phe Leu Gly Glu Ala Ser
            645                 650                 655
Ile Met Gly Gln Phe Asp His Pro Asn Ile Ile His Leu Glu Gly Val
            660                 665                 670
Val Thr Lys Ser Lys Pro Val Met Ile Val Thr Glu Tyr Met Glu Asn
            675                 680                 685
Gly Ser Leu Asp Thr Phe Leu Lys Lys Asn Asp Gly Gln Phe Thr Val
            690                 695                 700
Ile Gln Leu Val Gly Met Leu Arg Gly Ile Ser Ala Gly Met Lys Tyr
705                 710                 715                 720
Leu Ser Asp Met Gly Tyr Val His Arg Asp Leu Ala Ala Arg Asn Ile
            725                 730                 735
Leu Ile Asn Ser Asn Leu Val Cys Lys Val Ser Asp Phe Gly Leu Ser
            740                 745                 750
```

-continued

```
Arg Val Leu Glu Asp Asp Pro Glu Ala Ala Tyr Thr Thr Arg Gly Gly
            755                 760                 765

Lys Ile Pro Ile Arg Trp Thr Ala Pro Glu Ala Ile Ala Phe Arg Lys
        770                 775                 780

Phe Thr Ser Ala Ser Asp Val Trp Ser Tyr Gly Ile Val Met Trp Glu
785                 790                 795                 800

Val Val Ser Tyr Gly Glu Arg Pro Tyr Trp Glu Met Thr Asn Gln Asp
                805                 810                 815

Val Ile Lys Ala Val Glu Glu Gly Tyr Arg Leu Pro Ser Pro Met Asp
            820                 825                 830

Cys Pro Ala Ala Leu Tyr Gln Leu Met Leu Asp Cys Trp Gln Lys Glu
        835                 840                 845

Arg Asn Ser Arg Pro Lys Phe Asp Glu Ile Val Asn Met Leu Asp Lys
850                 855                 860

Leu Ile Arg Asn Pro Ser Ser Leu Lys Thr Leu Val Asn Ala Ser Cys
865                 870                 875                 880

Arg Val Ser Asn Leu Leu Ala Glu His Ser Pro Leu Gly Ser Gly Ala
                885                 890                 895

Tyr Arg Ser Val Gly Glu Trp Leu Glu Ala Ile Lys Met Gly Arg Tyr
            900                 905                 910

Thr Glu Ile Phe Met Glu Asn Gly Tyr Ser Ser Met Asp Ala Val Ala
        915                 920                 925

Gln Val Thr Leu Glu Asp Leu Arg Arg Leu Gly Val Thr Leu Val Gly
    930                 935                 940

His Gln Lys Lys Ile Met Asn Ser Leu Gln Glu Met Lys Val Gln Leu
945                 950                 955                 960

Val Asn Gly Met Val Pro Leu
                965
```

(2) INFORMATION FOR SEQ ID NO:31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GAATTCGTCG ACCCGGCGAA CCATGGCTGG GAT        33

(2) INFORMATION FOR SEQ ID NO:32:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GAATTCTCTA GATTATCATG TGGAGTTAGC CCCATCTC        38

(2) INFORMATION FOR SEQ ID NO:33:

(i) SEQUENCE CHARACTERISTICS:
        (A) LENGTH: 59 base pairs
        (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:33:

TCGCCCTATT TTCGTGTCTC TTCGGGATTT GCGACGCTCT CCGGACCCTC CTGGCCAGC      59

(2) INFORMATION FOR SEQ ID NO:34:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:34:

GAATTCTCTA GATTATCACT GGCTTTGATC GCTGGAT                               37

(2) INFORMATION FOR SEQ ID NO:35:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:35:

GAATTCGTCG ACCCGGCGAA CCATGGCTGG GATTTTCTAT TTCGCCCTAT TTCGTGTCT      60

(2) INFORMATION FOR SEQ ID NO:36:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:36:

GAATTCTCTA GATTATCACT GGCTTTGATC GCTGGAT                               37

(2) INFORMATION FOR SEQ ID NO:37:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:37:

Met Ala Gly Ile Phe Tyr Phe Ala Leu Phe Ser Cys Leu Phe Gly Ile
1               5                   10                  15
Cys Asp (2) INFORMATION FOR SEQ ID NO:38:

(i) SEQUENCE CHARACTERISTICS:
            (A) LENGTH: 13 amino acids
            (B) TYPE: amino acid
            (C) STRANDEDNESS: single
```

```
        (D) TOPOLOGY: linear (ii) MOLECULE TYPE: protein (xi) SEQUENCE DESCRIPTION: SEQ ID NO:38:

Cys Leu Glu Thr Gln Ser Lys Asn Gly Pro Val Pro Val
1               5                   10

(2) INFORMATION FOR SEQ ID NO:39:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

Cys Arg Ala Gln Met Asn Gln Ile Gln Ser Val Glu Val
1               5                   10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Cys Met Lys Val Gln Leu Val Asn Gly Met Val Pro Leu
1               5                   10

(2) INFORMATION FOR SEQ ID NO:41:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Cys Met Arg Thr Gln Met Gln Gln Met His Gly Arg Met Val Pro Val
1               5                   10                  15

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Cys Gln Met Leu His Leu His Gly Thr Gly Ile Gln Val
1               5                   10

(2) INFORMATION FOR SEQ ID NO:43:

(i) SEQUENCE CHARACTERISTICS:
        (A) LENGTH: 10 amino acids
        (B) TYPE: amino acid
```

```
        (C) STRANDEDNESS: single
        (D) TOPOLOGY: linear (ii) MOLECULE TYPE: protein (xi) SEQUENCE DESCRIPTION: SEQ ID NO:43:

Cys Cys Cys Gly Cys Thr Thr Ala Ala Gly
1               5                   10
```